US011401271B2

(12) United States Patent
Xu et al.

(10) Patent No.: US 11,401,271 B2
(45) Date of Patent: Aug. 2, 2022

(54) FUSED HETEROCYCLIC COMPOUND, PYRAZOLE-RING-CONTAINING FUSED HETEROCYCLIC COMPOUND, AGRICULTURAL COMPOSITION CONTAINING THEREOF, AND METHOD OF USING THE COMPOSITION

(71) Applicant: SOUTH CHINA AGRICULTURAL UNIVERSITY, Guangdong (CN)

(72) Inventors: Hanhong Xu, Guangdong (CN); Xunyuan Jiang, Guangdong (CN); Xiaoyi Wei, Guangdong (CN); Zhixiang Zhang, Guangdong (CN); Fei Lin, Guangdong (CN); Guangkai Yao, Guangdong (CN); Chengju Deng, Guangdong (CN); Chen Zhao, Guangdong (CN); Shuai Yang, Guangdong (CN); Weijing Zhao, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 106 days.

(21) Appl. No.: 16/758,053

(22) PCT Filed: Nov. 2, 2018

(86) PCT No.: PCT/CN2018/113811
§ 371 (c)(1),
(2) Date: Apr. 22, 2020

(87) PCT Pub. No.: WO2019/086009
PCT Pub. Date: May 9, 2019

(65) Prior Publication Data
US 2021/0188853 A1 Jun. 24, 2021

(30) Foreign Application Priority Data
Nov. 3, 2017 (CN) .......................... 201711069917.7
Mar. 16, 2018 (CN) .......................... 201810219338.4

(51) Int. Cl.
*C07D 487/04* (2006.01)
*A01N 43/90* (2006.01)
*C07D 471/14* (2006.01)
*C07D 487/14* (2006.01)

(52) U.S. Cl.
CPC ........... *C07D 487/04* (2013.01); *A01N 43/90* (2013.01); *C07D 471/14* (2013.01); *C07D 487/14* (2013.01)

(58) Field of Classification Search
CPC .. C07D 487/04; C07D 471/14; C07D 487/14; A01N 43/90
See application file for complete search history.

(56) References Cited

U.S. PATENT DOCUMENTS

| 4,072,680 | A | 2/1978 | Denzel et al. |
| 2013/0150414 | A1 | 6/2013 | Kagabu et al. |
| 2015/0173359 | A1* | 6/2015 | Frackenpohl ........ C07D 239/91 |
| | | | 504/225 |

FOREIGN PATENT DOCUMENTS

| CN | 102892290 | | 1/2013 |
| CN | 103254125 | | 8/2013 |
| CN | 103960242 | | 8/2014 |
| CN | 107108626 | | 8/2017 |
| CN | 108003162 | | 5/2018 |
| CN | 108129481 | | 6/2018 |
| DE | 102006015467 | | 10/2007 |
| EP | 0580374 | | 1/1994 |
| EP | 2305678 | | 4/2011 |
| JP | 2003201280 | | 7/2003 |
| KR | 2016040826 | * | 4/2016 |
| WO | 9805638 | | 2/1998 |
| WO | 0214263 | | 2/2002 |
| WO | 2004067528 | | 8/2004 |
| WO | 2007095229 | | 8/2007 |
| WO | 2007144669 | | 12/2007 |
| WO | 2007149907 | | 12/2007 |
| WO | 2010069266 | | 6/2010 |
| WO | 2013174822 | | 11/2013 |
| WO | 2016046404 | | 3/2016 |

OTHER PUBLICATIONS

Yang; Pest Management Science 2021, 77, 1013-1022. DOI: 10.1002/ps.6113 (Year: 2021).*
National Center for Biotechnology Information. PubChem Substance Record for SID 344180132, SCHEMBL19134571, Source: SureChEMBL. Deposit Date Oct. 7, 2017. Downloaded Dec. 9, 2021 from: https://pubchem.ncbi.nlm.nih.gov/substance/344180132 (Year: 2017).*
Supplemental European Search Report in Application EP18873292, dated Jul. 20, 2020. 5 pages. (Year: 2020).*
John E. Casida, et al., "Novel GABA receptor pesticide targets," Pesticide Biochemistry and Physiology, vol. 121, Nov. 2014, pp. 22-30.
Jaime Gálvez, et al., "Design, facile synthesis, and evaluation of novel spiro- and pyrazolo[1,5-c]quinazolines as cholinesterase inhibitors: Molecular docking and MM/GBSA studies," Computational Biology and Chemistry, vol. 74, Mar. 2018, pp. 218-229.
Zhen Fang, et al., "Discovery of pyrazolo[1,5-a]pyrimidine-3-carbonitrile derivatives as a new class of histone lysine demethylase 4D (KDM4D) inhibitors," Bioorganic & Medicinal Chemistry Letters, vol. 27, May 2017, pp. 3201-3204.

(Continued)

*Primary Examiner* — Daniel R Carcanague
(74) *Attorney, Agent, or Firm* — JCIPRNET

(57) ABSTRACT

A fused tricyclic compound, an optical isomer, cis and trans isomers or an agromedically acceptable salt thereof, and insecticidal use thereof in agroforestry. A pyrazole-ring-contained fused heterocyclic compound, an agricultural composition, and a method of using the agricultural composition are also provided.

18 Claims, No Drawings

(56) References Cited

OTHER PUBLICATIONS

Gabriella Guerrini, et al., "Identification of a New Pyrazolo[1,5-a]quinazoline Ligand Highly Affine to y-Aminobutyric Type A (GABAA) Receptor Subtype with Anxiolytic-Like and Antihyperalgesic Activity," J Med Chem., Nov. 2017, pp. 1-12.
Gabriella Guerrini, et al., "Synthesis and Pharmacological Evaluation of Novel GABAA Subtype Receptor Ligands with Potential Anxiolytic-like and Anti-hyperalgesic Effect," Journal of Heterocyclic Chemistry, vol. 54, Sep. 2017, pp. 2788-2799.
Carson Wiethan, et al., "Synthesis of pyrazolo[1,5-a]quinoxalin-4(5H)-ones via one-pot amidation/N-arylation reactions under transition metal-free conditions," Organic & Biomolecular Chemistry, Aug. 2016, pp. 1-7.
Gabriella Guerrini, et al., "Pyrazolo[1,5-a]quinazoline scaffold as 5-deaza analogue of pyrazolo[5,1-c][1,2,4] benzotriazine system: synthesis of new derivatives, biological activity on GABAA receptor subtype and molecular dynamic study," J Enzyme Inhib Med Chem., Mar. 2015, pp. 1-21.
Miaomiao Niu, et al., "An in silico protocol for identifying potential poly(ADP-ribose)polymerase-1 (PARP-1) inhibitors from chemical databases," New Journal of Chemistry, Oct. 2014, pp. 1-7.
Takeo Fukuzumi, et al., "Exploratory Study on the RNA-Binding Structural Motifs by Library Screening Targeting pre-miRNA-29a," Chemistry—A European Journal, Oct. 2015, pp. 16859-16867.
Cody J. Wenthur, et al., "Synthesis and SAR of substituted pyrazolo[1,5-a]quinazolines as dual mGlu2/mGlu3 NAMs," Bioorganic & Medicinal Chemistry Letters, vol. 24, Apr. 2014, pp. 2693-2698.
Sabrina Taliani, et al., "Phenylpyrazolo[1,5-a]quinazolin-5(4H)-one: A Suitable Scaffold for the Development of Noncamptothecin Topoisomerase I (Top1) Inhibitors," J Med Chem., Aug. 2013, pp. 1-24.
Federica Orvieto, et al., "Identification of substituted pyrazolo[1,5-a]quinazolin-5(4H)-one as potent poly(ADP-ribose)polymerase-1 (PARP-1) inhibitors," Bioorganic & Medicinal Chemistry Letters, vol. 19, May 2009, pp. 4196-4200.
Michael B. Tropak, et al., "High-Throughput Screening for Human Lysosomal b-N-Acetyl Hexosaminidase Inhibitors Acting as Pharmacological Chaperones," Chemistry & Biology, vol. 14, Feb. 2007, pp. 153-164.
Sandriyana Soelaiman, et al., "Structure-based Inhibitor Discovery against Adenylyl Cyclase Toxins from Pathogenic Bacteria That Cause Anthrax and Whooping Cough," Journal of Biological Chemistry, vol. 278, Apr. 2003, pp. 1-9.
Flavia Varano, et al., "Synthesis and Biological Evaluation of a New Set of Pyrazolo[1,5-c]quinazoline-2-carboxylates as Novel Excitatory Amino Acid Antagonists," Journal of Medicinal Chemistry, vol. 45, May 2002, pp. 1035-1044.
Krishna Kumar Gnanasekaran, et al., "Pyrazoloquinazolinones and pyrazolopyridopyrimidinones by a sequential N-acylation-SNAr reaction," Tetrahedron Letters, vol. 56, Jan. 2015, pp. 1367-1369.
Xinying Zhang, et al., "Water-Mediated Selective Synthesis of Pyrazolo[1,5-a]quinazolin-5(4H)-ones and [1,2,4]Triazolo[1,5-a]quinazolin-5(4H)-one via Copper-Catalyzed Cascade Reactions," Synthetic Communications, vol. 45, Aug. 2015, pp. 1-11.
Lin Gao, et al., "Copper-catalyzed tandem reactions of 2-bromobenzaldehydes/ ketones with aminopyrazoles toward the synthesis of pyrazolo [1,5-a]quinazolines," Tetrahedron Letters, vol. 55, Jul. 2014, pp. 4997-5002.
Hyun, S.Y. et al., "Aromatic compound as electroluminescent host or hole transport material," Chemical Abstract, Dec. 2016, pp. 1-5.

\* cited by examiner

FUSED HETEROCYCLIC COMPOUND, PYRAZOLE-RING-CONTAINING FUSED HETEROCYCLIC COMPOUND, AGRICULTURAL COMPOSITION CONTAINING THEREOF, AND METHOD OF USING THE COMPOSITION

CROSS-REFERENCE TO RELATED APPLICATION

This application is a 371 of international application of PCT application serial no. PCT/CN2018/113811, filed on Nov. 2, 2018, which claims the priority benefit of China application no. 201711069917.7, filed on Nov. 3, 2017 and China application no. 201810219338.4, filed on Mar. 16, 2018. The entirety of each of the above mentioned patent applications is hereby incorporated by reference herein and made a part of this specification.

TECHNICAL FIELD

The present invention belongs to the field of heterocyclic compounds, and more particularly, relates to a fused heterocyclic compound, and an optical isomer, cis and trans isomers or an agromedically acceptable salt thereof, as well as a preparation method and use thereof.

BACKGROUND

New heterocyclic pesticides represented by nitrogen-containing heterocycles have the advantages of high insecticidal activity, wide insecticidal spectrum, low toxicity to mammals and appropriate field stability, so that heterocyclic compounds have become an important hotspot field in the development of new pesticides. In recent years, newly developed pesticides such as Flupyrimin, flupyradifurone, cycloxaprid, sulfoxaflor, flonicamid, spirotetramat, cyflumetofen, cyenopyrafen, cyantraniliprole and the like, all belong to the nitrogen-containing heterocyclic compounds (with reference to patents US2013150414, CN103960242, CN103254125, CN102892290, DE102006015467, WO2010069266, WO2007095229, EP580374, WO9805638, WO2002014263, JP2003201280 and WO2004067528).

However, the problems of serious resistance and cross resistance are caused due to excessive and frequent use of a single pesticide and a high toxicity of the existing insecticide to the environment while killing pests, which reduces an efficacy of the pesticide and greatly restricts use of the pesticide, thus restricting the development of agriculture and forestry. Therefore, how to develop a new pesticide that is more efficient and environmentally friendly and how to solve the problem of resistance become technical problems to be urgently solved in this field.

New structural molecules with big structural differences from previous pesticide molecules are believed to have no cross resistance with the existing pesticides, and may be used to control the development of pest resistance (Pestide Biochemistry and Physiology, 2015, 121: 22). In recent years, multiple series of fused heterocyclic compounds have been synthesized and reported to have an extensive bioactivity (such as Computational Biology and Chemistry, 2018, 74: 218; Bioorganic & Medicinal Chemistry Letters, 2017, 27: 3201; Journal of Medicinal Chemistry, 2017, 60: 9691; Journal of Heterocyclic Chemistry, 2017, 54: 2788; Organic & Biomolecular Chemistry, 2016, 14: 8721; Journal of Enzyme Inhibition and Medicinal Chemistry, 2015, 31: 195; New Journal of Chemistry, 2015, 39: 1060; Chemistry-A European Journal, 2015, 21: 16859; Bioorganic & Medicinal Chemistry Letters, 2014, 24: 2693; Journal of Medicinal Chemistry, 2013, 56: 7458; Bioorganic & Medicinal Chemistry Letters, 2009, 19: 4196; Chemistry & Biology, 2007, 14: 153; Journal of Biological Chemistry, 2003, 278: 25990; and Journal of Medicinal Chemistry, 2002, 45: 1035). Based on this, a large number of new fused heterocyclic compounds have been designed, synthesized and screened in this study. These compounds with novel structures have excellent control effects on a variety of pests and even on pests with resistance.

SUMMARY

According to an aspect of the invention, there is provided a nitrogen-containing fused tricyclic compound, and an optical isomer, cis and trans isomers or an agromedically acceptable salt thereof. The fused heterocyclic compound and the optical isomer, the cis and trans isomers or the agromedically acceptable salt thereof have a high killing activity on agroforestry pests and sanitary insect pests and sanitary pests, and more surprisingly, have a delayed working effect on pests such as Solenopsis invicta, thereby having a better killing effect.

According to another aspect of the invention, there is provided a method for preparing the fused tricyclic compound, and the optical isomer, the cis and trans isomers or the agromedically acceptable salt thereof.

According to another aspect of the invention, these is provided a method of using the fused heterocyclic compound and the optical isomer, the cis and trans isomers or the agromedically acceptable salt thereof in preparing an insecticide.

In order to achieve the above objects, the technical solutions adopted by the present invention are as follows.

A fused heterocyclic compound, and an optical isomer, cis and trans isomers or an agromedically acceptable salt thereof, wherein the fused heterocyclic compound has a structure shown in formula (I):

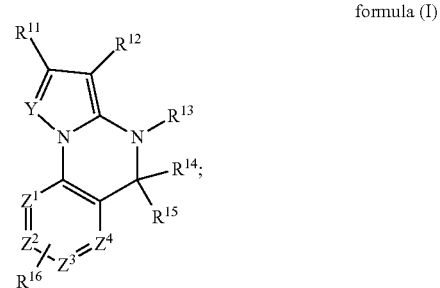

formula (I)

wherein $R^{11}$ and $R^{12}$ are each independently hydrogen, halogen, $-NO_2$, $-CN$, $-COR^{17}$, $-CO_2R^{17}$, $-CONR^{17}R^{18}$, $-S(O)\ R^{17}$, $-S(O)_2\ R^{17}$, $-N\ R^{17}\ R^{18}$, $-N\ R^{17}CO\ R^{18}$, $-N\ R^{17}CON\ R^{18}R^{19}$, $-N\ R^{17}CO_2\ R^{18}$, $-N\ R^{17}S(O)_2\ R^{18}$, alkyl, heteroalkyl, alkenyl, cycloalkyl, cycloalkenyl, aryl, heterocyclyl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$; and $R^{13}$ is hydrogen, $-COR^{17}$, $-CO_2\ R^{17}$, $-S(O)_2\ R^{17}$, $-CONR^{17}R^{18}$, alkyl, heteroalkyl, alkenyl, cycloalkyl, cycloalkenyl and aryl; wherein the alkyl, the alkenyl, the cycloalkyl, the cycloalkenyl and the aryl are unsubstituted or substituted with one or more substituents $R^{10}$;

$R^{14}$ and $R^{15}$ are each independently hydrogen, halogen, —CN, —OH, —N $R^{17}$ $R^{18}$, —O $R^{17}$, —CO $R^{17}$, —CO$_2$ $R^{17}$, —CONR$^{17}$R$^{18}$, —N R$^{17}$CO R$^{18}$, —NR$^{17}$CON R$^{18}$R$^{19}$, —NR$^{17}$CO$_2$R$^{18}$, —NR$^{17}$S(O)$_2$R$^{18}$, —S(O)R$^{17}$, —S(O)$_2$R$^{17}$, alkyl, heteroalkyl, alkenyl, cycloalkyl, cycloalkenyl, aryl, heterocyclyl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$, and $R^{14}$ and $R^{15}$ are not hydrogen at the same time;

Y is N or CH;

$Z^1$, $Z^2$, $Z^3$ and $Z^4$ are each independently C or N, under conditions that at most two of $Z^1$ to $Z^4$ are N, and a ring containing $Z^1$ to $Z^4$ is aromatic;

$R^{16}$ represents a substituent on the ring containing $Z^1$ to $Z^4$, one or more $R^{16}$ are provided, and each $R^{16}$ is independently hydrogen, halogen, —CN, alkyl, heteroalkyl, —CO R$^{17}$, —CO$_2$ R$^{17}$, —N R$^{17}$ R$^{18}$, —CONR$^{17}$R$^{18}$, —N R$^{17}$CO R$^{18}$, —NR$^{17}$CON R$^{18}$R$^{19}$, —NR$^{17}$CO$_2$R$^{18}$ or —NR$^{17}$S(O)$_2$R$^{18}$;

$R^{17}$, $R^{18}$ and $R^{19}$ are each independently hydrogen, alkyl, heteroalkyl, alkenyl, cycloalkyl, cycloalkenyl, heterocyclyl, aryl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$; and $R^{10}$ is halogen, $C_1$-$C_6$ alkyl, $C_2$-$C_6$ alkenyl, substituted or unsubstituted cycloalkyl, cycloalkenyl, substituted or unsubstituted aryl, substituted or unsubstituted heteroaryl, substituted or unsubstituted heterocyclyl, —CN, —NH$_2$, —OR''', —NR'''R'''', —COR''', —CO$_2$R''', —CONR'''R'''', —NR'''COR'''', —NR'''CONR'''R'''', —NR'''CO$_2$R'''', —S(O)$_2$R''' or —NR'''S(O)$_2$R'''', wherein R''' and R'''' are each independently hydrogen, $C_1$-$C_6$ alkyl, $C_2$-$C_6$ alkenyl, cycloalkyl, cycloalkenyl, aryl, heteroaryl or heterocyclyl.

Preferably, when Y is N or CH;

$R^{11}$ is halogen, —CN, —COR$^{17}$, —CONR$^{17}$R$^{18}$, —S(O) R$^{17}$, —N R$^{17}$ R$^{18}$, —N R$^{17}$CO R$^{18}$, aryl, heterocyclyl or heteroaryl; wherein the alkyl, the heterocyclyl or the heteroaryl is unsubstituted or substituted with one or more substituents $R^{10}$;

$R^{12}$ is hydrogen, —COR$^{17}$, —CONR$^{17}$R$^{18}$, —S(O)R$^{17}$, —S(O)$_2$R$^{17}$, —N R$^{17}$ R$^{18}$, —N R$^{17}$CO R$^{18}$, —NR$^{17}$CONR$^{18}$R$^{19}$, —NR$^{17}$CO$_2$R$^{18}$, aryl, heterocyclyl or heteroaryl; wherein the alkyl, the heterocyclyl or the heteroaryl is unsubstituted or substituted with one or more substituents $R^{10}$;

$R^{13}$ is hydrogen, —COR$^{17}$, alkyl, heteroalkyl or alkenyl;

$R^{14}$ is halogen, —CN, —N R$^{17}$ R$^{18}$, —O R$^{17}$, —CO R$^{17}$, —CO$_2$ R$^{17}$, —CONR$^{17}$R$^{18}$, —N R$^{17}$CO R$^{18}$, —NR$^{17}$CO$_2$R$^{18}$, alkyl, heteroalkyl or alkenyl; wherein the alkyl, the heteroalkyl or the alkenyl is unsubstituted or substituted with one or more substituents $R^{10}$; and $R^{15}$ is hydrogen, halogen, —CN, —N R$^{17}$ R$^{18}$, —O R$^{17}$, —CO R$^{17}$, —CO$_2$ R$^{17}$, —CONR$^{17}$R$^{18}$, —N R$^{17}$CO R$^{18}$, —NR$^{17}$CO$_2$R$^{18}$, alkyl, heteroalkyl or alkenyl; wherein the alkyl, the heteroalkyl or the alkenyl is unsubstituted or substituted with one or more substituents $R^{10}$.

Preferably, when $Z^1$, $Z^2$, $Z^3$ and $Z^4$ are all C, one or more $R^{16}$ are provided, and each $R^{16}$ is independently hydrogen, halogen, alkyl, heteroalkyl, alkenyl, —S(O) R$^{17}$, —S(O)$_2$ R$^{17}$, —COR$^{17}$, —N R$^{17}$ R$^{18}$, —CONR$^{17}$R$^{18}$, —N R$^{17}$CO R$^{18}$ or —NR$^{17}$S(O)$_2$R$^{18}$;

$R^{11}$ is halogen, —CN, —COR$^{17}$, —CONR$^{17}$R$^{18}$, —S(O) R$^{17}$, —N R$^{17}$ R$^{18}$, —N R$^{17}$CO R$^{18}$, aryl, heterocyclyl or heteroaryl; wherein the alkyl, the heterocyclyl or the heteroaryl is unsubstituted or substituted with one or more substituents $R^{10}$;

$R^{12}$ is —CONR$^{17}$R$^{18}$, —S(O) R$^{17}$, —S(O)$_2$ R$^{17}$, —N R$^{17}$ R$^{18}$, —N R$^{17}$CO R$^{18}$, —N R$^{17}$CON R$^{18}$R$^{19}$, aryl, heterocyclyl or heteroaryl; wherein the alkyl, the heterocyclyl or the heteroaryl is unsubstituted or substituted with one or more substituents $R^{10}$;

$R^{13}$ is hydrogen, —COR$^{17}$, alkyl or alkenyl; and $R^{14}$ and $R^{15}$ are each independently halogen, —CN, —N R$^{17}$ R$^{18}$, —O R$^{17}$, —CO R$^{17}$, —CO$_2$ R$^{17}$, —CONR$^{17}$R$^{18}$, —N R$^{17}$CO R$^{18}$, —NR$^{17}$CO$_2$R$^{18}$, alkyl, heteroalkyl and alkenyl; wherein the alkyl, the heteroalkyl and the alkenyl are unsubstituted or substituted with one or more substituents $R^{10}$.

More preferably, when Y is N or CH;

$R^{11}$ is halogen, —CN, —COR$^{17}$, —CONR$^{17}$R$^{18}$, —S(O) R$^{17}$, —N R$^{17}$ R$^{18}$ or —N R$^{17}$CO R$^{18}$;

$R^{12}$ is —S(O) R$^{17}$, —S(O)$_2$ R$^{17}$, —N R$^{17}$ R$^{18}$, —N R$^{17}$CO R$^{18}$, aryl or heteroaryl; wherein the aryl or the heteroaryl is unsubstituted or substituted with one or more substituents $R^{10}$;

$R^{13}$ is hydrogen, —COR$^{17}$, alkyl or alkenyl;

$R^{14}$ and $R^{15}$ are each independently halogen, —CN, —N R$^{17}$ R$^{18}$, —O R$^{17}$, —CO R$^{17}$, —CO$_2$ R$^{17}$, —CONR$^{17}$R$^{18}$, —N R$^{17}$CO R$^{18}$, —NR$^{17}$CO$_2$R$^{18}$, alkyl, heteroalkyl or alkenyl; wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen, alkyl, heteroalkyl, —S(O) R$^{17}$, —S(O)$_2$ R$^{17}$, —COR$^{17}$, —N R$^{17}$ R$^{18}$, —N R$^{17}$CO R$^{18}$ or —NR$^{17}$S(O)$_2$R$^{18}$.

More preferably, $R^{11}$ is halogen, —CN, —COR$^{17}$ or —CONR$^{17}$R$^{18}$;

$R^{12}$ is —S(O)R$^{17}$, —S(O)$_2$R$^{17}$, —NR$^{17}$COR$^{18}$, aryl or heteroaryl; wherein the aryl or the heteroaryl is unsubstituted or substituted with one or more substituents $R^{10}$;

$R^{13}$ is hydrogen, —COR$^{17}$ or alkyl; and $Z^1$, $Z^2$, $Z^3$ and $Z^4$ are all C, one or more $R^{16}$ are provided, and each $R^{16}$ is independently halogen, heteroalkyl, —S(O) R$^{17}$, —NR$^{17}$R$^{18}$ or —NR$^{17}$COR$^{18}$.

More preferably, $R^{11}$ is —CN or —COR$^{17}$;

$R^{12}$ is —S(O)R$^{17}$ or aryl; wherein the aryl is substituted with one or more substituents $R^{10}$;

$R^{13}$ is hydrogen, —COR$^{17}$, methyl or ethyl;

$R^{14}$ and $R^{15}$ are each independently halogen, —OR$^{17}$, —COR$^{17}$, —CO$_2$R$^{17}$, —CONR$^{17}$R$^{18}$, —NR$^{17}$COR$^{18}$, —NR$^{17}$CO$_2$R$^{18}$, alkyl, heteroalkyl or alkenyl; wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen or heteroalkyl.

More preferably, $R^{11}$ is —CN or —$COR^{17}$, and $R^{17}$ is alkyl or heteroalkyl;

$R^{12}$ is —$S(O)R^{17}$, and $R^{17}$ is alkyl or heteroalkyl;

$R^{13}$ is hydrogen, —$COR^{17}$, methyl or ethyl, and $R^{17}$ is alkyl;

$R^{14}$ and $R^{15}$ are each independently halogen, —$OR^{17}$, —$COR^{17}$, —$CO_2R^{17}$, —$CONR^{17}R^{18}$, —$NR^{17}COR^{18}$, —$NR^{17}CO_2R^{18}$, alkyl, heteroalkyl or alkenyl; wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen or heteroalkyl.

The present invention further discloses a pyrazole-ring-containing fused heterocyclic compound, and an optical isomer, cis and trans isomers or an agromedically acceptable salt thereof, wherein the pyrazole-ring-containing fused heterocyclic compound has a structure shown in formula (II):

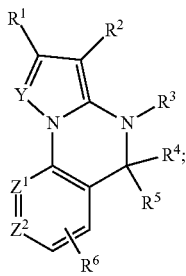

formula (II)

wherein $R^1$ is hydrogen, halogen, —CN, alkyl, heteroalkyl, aryl or heteroaryl; wherein the alkyl, the aryl or the heteroaryl is unsubstituted or substituted with one or more substituents $R^9$; and $R^2$ is hydrogen, halogen, —CN, —$S(O)R^7$, —$S(O)_2R^7$, alkyl, heteroalkyl, aryl or heteroaryl; wherein the alkyl, the aryl or the heteroaryl is unsubstituted or substituted with one or more substituents $R^9$; and $R^3$ is hydrogen, —$COR^7$, alkyl or heteroalkyl;

$R^4$ and $R^5$ are each independently hydrogen, halogen, —CN, —$COR^7$, —$CO_2R^7$, —$CH_2COR^7$, —$CH_2COOR^7$, amino, alkyl, heteroalkyl, aryl or heteroaryl; wherein the amino, the alkyl, the aryl or the heteroaryl is unsubstituted or substituted by one or more substituents $R^9$, and $R^4$ and $R^5$ are not hydrogen at the same time;

$Z^1$ and $Z^2$ are independently C or N, and are not N at the same time, and a ring containing $Z^1$ and $Z^2$ is an aromatic ring;

$R^6$ represents a substituent on the ring containing $Z^1$ and $Z^2$, one or more $R^6$ are provided, and each $R^6$ is independently hydrogen, halogen, —$NO_2$, —CN, alkyl, heteroalkyl, —$OR^7$, —$COR^7$, —$CO_2R^7$ or —$NR^7R^8$;

$R^7$ and $R^8$ are each independently hydrogen, hydroxyl, amino, $C_1$-$C_6$ alkyl, heteroalkyl, aryl or heteroaryl; wherein the alkyl, the aryl or the heteroaryl is unsubstituted or substituted with one or more substituents $R^9$; and $R^9$ is halogen, $C_1$-$C_6$ alkyl, heteroalkyl, —CN, —$NH_2$, —OH, —COR', —$CO_2R'$ or —CONR'R$^{11}$, wherein R' and R" are each independently hydrogen, $C_1$-$C_6$ alkyl or heteroalkyl.

Preferably, when $Z^1$ is N and $Z^2$ is C, $R^6$ is a monosubstituent —$CF_3$ at a 5-position of a pyridine ring, and a general formula of the compound is shown in formula (a):

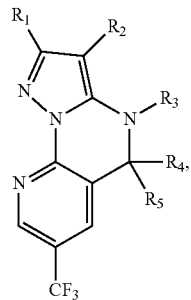

(a)

wherein $R^3$ is hydrogen, methyl or chloromethyl; $R^4$ and $R^5$ are each independently hydrogen, halogen, —CN, —$COR^7$, —$CO_2R^7$, —$CH_2COR^7$, —$CH_2COOR^7$, amino, alkyl, heteroalkyl, aryl or heteroaryl; wherein the amino, the alkyl, the aryl or the heteroaryl is unsubstituted or substituted with one or more substituents $R^9$;

or, when $Z^2$ is N and $Z^1$ is C, $R^6$ is a monosubstituent chlorine at a 5-position of the pyridine ring, and a general formula of the compound is shown in formula (b):

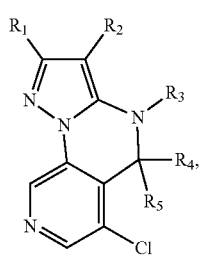

(b)

wherein $R^3$ is hydrogen, methyl or chloromethyl; $R^4$ and $R^5$ are each independently hydrogen, halogen, —CN, —$COR^7$, —$CO_2R^7$, —$CH_2COR^7$, —$CH_2COOR^7$, amino, alkyl, heteroalkyl, aryl or heteroaryl; wherein the amino, the alkyl, the aryl or the heteroaryl is unsubstituted or substituted with one or more substituents $R^9$;

or, when $Z^1$ and $Z^2$ are both C, and $R^6$ is disubstituents at a 3-position and a 5-position of a benzene ring, a general formula of the compound is shown in formula (c):

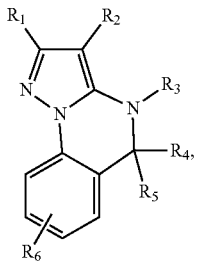

(c)

wherein $R^1$ is —CN or —$CF_3$, and $R^2$ is —CN, —$CF_3$, —$OCF_3$, —$SOCF_3$ or —$SOCH_2CH_3$; $R^3$ is hydrogen, —$CH_3$, —Ac or —$CH_2CH_2Cl$; a substituent of $R^6$ at the 3-position of the benzene ring is —Cl, —Br, —$CF_3$, —$CH_3$, —CN, —$CO_2CH_3$ or —$NO_2$, and a substituent of $R^6$ at the 5-position of the benzene ring is —Cl, —CF$_3$, —OCF$_3$ or —NO$_2$; R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$;

or, when Z$^1$ and Z$^2$ are both C, R$^6$ is disubstituents at a 4-position and a 6-position of the benzene ring, and R$^3$ is hydrogen, the general formula of the compound is shown in formula (d):

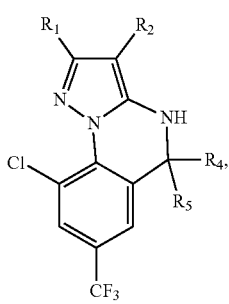

(d)

wherein R$^1$ is —CN, —CF$_3$, —COCH$_3$ or —CH$_2$NH$_2$, and R$^2$ is —OCF$_3$, —CF$_3$, —CN, —SOCF$_3$, —SOCH$_3$, —SOCH$_2$CH$_3$, —SOPh, —SOCH$_2$Ph, —SOC$_6$H$_{13}$,

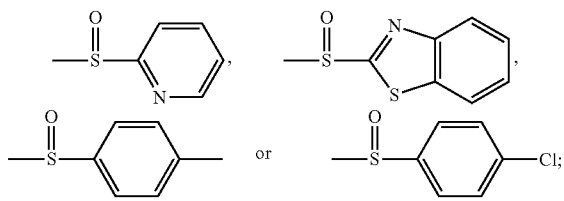

R$^6$ is —Cl or —CF$_3$; R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$;

or, when Z$^1$ and Z$^2$ are both C, R$^6$ is disubstituents at the 3-position and the 6-position, or at the 3-position and the 4-position, or at the 4-position and the 5-position, or at the 5-position and the 6-position of the benzene ring, and R$^3$ is hydrogen, the general formula of the compound is shown in formula (e):

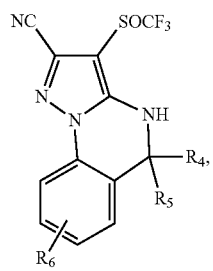

(e)

wherein R$^1$ is —CN, and R$^2$ is —SOCF$_3$; R$^6$ is —Cl or —CF$_3$; R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$; and R$^4$ and R$^5$ are not hydrogen at the same time.

Preferably, R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein R$^7$ is hydrogen, halogen, hydroxyl, C$_{1-4}$ alkyl, C$_{1-4}$ haloalkyl, C$_{1-4}$ alkenyl, C$_{1-4}$ haloalkenyl, amino or substituted amino.

Preferably, when the compound is shown in the formula (a) or the formula (b), and any one of R$^4$ and R$^5$ is hydrogen, R$^1$ is —CN, and R$^2$ is —SOCF$_3$ or —OCF$_3$; or R$^1$ is —CF$_3$, and R$^2$ is —SOCF$_3$;

or, when neither R$^4$ nor R$^5$ is hydrogen, R$^1$ is —CN or —CF$_3$; and R$^2$ is —SOCF$_3$, —SOCH$_2$CH$_3$, —OCF$_3$, —CF$_3$, —CN or halogen.

Preferably, when the compound is shown in the formula (c), R$^3$ is —CH$_3$, —Ac or —CH$_2$CH$_2$Cl, R$^2$ is —SOCF$_3$, R$^1$ is —CN, and both R$^4$ and R$^5$ are —CO$_2$Me;

or, when R$^3$ is hydrogen, R$^2$ is —SOCF$_3$, and R$^1$ is —COCH$_3$ or —CH$_2$NH$_2$, R$^4$ and R$^5$ are independently —CO$_2$Me or —CO$_2$CH$_2$Me;

or, when R$^3$ is hydrogen, and R$^2$ is —OCF$_3$ or —SOCF$_3$, R$^1$ is —CN or —CF$_3$, R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$.

Preferably, when the compound is shown in the formula (d), R$^3$ is hydrogen, and R$^2$ is —CN, —CF$_3$, —SOPh, —SOCH$_2$Ph, —SOC$_6$H$_{13}$,

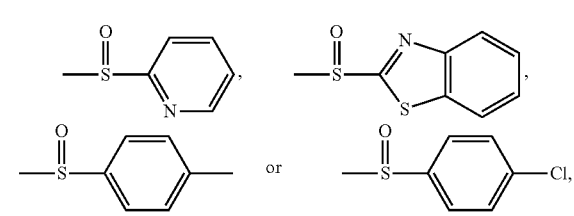

R$^1$ is —CN, and R$^4$ and R$^5$ are independently —CO$_2$Me or —CO$_2$CH$_2$Me;

or, when R$^3$ is hydrogen, R$^2$ is —SOCF$_3$, and R$^1$ is —COCH$_3$ or —CH$_2$NH$_2$, R$^4$ and R$^5$ are independently —CO$_2$Me or —CO$_2$CH$_2$Me;

or, when R$^3$ is hydrogen, and R$^2$ is —OCF$_3$ or —SOCF$_3$, R$^1$ is —CN or —CF$_3$, R$^4$ and R$^5$ are independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$.

Preferably, when the compound is shown in the formula (e), R$^6$ is 3-Cl and 6-CF$_3$, 3-Cl and 4-CF$_3$, 4-Cl and 5-CF$_3$, or 5-Cl and 6-CF$_3$ on the benzene ring; and R$^4$ and R$^5$ are each independently —CO$_2$Me, —CH$_2$CO$_2$Me, —CO$_2$Et, —CH$_2$CO$_2$Et, —CH$_2$CO$_2$CH$_2$CF$_3$ or —CH$_2$CO$_2$CH$_2$CHF$_2$.

An agricultural composition includes:

(a) 0.001 to 99.99% by weight of the compound above, or the optical isomer, the cis and trans isomers or the agromedically acceptable salt thereof, or a combination thereof; and (b) an agromedically acceptable carrier and/or excipient.

A method of using the agricultural composition according to the present invention in preparing an insecticide for killing or preventing agroforestry pests, sanitary insect pests and pests harmful to animal health.

A specific method of using is that the insecticide is directly applied to the pests or places contacted by the pests (for example, plants suffering from or probably suffering from pest damages, soil or environment therearound).

Compared with the prior art, the present invention has the following beneficial effects.

The present invention discloses the fused heterocyclic compounds with a new structure and the pyrazole-ring-containing fused heterocyclic compound. The fused heterocyclic compound and the pyrazole-ring-containing fused heterocyclic compound, and the optical isomer, cis and trans isomers or the agromedically acceptable salt thereof have high killing activity on agroforestry pests and sanitary insect pests and the like, and the compound according to the present invention has a delayed effect on pests such as *Solenopsis invicta* and the like, which enables the pests to carry the compound to a nest, thereby having a better killing effect on the whole *Solenopsis invicta* nest and a queen *Solenopsis invicta*. The compound according to the present invention has a good application prospect in pest control. The compound according to the present invention has lower toxicity to environmental organisms such as bees, *Bombyx mori* L. and the like, thus having a good application prospect.

DETAILED DESCRIPTION

The inventor of the present invention designs, synthesizes and screens a new fused heterocyclic compound and a pyrazole-ring-containing fused heterocyclic compound based on the problems of increasingly serious resistance and harmness to the environment and the like of the existing heterocyclic pesticides upon long-term and in-depth research. An insecticidal activity of the compound is obviously improved, and the compound has an expanded insecticidal spectrum. The present invention is further illustrated hereinafter with reference to the specific embodiments, but the embodiments are not intended to limit the present invention in any form. Unless otherwise specified, all the reagents and methods involved in the embodiments are frequently-used reagents and methods in the field.

In the present invention, unless otherwise specified in the context, meanings expressed by words, phrases and symbols to be used below are regulated as follows. The meanings of the following abbreviations and terms are used throughout the text.

The term "halogen" refers to fluorine, chlorine, bromine and iodine, and the term "halogen" in front of a group name refers to that the group is partially or completely halogenated, i.e., the group is substituted by F, Cl, Br or I in any combination, for example, monofluorodichloromethyl, difluoromethyl, trichloromethyl, pentafluoroethyl, or similar groups.

The term "alkyl" refers to hydrocarbyl, and the hydrocarbyl is selected from a saturated linear-chain or branched-chain hydrocarbyl. The alkyl preferably includes 1 to 12 carbon atoms, and more preferably includes 1 to 6 carbon atoms, such as methyl, ethyl, n-propyl, isopropyl, n-butyl, isobutyl, sec-butyl, tert-butyl, or similar groups.

The term "alkenyl" refers to a hydrocarbyl selected from a linear-chain or a branched-chain, and includes at least one C=C double bond. The alkenyl preferably includes 2 to 12 carbon atoms, and more preferably includes 2 to 6 carbon atoms, such as vinyl, prop-1-alkenyl, prop-2-alkenyl, 2-methylprop-1-alkenyl, buta-1,3-dialkylene, 2-methyl-1,3-butadiene, hex-1,3-dialkylene, or similar groups.

The term "cycloalkyl" refers to be selected from to a saturated cyclohydrocarbyl, and includes a monocyclic or polycyclic group. The cycloalkyl preferably has 3 to 12 carbon atoms. For example, the cycloalkyl may be a monocyclic group having 3 to 12 carbon atoms, such as cyclopropyl, cyclobutyl, cyclopentyl, cyclononyl, cyclodecyl, cycloundecyl and cyclododecyl, or similar groups. The cycloalkyl may also be a bicyclic group having 4 to 12 carbon atoms, such as a bicyclic group in [4,5], [5,5], [5,6] and [6,6] ring systems, a bridged bicyclic group selected from bicyclic[2.2.1]heptane, bicyclic[2.2.2]octane and bicyclic[3.2.2]nonane, or similar groups.

The term "cycloalkenyl" refers to be selected from an unsaturated cyclohydrocarbyl, and contains at least one C=C double bond, but is not completely conjugated, and the cycloalkenyl does not belong to an aromatic series (the aromatic series as defined herein), and includes a monocyclic or polycyclic group. The cycloalkenyl preferably has 3 to 12 carbon atoms, such as cyclopentene, cyclopentadiene, cyclohexene, cyclohexadiene, cycloheptene, cyclooctene, and cyclopentadiene, or similar groups.

The term "aryl" refers to be selected from the groups as follows: (a) 5 membered and 6 membered carbocyclic aromatic rings, such as phenyl, furan ring or thiophene ring; (b) bicyclic systems such as 7 to 12 membered bicyclic systems, wherein at least one ring is a carboatomic ring and an aromatic ring, such as naphthalene or 1,2,3,4-tetrahydroquinoline; (c) tricyclic systems, such as a 10 to 15 membered tricyclic systems, wherein at least one ring is a carboatomic ring and an aromatic ring, such as fluorene.

For example, the aryl is selected from 5-membered and 6-membered carbocyclic aromatic rings, wherein the carbocyclic aromatic ring is fused to 5 to 7 membered cycloalkyl or a heterocycle optionally containing at least one heteroatom selected from N, O and S, under the conditions that a connection point is on the carbocyclic aromatic ring when the carbocyclic aromatic ring is fused to the heterocycle, and the connection point may be on the carbocyclic aromatic ring or on the cycloalkyl when the carbocyclic aromatic ring is fused to the cycloalkyl. A divalent group formed from a substituted benzene derivative and having a free valence on a ring atom is called a substituted phenylene group. A divalent group derived from a monovalent polycyclic hydrocarbon with a name ended with "yl" by removing a hydrogen atom from a carbon atom having a free valence is named by adding "subunit" to the name of the corresponding monovalent group, for example, a naphthyl having two connection points is called a naphthylene. However, the aryl does not include heterocyclyl or overlaps with heteroaryl, which are defined separately below. Therefore, if one or more carbocyclic aromatic rings are fused with a heterocyclic aromatic ring, a resulting ring system is the heteroaryl as defined herein, rather than the aryl.

The term "heteroalkyl" refers to an alkyl including at least one heteroatom, and the heteroatom refers to a non-C atom. The heteroatom is preferably N, O, S, P or Se, etc.

The term "heteroaryl" refers to be selected from the groups as follows:

5 to 7 membered aromatic monocyclic ring containing 1, 2, 3 or 4 heteroatoms selected from N, O and S, and the rest ring atoms being carbon;

8 to 12 membered bicyclic ring containing 1, 2, 3 or 4 heteroatoms selected from N, O and S, the remaining ring atoms being carbon, and wherein at least one ring is aromatic and at least one heteroatom is present in the aromatic ring;

11 to 14 membered bicyclic ring containing 1, 2, 3 or 4 heteroatoms selected from N, O and S, the remaining ring atoms being carbon, and wherein at least one ring is aromatic and at least one heteroatom is present in the aromatic ring;

For example, the heteroaryl includes a 5 to 7 membered heterocyclic aromatic ring fused to a 5 to 7 membered cycloalkyl ring. For the fused bicyclic heteroaryl ring system, only one ring therein contains at least one heteroatom, and a connection point may be located on the heterocyclic aromatic ring or the cycloalkyl ring.

When a total number of S and O atoms in the heteroaryl exceeds 1, these heteroatoms are not adjacent to each other.

The term "heterocyclyl" refers to be selected from the rings as follows: saturated and partially unsaturated rings of 4 to 12 membered monocyclic, bicyclic and tricyclic rings, which contain at least one carbon atom in addition to 1, 2, 3 or 4 heteroatoms selected from oxygen, sulfur and nitrogen. The term "heterocyclyl" also refers to an aliphatic spiro ring containing at least one heteroatom selected from N, O and S under the condition that a connection point is located on a heterocycle. The ring may be saturated or contain at least one double bond. The heterocycle may be oxidatively substituted. A connection point may be a carbon atom or a heteroatom in the heterocycle.

The term "alkoxy" refers to a hydrocarbonoxy selected from saturated linear or branched hydrocarbonoxy. The alkoxy includes 1 to 12 carbon atoms, and preferably includes 1 to 6 carbon atoms, such as methoxyl, ethoxy, n-propoxy, isopropoxy, n-butoxy, isobutoxy, sec-butoxy, tert-butoxy, or similar groups.

The substituents are selected from halogen, —R'''', —OR'''', =, =NR'''', =N—OR''''—, —NR''''R'''', SR'''', —OC(O)R'''', —C(O)R'''', —NR''''—SO$_2$NR'''', —NR''''CO$_2$R''''—NH—C(NH$_2$)=NH, —NR''''C(NH$_2$)=NH, —NH—C(NH$_2$)=NR'''', —S(O)R'''', —SO$_2$R'''', —SO$_2$NR''''R'''', —NR''''SO$_2$R'''', —CN and —NO$_2$, —CH(Ph)$_2$, halogenated (C$_1$-C$_4$) alkoxy and halogenated (C$_1$-C$_4$)alkyl. A number of the substituents ranges from 0 to 3, and preferably, 0, 1 or 2 substituents are provided. R'''' and R'''' are independently selected from hydrogen, unsubstituted (C$_1$-C$_6$) alkyl and heteroalkyl, unsubstituted aryl, aryl substituted with 1 to 3 halogens, unsubstituted alkyl, alkoxy or thioalkoxy, or aryl-(C$_1$-C$_4$) alkyl. When being connected to the same nitrogen atom, R'''' and R'''' can combine with the nitrogen atom to form a 5, 6 or 7 membered ring. Therefore, —NR''''R'''' includes 1-pyrrolidinyl and 4-morpholinyl. The "alkyl" includes, for example, trihaloalkyl (e.g., —CF$_3$ and —CH$_2$CF$_3$).

Preferably, the substituents are selected from halogen, —R'''', —OR'''', =O, —NR''''R'''', —SR'''', —OC(O)R'''', —C(O)R'''', —CO$_2$R'''', —CONR''''R'''', —OC(O)NR''''R'''', —NR''''C(O)R'''', —NR''''CO$_2$R'''', —S(O)R'''', —SO$_2$R'''', —SO$_2$NR''''R'''', —NR''''SO$_2$R'''41 '' —CN and —NO$_2$, halogenated (C$_1$-C$_4$) alkoxy and halogenated (C$_1$-C$_4$) alkyl, wherein R'''' and R'''' are defined as above.

The term "fused heterocycle" herein refers to a following cyclic system, such as a bicyclic or tricyclic system, in which two rings share only two ring atoms and one bond, and the ring atoms thereof contain at least one non-C atom. Examples of the fused heterocycle may include fused bi-heterocycloalkyl, such as bi-heterocycles selected from the above [4,4], [4,5], [5,5], [5,6] and [6,6] ring systems composed by arrangement of 7 to 12 ring atoms; fused bicyclic heteroaryl rings, such as the 8 to 12 membered bicyclic heteroaryl rings described above; fused tricyclic heteroaryl rings, such as the 11 to 14 membered tricyclic heteroaryl rings described above, for example, pyrazolo[1,5-a]quinazoline, pyrazolo[1,5-c]quinazoline, pyrrolo[1,2-a]quinazoline, pyrazolo[1,5-a]pyrido[3,2-e]pyrimidine, pyrazolo[1,5-a]pyrido[3,4-e]pyrimidine, pyrazolo[1,5-a]pyrido[2,3-e]pyrimidine, and pyrazolo[1,5-a]pyrido[4,3-e]pyrimidine, etc.; and the fused bicyclic or tricyclic heterocyclic rings.

The compound may contain an asymmetric center, and thus may exist as an enantiomer. When the compound has two or more asymmetric centers, they may additionally exist as diastereomers. The enantiomers and the diastereomers belong to a broader category of stereomers. All these possible stereomers include substantially pure resolved enantiomers (meaning that a target stereomer contains no more than 10% by weight of any other stereomer), racemic mixtures thereof, and diastereomeric mixtures thereof. Unless otherwise stated, one of the mentioned isomers applies to any possible isomer. When isomer components are not specified, all possible isomers are included.

When the compound contains olefinic double bonds, these double bonds refer to geometric isomers containing E and Z, unless otherwise stated.

Some compounds may have different hydrogen connection points, which are called tautomers. For example, a compound containing a carbonyl-CH$_2$C(O)-group (keto form) may undergo tautomerism to form a hydroxyl-CH=C(OH)-group (enol form). During application, the compound also includes the keto form and enol form alone and mixtures thereof.

The term "acceptable salt" refers to a salt with known cations or aions, and may be applied to form use in the field.

Suitable salts with bases, for example, salts formed from compounds of formula (I) and formula (II) containing carboxyl groups, include salts of alkali metals (such as sodium and potassium), alkali earth metals (such as calcium and magnesium), ammonium and amines.

Suitable salts with acid radical additives, such as salts formed from compounds of formula (I) and formula (II) containing amino, include salts formed with inorganic acids such as hydrochloride, sulphate, sulphite, phosphate, hydrogen phosphate and nitrate, and salts formed with organic acids such as acetic acid, malic acid, tartaric acid, citric acid, lactic acid, salicylic acid, oxalic acid, etc.

Moreover, if the compound is obtained as an acid addition salt, free alkalis can be obtained by alkalizing a solution of the acid salt. In contrast, if a product is a free alkali, the addition salt can be prepared by dissolving the free alkali in a suitable organic solvent and treating the solution with an acid, which is consistent with a conventional process of preparing an acid addition salt from an alkaline compound. Those skilled in the art should understand various synthesis methods that can be used to prepare agromedically acceptable addition salts without undue experimentation.

The compound of the present invention can be used to control and kill various agroforestry pests, sanitary insect pests and pests harmful to animal health. In this specification, the "insecticide" is a general designation of substances that have the effect of preventing and controlling all the pests mentioned above. Examples of the pests include, but are not limited to: coleoptera insects such as *Sitophilus zeamais, Tribolium castaneum, Henosepilachna vigintioctomacta, Henosepilachna sparsa, Agrarius fusillis, Anomala cupripes, Popillia quadriguttata, Monolepta hieroglyphica, Monochamus alternatus, Echinocnemus squameus, Basiprionota bisignata, Anoplophora chinensis, Apripona germari, Soclytus schevy*, or *Agriotes fuscicollis*; lepidoptera insects such as *Lymantria dispar, Malacosoma neustria testacea, Diaphania perspectalis, Clania variegata, Cnidocampa flauescens, Dendrolimus punctatus, Orgyia antiqua, Paranthrene tabaniformis, Spodoptera litura, Chilo suppressalis, Ostrinia nubilalis, Ephestia cautella, Adoxophyes orana, Laspyresia splendana, Agrotis fucosa, Galleria mellonella, Plutella xylostella, Phyllocnistis citrella*, or *Mythimna separata*; hemiptera insects such as *Stephanitis nashi*; homoptera insects such as *Nephotettix cincticeps, Unaspis yanonensis, Myzus persicae, Aphis gossydii*, or *Bemisia tabaci*; orthoptera insects such as *Gryllotalpa africana*, or *Locus migratoria*; hymenoptera insects such as *Solenopsis invicta*, or *Tremex fuscicornis;* blattaria insects such as *Blattella germanica, Periplaneta american*, or *Copotermes formosamus*; diptera insects such as *Musca domestica, Aedes aegypti, Delia platura, Culex* sp., or *Anopheles sinensis*; and plant parasitic nematodes such as *Meloidogyne, Pratylenchus* spp., *Aphelenchoides besseyi Christie, Bursaphelenchus xylophilus*, etc. The pests harmful to animal health include *Boophilus microplus, Haemaphysalis longicornis, Hyalomma anatolicum, Hypoderma* spp., *Fasciola hepatica, Moniezia blanchard, Ostertagia* spp., *Trypanosoma enansi, Babesia bigemina*, etc.

The compound related to the present invention preferably has a high activity on agroforestry pests such as lepidoptera, hymenoptera, hemiptera, coleoptera, diptera and blattaria pests, as well as animal parasitic fleas and/or ticks and mites and sanitary insect pest, and more preferably has a high activity on piercing-sucking or chewing mouthpart pests.

Insecticide composition containing the active substances of the present invention The active substances of the present invention may be prepared into an insecticide composition by a conventional method. These active compounds may be combined into conventional preparations, such as solutions, emulsions, suspensions, powders, foams, pastes, granules, aerosols, natural and synthetic materials impregnated with the active substances, microcapsules in polymers, coating compounds for seeds, and preparations for use with firing units (such as smoking cartridges, smoking cans, and smoking pans), as well as ultra-low volume (ULV) Cloud mist and Warm mist preparations.

These preparations may be produced by known methods, for example, the active compounds are mixed with extenders, which are liquid or liquefied gas or solid diluents or carriers, and optionally surfactants, i.e., emulsifiers and/or dispersants and/or foam formers. For example, when water is used as the extender, organic solvents may also be used as auxiliaries.

It is basically suitable to use liquid solvents as the diluents or carriers, such as aromatic hydrocarbons, for example, xylene, toluene or alkyl naphthalene; chlorinated aromatic or chlorinated aliphatic hydrocarbons such as chlorobenzene, vinyl chloride or methylene chloride; aliphatic hydrocarbons such as cyclohexane, paraffin or mineral oil fractions; alcohols such as ethanol or glycol as well as ethers and lipids thereof; ketones such as acetone, methyl ethyl ketone, methyl isobutyl ketone or cyclohexanone; or polar solvents that are not frequently used such as dimethylformamide, dimethyl sulphoxide, and water. The liquefied gas diluents or carriers refer to liquids that will become gas at normal temperature and pressure, such as aerosol propellants, for example, halogenated hydrocarbons and butane, propane, nitrogen and carbon dioxide.

The solid carriers may be ground natural minerals such as kaolin, clay, tale, quartz, activated clay, montmorillonite, or diatomite, and ground synthetic minerals such as highly dispersed silicic acid, alumina, and silicates. The solid carriers for granules are crushed and graded natural zircon, such as calcite, marble, pumice, sepiolite and dolomite, as well as granules synthesized from inorganic and organic coarse powders, and organic materials such as granules of sawdust, coconut shells, corn cobs and tobacco stems, etc.

Non-ionic and anionic emulsifiers may be used as emulsifiers and/or foam formers, for example, polyoxyethylene-fatty acid esters, polyoxyethylene-fatty alcohol ethers, such as alkaryl polyethylene glycol ethers, alkyl sulfonic acid esters, alkyl sulfates, aryl sulfonic esters, and albumin hydrolysates. The dispersants include, for example, lignin sulfite lye and methylcelluloses.

Adhesives such as carboxymethyl cellulose and natural and synthetic polymers in the form of powders, granules or emulsions, such as Arabic gum, polyvinyl alcohol and polyvinyl acetate, may be used in the preparations. Colorants such as inorganic dyes, for example, iron oxide, cobalt oxide and Prussian blue; organic dyes, such as dichloro dyes or metal cyanine dyes; and trace nutrients such as salts of iron, manganese, boron, cop, cobalt, aluminum and zinc may be used.

These active compounds of the present invention may be mixed with other active compounds to prepare a mixture that can be present in commercial preparations or in use preparation forms prepared from these preparations. The other active compounds include, but are not limited to: insecticides, baits, fungicides, acaricides, nematicides, fungicides, growth control agents, and the like. The insecticides include, for example, phosphates, carbamates, pyrethroids, chlorinated hydrocarbons, benzamides, nereistoxin and substances produced by microorganisms, such as abamectin.

Furthermore, these active compounds of the present invention may also be mixed with synergists to prepare a mixture that can be present in commercial preparations or in use preparation forms prepared from these preparations. The synergist is a compound that enhances the effect of the active compounds. Since the active compounds have activity, it is not necessary to add the synergist.

These preparations generally contain 0.001 to 99.99% by weight, preferably 0.01 to 99.9% by weight, more preferably 0.05 to 90% by weight of the active compound of the present invention in the insecticide composition. Concentration of the active compounds in the use preparation form prepared from the commercial preparations may vary within a wide range. The concentrations of the active compounds in the use preparation forms may range from 0.0000001 to 100% (g/v), and may preferably be between 0.0001 and 1%.

The present invention will be described in further detail below with reference to the specific embodiments, and the specific embodiments are only used to explain the present invention and are not used to limit the scope of the present invention. The experimental methods used in the following embodiments are conventional unless otherwise specified. The materials and reagents used are commercially available materials and reagents unless otherwise specified.

SYNTHESIS EMBODIMENTS

Embodiment 1: Synthesis of Compounds A1 to A47 by Using a Method A

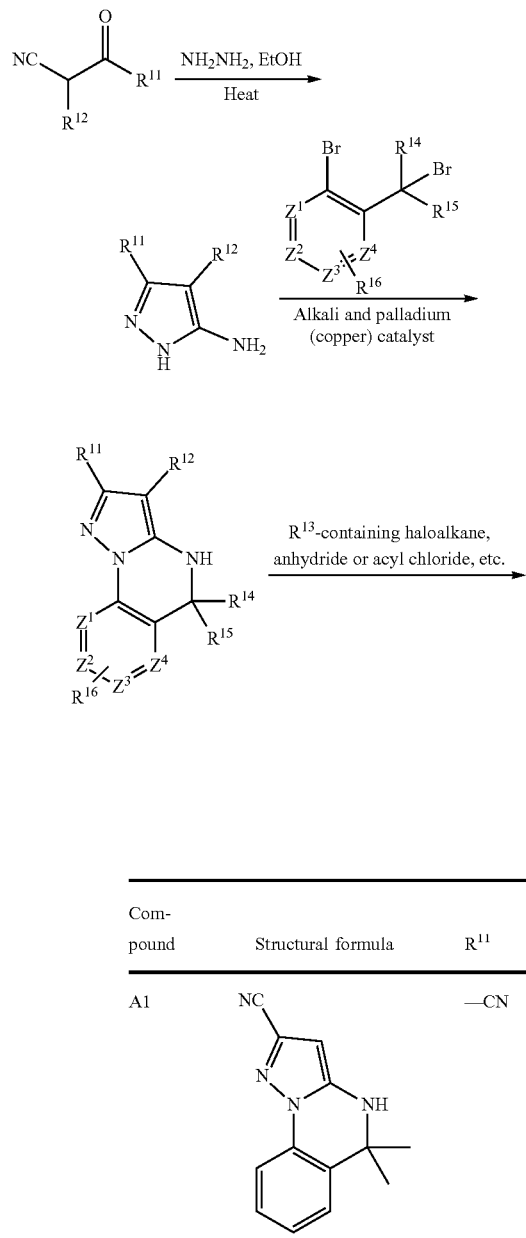

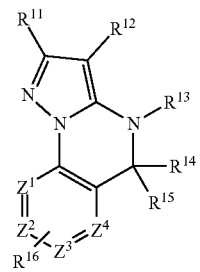

For instance, synthesis of a compound A1:

S1:5-amino-1H-pyrazole-3-cyano

Ethyl 2,3-dicyanopropionate (1.0 mmol) was added to 20.0 ml of ethanol and stirred vigorously, then hydrazine hydrate (2.0 mmol) was added to the reaction solution, heated and refluxed, then the heating was stopped after 3 hours, and the mixture was cooled to room temperature. The mixture was concentrated in vacuum and extracted with ethyl acetate and water, then the obtained ethyl acetate was concentrated and extracted in vacuum to obtain white solid 5-amino-1H-pyrazole-3-cyano, and the intermediate was directly used for next step without further purification.

S2:5,5-dimethyl-4,5-dihydropyrazole[1,5-α]quinazoline-2-cyano

Under the protection of nitrogen, a DMF mixture of 5-amino-H-pyrazole-3-cyano (1.0 mmol), 1-bromo-2-(1-bromo-1-methylethyl)benzene (1.0 mmol), cuprous iodide (0.2 mmol) and cesium carbonate (0.5 mmol) was stirred at 100° C. for 24 hours. The mixture was cooled to room temperature, and then filtered, and concentrated in vacuum, and the residues were purified by column chromatography to obtain the target compound 5,5-dimethyl-4,5-dihydropyrazole[1,5-α]quinazoline-2-cyano (yield of the two steps: 45%).

The compounds A2 to A47 were synthesized with reference to the method of the compound A1 (wherein cyclization steps also included similar cyclization methods mentioned in documents such as Tetrahedron Letters (2015) 56: 1367; WO2016046404, and WO2013174822), with a difference that different raw materials were selected for reaction according to different target compounds, or the compounds were derived from the synthesized target products. Specific compounds were as shown in Table 1:

TABLE 1

| Compound | Structural formula | $R^{11}$ | $R^{12}$ | $R^{13}$ | $R^{14}$ | $R^{15}$ | $R^{16}$ |
|---|---|---|---|---|---|---|---|
| A1 | | —CN | —H | —H | —CH$_3$ | —CH$_3$ | —H |

TABLE 1-continued

| Compound | Structural formula | R¹¹ | R¹² | R¹³ | R¹⁴ | R¹⁵ | R¹⁶ |
|---|---|---|---|---|---|---|---|
| A2 | | —CN | —Br | —H | —CH₃ | —CH₃ | —H |
| A3 | | —CN | —Br | —CH₃ | —CH₃ | —CH₃ | —H |
| A4 | | —CN | —Br | —Ac | —CH₃ | —CH₃ | —H |
| A5 | | —Ac | —Br | —H | —CH₃ | —CH₃ | —H |
| A6 | | —CONHCH₃ | —Br | —H | —CH₃ | —CH₃ | —H |

TABLE 1-continued

| Compound | Structural formula | $R^{11}$ | $R^{12}$ | $R^{13}$ | $R^{14}$ | $R^{15}$ | $R^{16}$ |
|---|---|---|---|---|---|---|---|
| A7 | | —CONC$_5$H$_{10}$ | —Br | —H | —CH$_3$ | —CH$_3$ | —H |
| A8 | | —CN | —SOCF$_3$ | —H | —CH$_3$ | —CH$_3$ | —H |
| A9 | | —CN | —SC$_2$H$_5$ | —H | —CH$_3$ | —CH$_3$ | —H |
| A10 | | —CF$_3$ | —H | —H | —CF$_3$ | —CF$_3$ | 5'-NH$_2$ |
| A11 | | —CF$_3$ | -Br | -H | —CF$_3$ | —CF$_3$ | 5'-NH$_2$ |

TABLE 1-continued

| Compound | Structural formula | R11 | R12 | R13 | R14 | R15 | R16 |
|---|---|---|---|---|---|---|---|
| A12 | | —CF₃ | -4 fluorophenyl | —H | —CF₃ | —CF₃ | 5'-NH₂ |
| A13 | | —CF₃ | —SCF₃ | —H | —CF₃ | —CF₃ | 5'-NH₂ |
| A14 | | —CF₃ | —SOC₂H₅ | —H | —CF₃ | —CF₃ | 5'-NH₂ |
| A15 | | —CN | —NH₂ | —H | —CH₃ | —CH₃ | —H |
| A16 | | —CN | —NHC₄H₉ | —H | —CH₃ | —CH₃ | —H |

TABLE 1-continued

| Compound | Structural formula | R¹¹ | R¹² | R¹³ | R¹⁴ | R¹⁵ | R¹⁶ |
|---|---|---|---|---|---|---|---|
| A17 | | —CN | —NHCOCH₃ | —H | —CH₃ | —CH₃ | —H |
| A18 | | —CN | —NHCO₂Ph | —H | —CH₃ | —CH₃ | —H |
| A19 | | —CN | —NHCONHCH₃ | —H | —CH₃ | —CH₃ | —H |
| A20 | | —CN | —NHSO₂Ph-4CH₃ | —H | —CH₃ | —CH₃ | —H |
| A21 | | —CN | —NO₂ | —H | —CH₃ | —CH₃ | —H |
| A22 | | —H | —CN | —H | —CH₂NH₂ | —F | 5-Cl |

TABLE 1-continued

| Compound | Structural formula | $R^{11}$ | $R^{12}$ | $R^{13}$ | $R^{14}$ | $R^{15}$ | $R^{16}$ |
|---|---|---|---|---|---|---|---|
| A23 | | —H | —CN | —H | —CH$_2$NH$_2$ | —NH$_2$ | 5-Cl |
| A24 | | —H | —CN | —H | —CH$_2$NHCH$_3$ | —NHCH$_3$ | 5-Cl |
| A25 | | —SCH$_3$ | —CN | —H | —CF$_3$ | —F | / |
| A26 | | —SOCH$_3$ | —CN | —H | —CF$_3$ | —F | / |
| A27 | | —SCH$_3$ | —COOEt | —H | —CF$_3$ | —F | / |

TABLE 1-continued

| Compound | Structural formula | R¹¹ | R¹² | R¹³ | R¹⁴ | R¹⁵ | R¹⁶ |
|---|---|---|---|---|---|---|---|
| A28 | | —SCH₃ | —CONH₂ | —H | —CF₃ | —F | / |
| A29 | | —SCH₃ | —CON(CH₃)₂ | —H | —CF₃ | —F | / |
| A30 | | —SCH₃ | —CON₂C₄CH₃ | —H | —CF₃ | —F | / |
| A31 | | —SCH₃ | —CN | —COOPh | —CF₃ | —F | / |
| A32 | | —SCH₃ | —CN | —CONHCH₃ | —CF₃ | —F | / |

TABLE 1-continued

| Compound | Structural formula | $R^{11}$ | $R^{12}$ | $R^{13}$ | $R^{14}$ | $R^{15}$ | $R^{16}$ |
|---|---|---|---|---|---|---|---|
| A33 | | —SCH$_3$ | —CN | —SO$_2$CH$_3$ | —CF$_3$ | —F | / |
| A34 | | —SCH$_3$ | —CN | —CH$_2$C$_2$H$_3$ | —CF$_3$ | —F | / |
| A35 | | —SCH$_3$ | —CN | —C$_2$H$_4$Br | —CF$_3$ | —F | / |
| A36 | | —NH$_2$ | —H | —H | CH$_2$CF$_3$ | —F | $Z^2$=N |
| A37 | | —NHC$_2$H$_5$ | —H | —H | —CH$_2$CF$_3$ | —F | $Z^2$=N |

TABLE 1-continued

| Compound | Structural formula | R11 | R12 | R13 | R14 | R15 | R16 |
|---|---|---|---|---|---|---|---|
| A38 | | —N(C2H5)CH2C2H3 | —H | —H | —CH2CF3 | —F | Z2=N |
| A39 | | —NHCOCH3 | —H | —H | —CH2CF3 | —F | Z2=N |
| A40 | | —NHCOOCH3 | —H | —H | —CH2CF3 | —F | Z2=N |
| A41 | | —NHCONHCH3 | —H | —H | —CH2CF3 | —F | Z2=N |
| A42 | | —NHSO2CH3 | —H | —H | —CH2CF3 | —F | Z2=N |

TABLE 1-continued

| Compound | Structural formula | $R^{11}$ | $R^{12}$ | $R^{13}$ | $R^{14}$ | $R^{15}$ | $R^{16}$ |
|---|---|---|---|---|---|---|---|
| A43 | | —NO$_2$ | —H | —H | —CH$_2$CF$_3$ | —F | $Z^2$=N |
| A44 | | —SCH$_3$ | —COOEt | —H | —CH$_3$ | —CH$_3$ | 4-F, $Z^2$=$Z^4$=N |
| A45 | | —SCH$_3$ | —SO$_2$Ph | —H | —CH$_3$ | —CH$_3$ | 4-F, $Z^2$=$Z^4$=N |
| A46 | | —SCH$_2$Ph | —CN | —H | —CH$_3$ | —CH$_3$ | 4-F, $Z^2$=$Z^4$=N |
| A47 | | —SO$_2$CH$_2$Ph | —CN | —H | —CH$_3$ | —CH$_3$ | 4-F, $Z^2$=$Z^4$=N |

Embodiment 2: Synthesis of Compounds B1 to B12 by Using a Method B

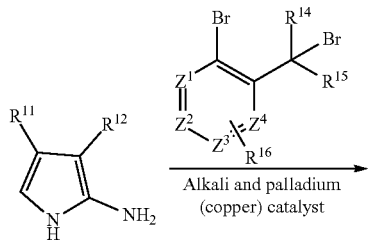

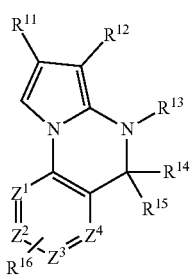

For instance, synthesis of a compound B1:

S1:2-amino-4-(4-methoxybenzene)-1H-pyrrole-3-cyano 2-bromo-1-(4-methoxyphenyl)-acetyl (1.0 mmol) was added to 15 ml of DMF, and then sodium azide (10.0 mmol) was added to the reaction solution. After the reaction mixture was stirred for 48 hours, the reaction mixture was filtered, and an obtained filtrate was extracted with ethyl ether for multiple times. Concentration in vacuum was performed, the residues were dissolved with methanol, and then 10% palladium carbon (0.2 mmol) was added thereto in a hydrogen atmosphere. The reaction mixture was stirred for 24 hours, and then filtered. An obtained filtrate was concentrated in vacuum, the residues were dissolved with tetrahydrofuran, and then acetic anhydride (2.0 mmol) and triethylamine (2.0 mmol) were added thereto. The reaction mixture was stirred for 5 hours, and then concentrated in vacuum, and the residues were purified by column chromatography to obtain N-(2-(4-methoxyphenyl)-2-ethoxy)-acetamide (yield: 78%).

N-(2-(4-methoxyphenyl)-2-ethoxy)-acetamide (1.0 mmol) was added to 15 ml of ethanol, and then malononitrile (2.0 mmol) and sodium ethoxide (1.5 mmol) were added thereto. The mixture was heated and refluxed for 12 hours, and then concentrated in vacuum, and the residues were purified by column chromatography to obtain the target compound (yield: 89%).

S2:2-bromo-2-(2-chloro-4-nitrophenyl)malononitrile

Under nitrogen protection, 2-chloro-4-nitro-benzoyl chloride (1.0 mmol) was dissolved in 10 ml of dry pyridine, cooled to 0° C., then trimethylsilylnitrile (1.1 mmol) was slowly added dropwise to the reaction solution, and the reaction solution was naturally heated to room temperature. After stirring for 10 hours, the reaction mixture was cooled to 0° C. again, and 2 ml of phosphorous oxybromide was added to the reaction mixture. After stirring for 12 hours, the solution was removed in vacuum, and the residues were extracted with water and ethyl acetate. Then the ethyl acetate was obtained by concentration and extraction in vacuum, and the residues were purified by column chromatography to obtain the 2-bromo-2-(2-chloro-4-nitrophenyl)malononitrile (yield: 56%).

S3:2-(4-methoxybenzene)-8-nitropyrrole[1,2-α]quinazoline-3,5,5(4H)-tricyano

Under the protection of nitrogen, a DMF mixture of 2-amino-4-(4-methoxybenzene)-1H-pyrrole-3-cyano (1.0 mmol), 2-bromo-2-(2-chloro-4-nitrophenyl)malononitrile (1.1 mmol), cuprous iodide (0.2 mmol) and sodium ethoxide (0.5 mmol) was stirred at 120° C. for 24 hours. The mixture was cooled to room temperature, and then filtered, and concentrated in vacuum, and the residues were purified by column chromatography to obtain the 2-(4-methoxybenzene)-8-nitropyrrole[1,2-α]quinazoline-3,5,5(4H)-tricyano (yield: 53%).

The compounds B2 to B12 were synthesized with reference to the method of the compound B1 (similar cyclization methods mentioned in documents such as Synthetic Communications (2015) 45: 2426; Tetrahedron (2014) 55: 4997; and WO2007149907), with a difference that different raw materials were selected for reaction according to different target compounds, and some compounds, such as compounds B9, B10, B11, B12, etc., could be obtained by modifying B7. Specific compounds were as shown in Table 2:

TABLE 2

| Compound | Structural formula | $R^{11}$ | $R^{12}$ | $R^{13}$ | $R^{14}$ | $R^{15}$ | $R^{16}$ |
|---|---|---|---|---|---|---|---|
| B1 | | 4-methoxyphenyl | —CN | —H | —CN | —CN | 5'-NO$_2$ |
| B2 | | 4-methoxyphenyl | —CN | —CH$_3$ | —CN | —CN | 5'-NO$_2$ |
| B3 | | 4-methoxyphenyl | —COCH$_3$ | —H | —CN | —CN | 5'-NO$_2$ |
| B4 | | 4-methoxyphenyl | —COCH$_3$ | —H | —CONH$_2$ | —CONH$_2$ | 5'-NO$_2$ |

TABLE 2-continued

| Compound | Structural formula | $R^{11}$ | $R^{12}$ | $R^{13}$ | $R^{14}$ | $R^{15}$ | $R^{16}$ |
| --- | --- | --- | --- | --- | --- | --- | --- |
| B5 | | Phenyl | —SO$_2$Ph | —H | —F | —F | 5'-Cl |
| B6 | | —CN | —CN | —H | —CN | —CN | 5'-NO$_2$ |
| B7 | | —CN | —CN | —H | —CN | —CN | 5'-NH$_2$ |
| B8 | | —CN | —CN | —H | —CN | —CN | 5'-NHCOC$_2$H$_3$ |
| B9 | | —CN | —CN | —H | —CN | —CN | 5'-Br |

TABLE 2-continued
| Compound | Structural formula | $R^{11}$ | $R^{12}$ | $R^{13}$ | $R^{14}$ | $R^{15}$ | $R^{16}$ |
|---|---|---|---|---|---|---|---|
| B10 | 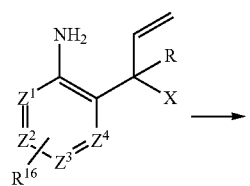 | —CN | —CN | —H | —CN | —CN | 5'-NHSO$_2$CH$_3$ |
| B11 | 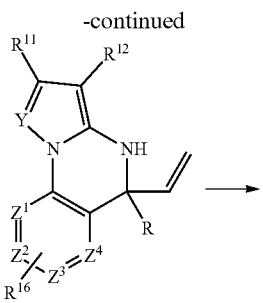 | —CN | —CN | —H | —CN | —CN | 5'-NHCOOCH$_3$ |
| B12 | 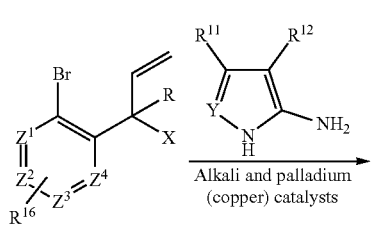 | —CN | —CN | —H | —CN | —CN | 5'-NHCONHCH$_3$ |
Embodiment 3: Synthesis of Compounds C1 to C64 by Using a Method C
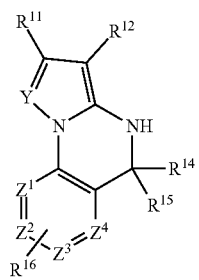
X is chlorine or bromine For instance, synthesis of a compound C1:

S1: (2-amino-3-chloro-5-(trifluoromethyl)phenyl)boric acid

Under the protection of nitrogen, 2-bromo-6-chloro-4-trifluoromethylaniline (1.0 mmol) was dissolved in 20 ml of dry tetrahydrofuran, and cooled to 0° C., then n-butyl lithium (2.5 mmol, 1.6 M n-hexane solution) was slowly added dropwise to the reaction mixture, and stirred for 2 hours. Trimethylchlorosilane (2.5 mmol) was slowly added dropwise to the reaction mixture for reaction, and then the reaction mixture was naturally heated and stirred for 12 hours, the solvent was removed by vacuum concentration, and the target compound (2-amino-3-chloro-5-(trifluoromethyl)phenyl)boric acid (yield: 87%) was obtained by reduced pressure distillation.

S2: 2-chloro-6-(1,2-dichloro-3-butene-2-yl)-4-(trifluoromethyl)phenylamine

Under the protection of nitrogen, a DMF mixture (3.0 ml) of 3-bromo-3,4-dichloro-1-butene (1.0 mmol), Pd(dppf)Cl₂ (0.15 mmol), sodium carbonate (0.15 mmol) and (2-amino-3-chloro-5-(trifluoromethyl)phenyl)boric acid (1.5 mmol) and water (0.5 ml) were stirred at 100° C. for 10 hours. After the solution was removed in vacuum, the residues were diluted with water (10 ml). Then a water layer was extracted with ethyl acetate, and the ethyl acetate was obtained by concentration and extraction in vacuum, and the residues were purified by column chromatography to obtain the target compound 2-chloro-6-(1,2-dichloro-3-butene-2-yl)-4-(trifluoromethyl)phenylamine (yield: 85%).

S3: 2-bromo-1-chloro-3-(1,2-dichloro-3-butene-2-yl)-5-(trifluoromethyl)phenyl Under the protection of nitrogen, 2-bromo-1-chloro-3-(1,2-dichloro-3-butene-2-yl)-5-(trifluoromethyl)phenyl (1.0 mmol) and cupric bromide (1.5 mmol) were dissolved in 10 ml of acetonitrile, cooled to −5° C., and then isoamyl nitrite (1.3 mmol) was slowly added thereto, and the reaction mixture was heated to 50° C. After three hours, the mixture was filtered, and the filtrate was concentrated in vacuum, and the residues were purified by column chromatography to obtain the target compound 2-bromo-1-chloro-3-(1,2-dichloro-3-butene-2-yl)-5-(trifluoromethyl)phenyl (yield: 91%).

S4: 9-chloro-7-trifluoromethylphenyl-5-chloromethyl-5-vinyl-4,5-dihydropyrrole[1,5-α]quinazoline-2-cyano Under the protection of nitrogen, a DMF mixture of 5-amino-1H-pyrazole-3-cyano (1.0 mmol), 2-bromo-1-chloro-3-(1,2-dichloro-3-butene-2-yl)-5-(trifluoromethyl)phenyl (1.1 mmol), cuprous iodide (0.2 mmol) and sodium ethoxide (0.5 mmol) was stirred at 120° C. for 24 hours. The mixture was cooled to room temperature, and then filtered. The filtrate was concentrated in vacuum, and the residues were purified by column chromatography to obtain the target compound 9-chloro-7-trifluoromethylphenyl-5-chloromethyl-5-vinyl-4,5-dihydropyrrole[1,5-α]quinazoline-2-cyano (yield: 52%).

The compounds C2 to C64 were synthesized with reference to the method of the compound C1 (similar cyclization methods were mentioned in documents such as WO2007144669), with a difference that different raw materials were selected for reaction according to different target compounds. Specific compounds were as shown in Table 3.

TABLE 3

| Compound | Structural formula | $R^{11}$ | $R^{12}$ | $R^{13}$ | $R^{14}$ | $R^{15}$ | $R^{16}$ |
| --- | --- | --- | --- | --- | --- | --- | --- |
| C1 | 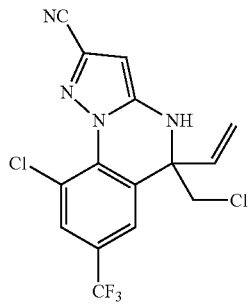 | —CN | —H | —H | —C₂H₃ | —CH₂Cl | 4'-CF₃, 6'-Cl |
| C2 | 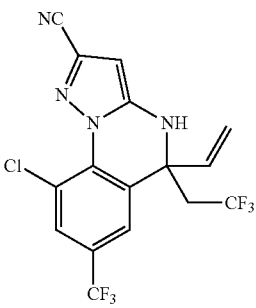 | —CN | —H | —H | —C₂H₃ | —CH₂CF₃ | 4'-CF₃, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C3 | | —CN | —H | —H | —C$_2$H$_3$ | —CF$_3$ | 4'-CF$_3$, 6'-Cl |
| C4 | | —CN | —H | —H | —C$_2$H$_3$ | —H | 4'-CF$_3$, 6'-Cl |
| C5 | | —CN | —Br | —H | —C$_2$H$_3$ | —CH$_2$Cl | 4'-CF$_3$, 6'-Cl |
| C6 | | —CN | —Br | —H | —C$_2$H$_3$ | —CH$_2$CF$_3$ | 4'-CF$_3$, 6'-Cl |
| C7 | | —CN | —Br | —H | —C$_2$H$_3$ | —CF$_3$ | 4'-CF$_3$, 6'-Cl |

TABLE 3-continued

| Compound | Structural formula | R[11] | R[12] | R[13] | R[14] | R[15] | R[16] |
|---|---|---|---|---|---|---|---|
| C8 | | —CN | —Br | —H | —C$_2$H$_3$ | —H | 4'-CF$_3$, 6'-Cl |
| C9 | | —CN | -6 trifluoro methylphenyl | [*]—H | —C$_2$H$_3$ | —CH$_2$Cl | 4'-CF$_3$, 6'-Cl |
| C10 | | —CN | -3-2,5-dimethyl furanyl | —H | —C$_2$H$_3$ | —CH$_2$Cl | 4'-CF$_3$, 6'-Cl |
| C11 | | —CN | -6 trifluoro methylphenyl | —H | —C$_2$H$_3$ | —CF$_3$ | 4'-CF$_3$, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C12 | | —CN | -3-2,5-dimethyl furanyl | —H | —C$_2$H$_3$ | —CF$_3$ | 4'-CF$_3$, 6'-Cl |
| C13 | | —CN | —SOCF$_3$ | —H | —C$_2$H$_3$ | —CH$_2$Cl | 4'-CF$_3$, 6'-Cl |
| C14 | | —CN | —SOCF$_3$ | —H | —C$_2$H$_3$ | —CH$_2$CF$_3$ | 4'-CF$_3$, 6'-Cl |
| C15 | | —CN | —SOCF$_3$ | —H | —C$_2$H$_3$ | —CF$_3$ | 4'-CF$_3$, 6'-Cl |

TABLE 3-continued

| Compound | Structural formula | R¹¹ | R¹² | R¹³ | R¹⁴ | R¹⁵ | R¹⁶ |
|---|---|---|---|---|---|---|---|
| C16 | | —CN | —SOCF$_3$ | —H | —C$_2$H$_3$ | —CH | 4'-CF$_3$, 6'-Cl |
| C17 | | —CN | —SOC$_2$H$_5$ | —H | —C$_2$H$_3$ | —CH$_2$Cl | 4'-CF$_3$, 6'-Cl |
| C18 | | —CN | —SOCH$_3$ | —H | —C$_2$H$_3$ | —CH$_2$Cl | 4'-CF$_3$, 6'-Cl |
| C19 | | —COCH$_3$ | —SOCH$_3$ | —H | —C$_2$H$_3$ | —CH$_2$Cl | 4'-CF$_3$, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C20 | | —CN | —SOCF$_3$ | —H | —C$_2$H$_3$ | —CH$_2$CN | 4'-CF$_3$, 6'-Cl |
| C21 | | —CN | —SOC$_2$H$_5$ | —H | —C$_2$H$_3$ | —CH$_2$CN | 4'-CF$_3$, 6'-Cl |
| C22 | | —CN | —SOCH$_3$ | —H | —C$_2$H$_3$ | —CH$_2$CN | 4'-CF$_3$, 6'-Cl |
| C23 | | —COCH3 | —SOC$_2$H$_5$ | —H | —C$_2$H$_3$ | —CH$_2$CN | 4'-CF$_3$, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C24 | | —CN | —SOCF$_3$ | —H | —CH$_2$CN | —CH$_2$OH | 4'-CF$_3$, 6'-Cl |
| C25 | | —CN | —SOC$_2$H$_5$ | —H | —CH$_2$CN | —CH$_2$OH | 4'-CF$_3$, 6'-Cl |
| C26 | | —CN | —SOCH$_3$ | —H | —CH$_2$CN | —CH$_2$OH | 4'-CF$_3$, 6'-Cl |
| C27 | | —COCH$_3$ | —SOCH$_3$ | —H | —CH$_2$CN | —CH$_2$OH | 4'-CF$_3$, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C28 | | —CN | —SOCF$_3$ | —H | —CH$_2$CN | —CH$_2$Br | 4'-CF$_3$, 6'-Cl |
| C29 | | —CN | —SOCF$_3$ | —H | —CH$_2$CN | —CH$_2$N(CH$_3$)$_2$ | 4'-CF$_3$, 6'-Cl |
| C30 | | —CN | —SOCF$_3$ | —H | —CH$_2$CN | —COOH | 4'-CF$_3$, 6'-Cl |
| C31 | | —CN | —SOCF$_3$ | —H | —CH$_2$CN | —COOMe | 4'-CF$_3$, 6'-Cl |

TABLE 3-continued

| Compound | Structural formula | R¹¹ | R¹² | R¹³ | R¹⁴ | R¹⁵ | R¹⁶ |
|---|---|---|---|---|---|---|---|
| C32 | | —CN | —SOCF₃ | —H | —CH₂CN | —CONH₂ | 4'-CF₃, 6'-Cl |
| C33 | | —CN | —SOCF₃ | —H | —CH₂CN | —CONHCH₃ | 4'-CF₃, 6'-Cl |
| C34 | | —CN | —SOCF₃ | —H | —CH₂CN | —CON₂C₄CH₃ | 4'-CF₃, 6'-Cl |
| C35 | | —CN | —SOCF₃ | —H | —CH₂COMe | —CONHCH₃ | 4'-CF₃, 6'-Cl |

TABLE 3-continued

| Compound | Structural formula | R11 | R12 | R13 | R14 | R15 | R16 |
|---|---|---|---|---|---|---|---|
| C36 | | —CN | —SOCF$_3$ | —H | —CH$_2$COOH | —COOH | 4'-CF$_3$, 6'-Cl |
| C37 | | —CN | —SOCF$_3$ | —H | —CH$_2$COOH | —COOMe | 4'-CF$_3$, 6'-Cl |
| C38 | | —CN | —SOCF$_3$ | —H | —CH$_2$COONH$_2$ | —COONH$_2$ | 4'-CF$_3$, 6'-Cl |
| C39 | | —CN | —SOCF$_3$ | —H | —CH$_2$COMe | —COOMe | 4'-CF$_3$, 6'-Cl |

TABLE 3-continued

| Compound | Structural formula | R¹¹ | R¹² | R¹³ | R¹⁴ | R¹⁵ | R¹⁶ |
|---|---|---|---|---|---|---|---|
| C40 | | —CN | —SOCF₃ | —COCH₃ | —CH₂COOMe | —COOMe | 4'-CF₃, 6'-Cl |
| C41 | | —COCH₃ | —SOCH₃ | —H | —CH₂CN | —CH₂Br | 4'-CF₃, 6'-Cl |
| C42 | | —COCH₃ | —SOCH₃ | H | —CH₂NHCH₃ | —CH₂CN | 4'-CF₃, 6'-Cl |
| C43 | | —COCH₃ | —SOCH₃ | H | —COOH | —CH₂CN | 4'-CF₃, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C44 | | —COCH$_3$ | —SOCH$_3$ | —H | —COOMe | —CH$_2$CN | 4'-CF$_3$, 6'-Cl |
| C45 | | —COCH$_3$ | —SOCH$_3$ | H | —CONHCH$_3$ | —CH$_2$CN | 4'-CF$_3$, 6'-Cl |
| C46 | | —COCH$_3$ | —SOCH$_3$ | —H | —CONHCH$_3$ | —CH$_2$COOMe | 4'-CF$_3$, 6'-Cl |
| C47 | | —COCH$_3$ | —SOCH$_3$ | —H | —COOH | —CH$_2$COOH | 4'-CF$_3$, 6'-Cl |

TABLE 3-continued

| Compound | Structural formula | R[11] | R[12] | R[13] | R[14] | R[15] | R[16] |
|---|---|---|---|---|---|---|---|
| C48 | | —COCH₃ | —SOCH₃ | —H | —COOME | —CH₂COOMe | 4'-CF₃, 6'-Cl |
| C49 | | —COCH₃ | —SOCH₃ | —H | —CONH₂ | —CH₂CONH₂ | 4'-CF₃, 6'-Cl |
| C50 | | —CN | -3-2,5-dimethyl furanyl | —H | —C₂H₃ | —H | 4'-CF₃, 6'-Cl |
| C51 | | —CN | —SOCF₃ | —H | —C₂H₃(OH)₂ | —H | 4'-CF₃, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C52 | | —CN | -3-2,5-dimethyl furanyl | —H | —$C_2H_3(OH)_2$ | —H | 4'-$CF_3$, 6'-Cl |
| C53 | | —CN | 6-trifluoro methylphenyl | —H | —$C_2H_3(OH)_2$ | —$CH_2Cl$ | 4'-$CF_3$, 6'-Cl |
| C54 | | —CN | -3-2,5-dimethyl furanyl | —H | —$C_2H_3(OH)_2$ | —$CF_3$ | 4'-$CF_3$, 6'-Cl |
| C55 | | —CN | —$SOCF_3$ | —H | —$C_2H_3(OH)_2$ | —$CH_2Cl$ | 4'-$CF_3$, 6'-Cl |

TABLE 3-continued

| Compound | Structural formula | R¹¹ | R¹² | R¹³ | R¹⁴ | R¹⁵ | R¹⁶ |
|---|---|---|---|---|---|---|---|
| C56 | | —CN | —SOCF₃ | H | —C₂H₃(OH)₂ | —CH₂CF₃ | 4'-CF₃, 6'-Cl |
| C57 | | —CN | —SOCF₃ | H | —C₂H₃(OH)₂ | —CF₃ | 4'-CF₃, 6'-Cl |
| C58 | | —CN | —SOCF₃ | —H | —CH₂CN | —C₂H₂COOMe | 4'-CF₃, 6'-Cl |
| C59 | | —CN | —SOC₂H₅ | —H | —CH₂CN | —C₂H₂COOMe | 4'-CF₃, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C60 | | —COCH$_3$ | —SOCH$_3$ | —H | —CH$_2$CN | —C$_2$H$_2$COOMe | 4'-CF$_3$, 6'-Cl |
| C61 | | —C$_2$H$_5$ | —Br | —H | —C$_2$H$_3$ | —C$_2$H$_3$ | 4'-CF$_3$, 6'-Cl |
| C62 | | —C$_2$H$_5$ | -3-2,5-dimethyl thienyl | —H | —C$_2$H$_3$ | —C$_2$H$_3$ | 4'-CF$_3$, 6'-Cl |
| C63 | | —C$_2$H$_5$ | —Br | —H | —C$_2$H$_2$COOMe | —C$_2$H$_2$COOMe | 4'-CF$_3$, 6'-Cl |

TABLE 3-continued

| Compound | Structural formula | $R^{11}$ | $R^{12}$ | $R^{13}$ | $R^{14}$ | $R^{15}$ | $R^{16}$ |
|---|---|---|---|---|---|---|---|
| C64 | (structure shown) | —$C_2H_5$ | -3-2,5-dimethyl thienyl | —H | —$C_2H_2$COOMe | —$C_2H_2$COOMe | 4'-$CF_3$, 6'-Cl |

TABLE 4

Hydrogen Spectrum and Mass Spectrum Data of Nuclear Magnetic Resonance of Some Compounds shown in Formula (I) of Table 1

| Compound | $^1$H-NMR(600 MHz) | MS (ESI) |
|---|---|---|
| A1 | $^1$H-NMR (600 MHz, CDCl$_3$) δ 7.73 (dd, J = 8.0, 1.4 Hz, 1H), 7.50-7.46 (m, 1H), 7.44-7.37 (m, 2H), 5.93 (s, 1H), 5.78 (Brs, 1H), 1.27(s, 3H), 1.25(s, 3H). | [M + H]$^+$ 225.1 |
| A2 | $^1$H-NMR (600 MHz, CDCl$_3$) δ 7.75 (dd, J = 8.0, 1.3 Hz, 1H), 7.56-7.51 (m, 1H), 7.48-7.45 (m, 2H), 5.86 (Brs, 1H), 1.28(s, 3H), 1.27(s, 3H). | [M + H]$^+$ 302.9 |
| A4 | $^1$H-NMR (600 MHz, CDCl$_3$) δ 7.75 (dd, J = 8.0, 1.3 Hz, 1H), 7.56-7.51 (m, 1H), 7.48-7.45 (m, 2H), 2.06 (s, 3H), 1.30(s, 3H), 1.29(s, 3H). | [M + H]$^+$ 345.1 |
| A5 | $^1$H-NMR (600 MHz, CDCl$_3$) δ 7.77 (dd, J = 8.0, 1.3 Hz, 1H), 7.57-7.53 (m, 1H), 7.49-7.47 (m, 2H), 2.16 (s, 3H), 1.28(s, 3H), 1.27(s, 3H). | [M + H]$^+$ 319.8 |
| A7 | $^1$H-NMR (600 MHz, CDCl$_3$) δ 7.77 (dd, J = 8.0, 1.3 Hz, 1H), 7.57-7.53 (m, 1H), 7.49-7.47 (m, 2H), 2.01-1.93 (m, 2H), 1.83-1.74 (m, 2H), 1.67-1.59 (m, 1H), 1.40-1.27 (m, 4H), 1.28(s, 3H), 1.27(s, 3H), 1.24-1.13 (m, 1H). | [M + H]$^+$ 389.3 |
| A8 | $^1$H-NMR (600 MHz, CDCl$_3$) δ 7.78 (dd, J = 8.0, 1.3 Hz, 1H), 7.58-7.54 (m, 1H), 7.50-7.48 (m, 2H), 5.86 (Brs, 1H), 1.28(s, 3H), 1.27(s, 3H). | [M + H]$^+$ 341.0 |
| A12 | $^1$H-NMR (600 MHz, CDCl$_3$) δ 7.40-7.38 (m, 2H), 7.35-7.33 (m, 2H), 7.12 (d, J = 8.0, 2H), 6.68-6.65 (m, 1H), 6.63-6.61 (m, 1H), 5.86 (Brs, 1H), 5.78 (s, 1H). | [M + H]$^+$ 485.4 |
| A15 | $^1$H-NMR (600 MHz, CDCl$_3$) δ 7.73 (dd, J = 8.0, 1.4 Hz, 1H), 7.50-7.46 (m, 1H), 7.44-7.37 (m, 2H), 6.26 (Brs, 2H), 5.78 (Brs, 1H), 1.27(s, 3H), 1.25(s, 3H). | [M + H]$^+$ 240.5 |
| A18 | $^1$H-NMR (600 MHz, CDCl$_3$) δ 9.25 (Brs, 1H), 7.73 (dd, J = 8.0, 1.4 Hz, 1H), 7.50-7.46 (m, 1H), 7.44-7.37 (m, 2H), 7.27-7.19 (m, 3H), 7.14-7.10 (m, 2H), 5.58 (Brs, 1H), 1.27(s, 3H), 1.25(s, 3H). | [M + H]$^+$ 359.9 |
| A19 | $^1$H-NMR (600 MHz, CDCl$_3$) δ 7.73 (dd, J = 8.0, 1.4 Hz, 1H), 7.50-7.46 (m, 1H), 7.44-7.37 (m, 2H), 6.06 (s, 1H), 5.78 (Brs, 1H), 2.78(s, 3H), 1.29(s, 3H), 1.28(s, 3H). | [M + H]$^+$ 297.4 |
| A21 | $^1$H-NMR (600 MHz, CDCl$_3$) δ 7.76 (dd, J = 8.0, 1.3 Hz, 1H), 7.56-7.51 (m, 1H), 7.49-7.47 (m, 2H), 5.93 (Brs, 1H), 1.29(s, 3H), 1.27(s, 3H). | [M + H]$^+$ 270.3 |
| A22 | $^1$H-NMR (600 MHz, CDCl$_3$) δ 8.30 (s, 1H), 8.17 (d, J = 7.6 Hz, 1H), 8.10-8.08 (m, 1H), 7.46 (d, J = 2.5 Hz, 1H), 5.21 (s, 1H), 4.78 (brs, 2H), 3.21-3.45(m, 2H). | [M + H]$^+$ 278.2 |
| A26 | $^1$H-NMR (600 MHz, CDCl$_3$) δ 7.78 (dd, J = 8.0, 1.3 Hz, 1H), 7.58-7.54 (m, 1H), 7.50-7.48 (m, 2H), 5.86 (Brs, 1H), 3.06 (s, 3H). | [M + H]$^+$ 345.1 |
| A27 | $^1$H-NMR (600 MHz, CDCl$_3$) δ 7.79 (dd, J = 8.0, 1.3 Hz, 1H), 7.57-7.54 (m, 1H), 7.49-7.48 (m, 2H), 5.5 (Brs, 1H), 4.38 (d, J = 7.3 Hz, 2H), 2.54 (s, 3H), 1.29 (t, J = 7.3 Hz, 3H). | [M + H]$^+$ 376.0 |
| A29 | $^1$H-NMR (600 MHz, CDCl$_3$) δ 7.79 (dd, J = 8.0, 1.3 Hz, 1H), 7.57-7.54 (m, 1H), 7.49-7.48 (m, 2H), 5.5 (Brs, 1H), 2.93 (s, 6H) 2.54 (s, 3H). | [M + H]$^+$ 375.1 |
| A33 | $^1$H-NMR (600 MHz, CDCl$_3$) δ 7.79 (dd, J = 8.0, 1.3 Hz, 1H), 7.57-7.54 (m, 1H), 7.49-7.48 (m, 2H), 5.5 (Brs, 1H), 3.35 (s, 3H) 2.56 (s, 3H). | [M + H]$^+$ 407.1 |
| A37 | $^1$H-NMR (600 MHz, CDCl$_3$) δ 8.40 (s, 1H), 7.50-7.46 (m, 1H), 7.44-7.37 (m, 1H), 6.56 (s, 1H), 5.78 (Brs, 1H), 4.56 (s, 1H), 4.38 (d, J = 7.3 Hz, 2H), 2.56-2.58(m, 2H), 1.29 (t, J = 7.3 Hz, 3H). | [M + H]$^+$ 316.1 |
| A43 | $^1$H-NMR (600 MHz, CDCl$_3$) δ 8.41 (s, 1H), 7.50-7.46 (m, 1H), 7.44-7.37 (m, 1H), 6.76 (s, 1H), 5.78 (Brs, 1H), 2.56-2.58(m, 2H). | [M + H]$^+$ 318.1 |
| A44 | $^1$H NMR (600 MHz, CDCl$_3$) δ 9.18 (s, 1H), 5.78 (Brs, 1H), 4.35 (d, J = 7.3 Hz, 2H), 2.54(s, 3H), 1.28 (t, J = 7.3 Hz, 3H), 1.27 (s, 3H), 1.26 (s, 3H). | [M + H]$^+$ 338.3 |
| A45 | $^1$H-NMR (600 MHz, CDCl$_3$) δ 9.18 (s, 1H), 7.44-7.37 (m, 2H), 7.27-7.19 (m, 3H), 5.78 (Brs, 1H), 2.54(s, 3H), 1.27 (s, 3H), 1.26 (s, 3H). | [M + H]$^+$ 405.1 |

TABLE 4-continued

Hydrogen Spectrum and Mass Spectrum Data of Nuclear Magnetic Resonance of Some Compounds shown in Formula (I) of Table 1

| Compound | $^1$H-NMR(600 MHz) | MS (ESI) |
|---|---|---|
| A46 | $^1$H-NMR (600 MHz, CDCl$_3$) δ 9.20 (s, 1H), 7.44-7.37 (m, 2H), 7.27-7.19 (m, 3H), 5.78 (Brs, 1H), 4.46-4.44 (m, 2H), 1.27 (s, 3H), 1.26 (s, 3H). | [M + H]$^+$ 367.0 |

TABLE 5

Hydrogen Spectrum and Mass Spectrum Data of Nuclear Magnetic Resonance of Some Compounds shown in Formula (I) of Table 2

| Compound | $^1$H-NMR (600 MHz) | MS (ESI) |
|---|---|---|
| B1 | $^1$H NMR (600 MHz, CDCl$_3$) δ 8.19 (d, J = 7.6 Hz, 1H), 8.11 (d, J = 8.0 Hz, 1H), 7.68 (d, J = 3.6 Hz, 2H), 7.48 (d, J = 2.6 Hz, 1H), 7.25 (s, 1H), 7.15 (d, J = 3.8 Hz, 2H), 5.40 (s, 1H), 3.86 (s, 3H). | [M + H]$^+$ 397.1 |
| B4 | $^1$H NMR (600 MHz, DMSO) δ 8.21 (d, J = 7.6 Hz, 1H), 8.15 (d, J = 8.0 Hz, 1H), 7.78 (d, J = 3.6 Hz, 2H), 7.53 (d, J = 2.6 Hz, 1H), 7.33 (s, 1H), 7.18 (d, J = 3.8 Hz, 2H), 6.67 (brs, 2H), 6.43 (brs, 2H), 5.44 (s, 1H), 3.89 (s, 3H), 2.59 (s, 3H). | [M + H]$^+$ 450.3 |
| B5 | $^1$H NMR (600 MHz, CDCl$_3$) δ 7.87 (d, J = 7.6 Hz, 2H), 7.69-7.68 (m, 1H), 7.68 (d, J = 3.6 Hz, 2H), 7.51-7.50 (m, 2H), 7.42-7.40 (m, 2H), 7.41-7.40 (m, 1H), 7.31-7.30 (m, 1H), 7.25 (s, 1H), 7.15-7.14 (m, 1H), 5.40 (s, 1H), 2.28 (s, 3H). | [M + H]$^+$ 469.9 |
| B6 | $^1$H NMR (600 MHz, CDCl$_3$) δ 8.18 (d, J = 7.6 Hz, 1H), 8.11 (d, J = 8.0 Hz, 1H), 7.48 (d, J = 2.6 Hz, 1H), 7.24 (s, 1H), 5.38 (s, 1H). | [M + H]$^+$ 316.2 |
| B7 | $^1$H NMR (600 MHz, CDCl$_3$) δ 8.18 (d, J = 7.6 Hz, 1H), 8.11 (d, J = 8.0 Hz, 1H), 7.48 (d, J = 2.6 Hz, 1H), 7.24 (s, 1H), 5.38 (s, 1H), 4.67 (brs, 2H). | [M + H]$^+$ 286.2 |
| B8 | $^1$H NMR (600 MHz, CDCl$_3$) δ 9.76(s, 1H), 8.17 (d, J = 7.6 Hz, 1H), 8.09 (d, J = 8.0 Hz, 1H), 7.49 (d, J = 2.6 Hz, 1H), 7.25 (s, 1H), 6.53-6.55 (m, 1H), 6.02 (dd, J = 8.0, 2.0 Hz, 1H), 5.86 (dd, J = 6.0, 2.0 Hz, 1H), 5.38 (s, 1H),. | [M + H]$^+$ 340.0 |
| B9 | $^1$H NMR (600 MHz, CDCl$_3$) δ 8.17 (d, J = 7.6 Hz, 1H), 8.10 (d, J = 7.9 Hz, 1H), 7.46 (d, J = 2.5 Hz, 1H), 7.24 (s, 1H), 5.21 (s, 1H). | [M + H]$^+$ 349.1 |

TABLE 6

Hydrogen Spectrum and Mass Spectrum Data of Nuclear Magnetic Resonance

| Compound | $^1$H-NMR(600 MHz) | MS (ESI) |
|---|---|---|
| C5 | $^1$H NMR (600 MHz, CDCl$_3$) δ 8.13 (s, 1H), 7.58 (s, 1H), 7.28 (s, 1H), 6.30-6.29 (m, 1H), 5.02-4.99 (m, 2H), 3.55-3.23 (m, 2H). | [M + H]$^+$ 450.9 |
| C6 | $^1$H NMR (600 MHz, CDCl$_3$) δ 8.14 (s, 1H), 7.56 (s, 1H), 7.17 (s, 1H), 6.30-6.29 (m, 1H), 5.02-4.99 (m, 2H), 2.81-2.79 (m, 2H). | [M + H]$^+$ 485.1 |
| C7 | $^1$H NMR (600 MHz, CDCl$_3$) δ 8.13 (s, 1H), 7.58 (s, 1H), 7.28 (s, 1H), 6.30-6.29 (m, 1H), 5.02-4.99 (m, 2H). | [M + H]$^+$ 470.9 |
| C8 | $^1$H NMR (600 MHz, CDCl$_3$) δ 8.13 (s, 1H), 7.58 (s, 1H), 7.28 (s, 1H), 6.30-6.29 (m, 1H), 5.02-4.99 (m, 2H), 4.65 (t, J = 3.6 Hz, 1H). | [M + H]$^+$ 402.9 |
| C9 | $^1$H NMR (600 MHz, CDCl$_3$) δ 8.13 (s, 1H), 7.72 (d, J = 7.6 Hz, 1H), 7.68 (d, J = 6.8 Hz, 1H), 7.51-7.49 (m, 2H), 7.58 (s, 1H), 7.28 (s, 1H), 6.30-6.29 (m, 1H), 5.02-4.99 (m, 2H), 3.55-3.23 (m, 2H). | [M + H]$^+$ 517.1 |
| C12 | $^1$H NMR (600 MHz, CDCl$_3$) δ 8.13 (s, 1H), 7.58 (s, 1H), 7.28 (s, 1H), 6.30-6.29 (m, 1H), 6.01 (s, 1H), 5.02-4.99 (m, 2H), 2.28 (s, 3H), 2.25 (s, 3H). | [M + H]$^+$ 487.0 |
| C15 | $^1$H NMR (600 MHz, CDCl$_3$) δ 8.15 (s, 1H), 7.58 (s, 1H), 7.16 (s, 1H), 6.30-6.29 (m, 1H), 5.02-4.99 (m, 2H). | [M + H]$^+$ 508.9 |
| C20 | $^1$H NMR (600 MHz, CDCl$_3$) δ 8.14 (s, 1H), 7.56 (s, 1H), 7.17 (s, 1H), 6.30-6.29 (m, 1H), 5.02-4.99 (m, 2H), 2.86-2.73 (m, 2H). | [M + H]$^+$ 480.0 |
| C24 | $^1$H NMR (600 MHz, CDCl$_3$) δ 8.14 (s, 1H), 7.56 (s, 1H), 7.11 (s, 1H), 4.56 (s, 1H), 2.86-2.73 (m, 2H), 2.64-2.53 (m, 2H). | [M + H]$^+$ 484.1 |
| C28 | $^1$H NMR (600 MHz, CDCl$_3$) δ 8.15 (s, 1H), 7.57 (s, 1H), 7.08 (s, 1H), 2.86-2.73 (m, 2H), 2.64-2.53 (m, 2H). | [M + H]$^+$ 545.9 |
| C30 | $^1$H NMR (600 MHz, CDCl$_3$) δ 10.20 (brs, 1H), 8.14 (s, 1H), 7.56 (s, 1H), 7.11 (s, 1H), 2.86-2.73 (m, 2H). | [M + H]$^+$ 497.9 |
| C31 | $^1$H NMR (600 MHz, CDCl$_3$) δ 8.14 (s, 1H), 7.56 (s, 1H), 7.11 (s, 1H), 3.68 (s, 3H), 2.86-2.73 (m, 2H). | [M + H]$^+$ 511.9 |
| C36 | $^1$H NMR (600 MHz, CDCl$_3$) δ 10.20 (brs, 1H), 9.86 (brs, 1H), 8.13 (s, 1H), 7.58 (s, 1H), 7.28 (s, 1H), 3.55-3.23 (m, 2H). | [M + H]$^+$ 516.9 |
| C37 | $^1$H NMR (600 MHz, CDCl$_3$) δ 8.13 (s, 1H), 7.58 (s, 1H), 7.28 (s, 1H), 3.82 (s, 3H), 3.66 (s, 3H), 3.55-3.23 (m, 2H). | [M + H]$^+$ 545.0 |
| C40 | $^1$H NMR (600 MHz, CDCl$_3$) δ 8.13 (s, 1H), 7.58 (s, 1H), 3.82 (s, 3H), 3.66 (s, 3H), 3.55-3.23 (m, 2H), 2.04 (s, 3H). | [M + H]$^+$ 587.0 |
| C54 | $^1$H NMR (600 MHz, CDCl$_3$) δ 8.13 (s, 1H), 7.58 (s, 1H), 7.18 (s, 1H), 6.03 (s, 1H), 4.06-4.04 (m, 1H) 3.81-3.56 (m, 2H), 3.78 (s, 1H), 3.44 (s, 1H), 2.82 (s, 3H), 2.66 (s, 3H),. | [M + H]$^+$ 521.0 |
| C59 | $^1$H NMR (600 MHz, CDCl$_3$) δ 8.13 (s, 1H), 7.58 (s, 1H), 7.48 (d, J = 6.4 Hz, 1H), 7.08 (s, 1H), 5.46 (dd, J = 6.4, 2.0 Hz, 1H), 3.77 (s, 3H), 3.55-3.23 (m, 2H), 3.30 (d, J = 7.0 Hz, 1H), 3.28-3.26 (m, 1H), 1.40 (t, J = 7.6 Hz, 3H). | [M + H]$^+$ 498.0 |
| C61 | $^1$H NMR (600 MHz, CDCl$_3$) δ 8.16 (s, 1H), 7.67 (s, 1H), 7.08 (s, 1H), 6.32-6.30 (m, 2H), 5.01-5.00 (m, 1H), 4.98-4.96 (m, 1H), 4.82-4.70 (m, 2H), 4.08 (dd, J = 8.6, 2.4 Hz, 2H), 1.25 (t, J = 8.6 Hz, 3H). | [M + H]$^+$ 432.0 |
| C62 | $^1$H NMR (600 MHz, CDCl$_3$) δ 8.16 (s, 1H), 7.67 (s, 1H), 7.08 (s, 1H), 6.68 (s, 1H), 6.32-6.30 (m, 2H), 5.01-5.00 (m, 1H), 4.98-4.96 (m, 1H), 4.82- | [M + H]$^+$ 464.1 |

TABLE 6-continued

Hydrogen Spectrum and Mass Spectrum Data of Nuclear Magnetic Resonance

| Compound | ¹H-NMR(600 MHz) | MS (ESI) |
|---|---|---|
|  | 4.70 (m, 2H), 4.08 (dd, J = 8.6, 2.4 Hz, 2H), 2.36 (s, 3H), 2.30 (s, 3H), 1.25 (t, J-8.6 Hz, 3H). | |
| C63 | ¹H NMR (600 MHz, CDCl₃) δ 8.16 (s, 1H), 7.67 (s, 1H), 7.08 (s, 1H), 6.32-6.30 (m, 2H), 5.01-5.00 (m, 1H), 4.98-4.96 (m, 1H), 4.08 (dd, J = 8.7, 2.4 Hz, 2H), 3.78 (s, 3H), 3.57 (s, 3H), 1.25 (t, J = 8.7 Hz, 3H). | [M + H]⁺ 548.0 |

Embodiment 4: Synthesis of Compounds a-1 to a-138 by Using a Method D

Method D:

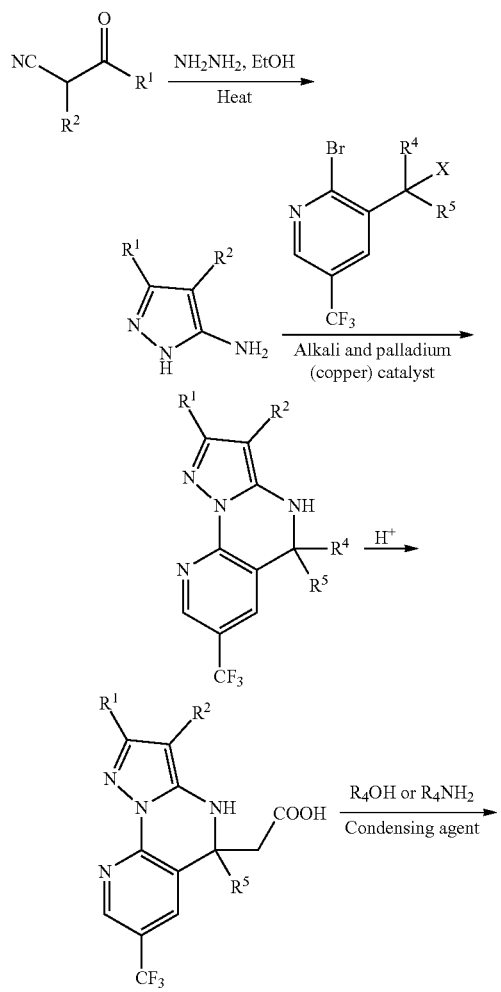

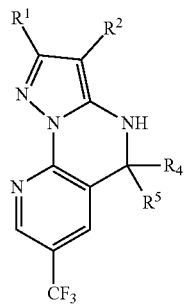

Taking a compound a-44 for example, a specific preparation process was as follows:

S1: 5-amino-1H-pyrazole-3-cyano

Ethyl 2,3-dicyanopropionate (1.0 mmol) was added to 20.0 mL of ethanol and stirred vigorously, then hydrazine hydrate (2.0 mmol) was added to the reaction solution, heated and refluxed, then the heating was stopped after 3 hours, and the mixture was cooled to room temperature. The mixture was concentrated in vacuum and extracted with ethyl acetate and water, then the obtained ethyl acetate was concentrated and extracted in vacuum to obtain white solid 5-amino-1H-pyrazole-3-cyano, and the intermediate was directly used for next step without further purification.

S2: 5,5-dichloro-7-trifluoromethyl-4,5-dihydropyrazole[1,5-α]quinazoline[3,2-e]pyridine-2-cyano Under the protection of nitrogen, a DMF mixture of 5-amino-1H-pyrazole-3-cyano (1.0 mmol), 2-bromo-3-(trichloromethyl)-5-trifluoromethylpyridine (1.0 mmol), cuprous iodide (0.2 mmol) and cesium carbonate (0.5 mmol) was stirred at 120° C. for 24 hours. The mixture was cooled to room temperature, and then filtered, and concentrated in vacuum, and the residues were purified by column chromatography to obtain the target compound 5,5-dichloro-7-trifluoromethyl-4,5-dihydropyrazole[1,5-α]quinazoline[3,2-e]pyridine-2-cyano (yield of the two steps: 25%).

S3: 5,5-dichloro-7-trifluoromethyl-3-trifluoromethylsulfinyl-4,5-dihydropyrazole[1,5-α]quinazoline[3,2-e]pyridine-2-cyano Under the protection of nitrogen, an anhydrous toluene mixture of 5,5-dichloro-7-trifluoromethyl-4,5-dihydropyrazole[1,5-α]quinazoline[3,2-e]pyridine-2-cyano (0.2 mmol), trifluoromethylsulfinyl chloride (0.5 mmol) and dimethylamine p-toluenesulfonate was stirred and heated at 100° C. for 24 hours. The mixture was cooled to room temperature, and then filtered, and concentrated in vacuum, and the residues were purified by column chromatography to obtain the target compound 5,5-dichloro-7-trifluoromethyl-3-trifluoromethylsulfinyl-4,5-dihydropyrazole[1,5-α]quinazoline[3,2-e]pyridine-2-cyano (yield: 77%).

The compounds a-1 to a-138 were synthesized with reference to the method of the compound a-44 (wherein cyclization steps also included similar cyclization methods mentioned in documents such as Tetrahedron Letters (2015) 56: 1367; WO2016046404, and WO2013174822), with a difference that different raw materials were selected for reaction according to different target compounds, or the compounds were derived from the synthesized target products through hydrolysis, simple esterification or amidation or reduction-oxidation. Specific compounds were as shown in Table 7.

TABLE 7

Compound Structure with a General Formula Shown in Formula (a)

| Structural formula | Compound | R¹ | R² | R³ | R⁴ | R⁵ | R⁶ |
|---|---|---|---|---|---|---|---|
| Formula (a) | a-1 | —CN | —SOCF₃ | H | —CO₂Me | —CH₂CO₂Me | 5-CF₃ |
| | a-2 | | | | | —CH₂CN | |
| | a-3 | | | | | —CH₂CONH₂ | |
| | a-4 | | | | | —CH₂CONHCH₃ | |
| | a-5 | | | | | —CH₂CH₂OH | |
| | a-6 | | | | | —CH(CO₂Me)CH₃ | |
| | a-7 | | | —CH₃ | | —CH₂CO₂Me | |
| | a-8 | | | —CH₂CH₂Cl | | —CH₂CO₂Me | |
| | a-9 | | | H | | —CH₂CO₂Et | |
| | a-10 | | | | | —CH₂CO₂CH₂CF₃ | |
| | a-11 | | | | | —CH₂CO₂CH₂CHF₂ | |
| | a-12 | | | | | —CH₂CO₂CH(CF₃)₂ | |
| | a-13 | | | | | —CH₂CO₂C(CH₃)₂CF₃ | |
| | a-14 | | | | | —CH₂CO₂C(CF₃)₂CH₃ | |
| | a-15 | | | | | —CH₂CO₂CH(CF₃)OCH₃ | |
| | a-16 | | | | | —CH₂Ph | |
| | a-17 | | | | | —CH₂COCH₃ | |
| | a-18 | | | | | —CH₂Br | |
| | a-19 | | | | | —CH₂CF₃ | |
| | a-20 | | | | | —CH₂COCF₃ | |
| | a-21 | | —SOCH₂CH₃ | | | —CH₂CO₂Me | |
| | a-22 | | —SOCF₃ | H | —CO₂Et | —CH₂CO₂Et | |
| | a-23 | | | | | —CH₂CO₂Me | |
| | a-24 | | | | | —CH₂CO₂CH₂CF₃ | |
| | a-25 | | | | —COCF₃ | —CH₂COCF₃ | |
| | a-26 | | | | | —CH₂COCH₃ | |
| | a-27 | | | | | —CH₂Ph | |
| | a-28 | | | | | —CH₂CO₂Me | |
| | a-29 | | | | | —CH₂Br | |
| | a-30 | | | | | —CH₂CN | |
| | a-31 | | | | | —CH₂CF₃ | |
| | a-32 | | | | —COCH₃ | —CH₂COCH₃ | |
| | a-33 | | | | | —CH₂CO₂Me | |
| | a-34 | | | | | —CH₂Br | |
| | a-35 | | | | | —CH₂CN | |
| | a-36 | | | | | —CH₂CF₃ | |
| | a-37 | | | | | —CH₂COCF₃ | |
| | a-38 | | | | —CONHMe | —CH₂COCH₃ | |
| | a-39 | | | | | —CH₂CO₂Me | |
| | a-40 | | | | | —CH₂Br | |
| | a-41 | | | | | —CH₂CF₃ | |
| | a-42 | | | | | —CH₂COCF₃ | |
| | a-43 | | | | —NHMe | —CH₂CN | |
| | a-44 | | | | —Cl | —Cl | |
| | a-45 | | | | | —CH₂Br | |
| | a-46 | | | | | —CH₂Cl | |
| | a-47 | | | | | —CH₂CN | |
| | a-48 | | | | | —CH₂CF₃ | |
| | a-49 | | | | —Br | —CH₂Cl | |
| | a-50 | | | | | —CH₂COCF₃ | |
| | a-51 | | | | —CH₃ | —CH₃ | |
| | a-52 | | | | —CN | —CN | |
| | a-53 | | | | | —CH₂CN | |
| | a-54 | | | | | —CH₂CF₃ | |
| | a-55 | | | | | —CH₂Cl | |
| | a-56 | | | | | —CH₂CO₂Me | |
| | a-57 | | | | | —CH₂COCF₃ | |
| | a-58 | | | | CF₃ | —CF₃ | |
| | a-59 | | | | | —CH₂CN | |
| | a-60 | | | | | —CH₂CF₃ | |
| | a-61 | | | | | —CH₂Cl | |
| | a-62 | | | | | —CH₂CO₂Me | |
| | a-63 | | | | | —CH₂COCF₃ | |
| | a-64 | | —CN | —SOCF₃ | H | H | —CO₂Me |
| | a-65 | | | | | —CH₂CO₂Me | |
| | a-66 | | | | | —CH(CO₂Me)CH₃ | |
| | a-67 | | | | | —CH₂CO₂CH₂CF₃ | |
| | a-68 | | | | | —CO₂CH₂CF₃ | |
| | a-69 | | | | | —CH₂CO₂CH(CF₃)₂ | |
| | a-70 | | | | | —CH₂COCF₃ | |
| | a-71 | | | | | —COCF₃ | |
| | a-72 | | | | | —CN | |
| | a-73 | | | | | —CH₂CN | |
| | a-74 | | | | | —CF₃ | |
| | a-75 | | | | | —CH₂CF₃ | |

TABLE 7-continued

Compound Structure with a General Formula Shown in Formula (a)

| Structural formula | Compound | R¹ | R² | R³ | R⁴ | R⁵ | R⁶ |
|---|---|---|---|---|---|---|---|
| | a-76 | | | | | —CONHMe | |
| | a-77 | | | | | —CH₂CONHCH₃ | |
| | a-78 | | | | | —CH₂COCH₃ | |
| | a-79 | | | | | —COCH₃ | |
| | a-80 | | | | | —Cl | |
| | a-81 | | | | | —Br | |
| | a-82 | | | | | —CH₂Cl | |
| | a-83 | | | | | —CH₂CH₂Cl | |
| | a-84 | | | | | —CHCHCl | |
| | a-85 | | | | | —CH(CH₃)₂ | |
| | a-86 | | | | | —CH=CHCH₃ | |
| | a-87 | —CF₃ | —SOCF₃ | H | H | —CO₂Me | |
| | a-88 | | | | | —CH₂CO₂Me | |
| | a-89 | | | | | —CH(CO₂Me)CH₃ | |
| | a-90 | | | | | —CH₂CO₂CH₂CF₃ | |
| | a-91 | | | | | —CO₂CH₂CF₃ | |
| | a-92 | | | | | —CH₂CO₂CH(CF₃)₂ | |
| | a-93 | | | | | —CH₂COCF₃ | |
| | a-94 | | | | | —COCF₃ | |
| | a-95 | | | | | —CN | |
| | a-96 | | | | | —CH₂CN | |
| | a-97 | | | | | —CF₃ | |
| | a-98 | | | | | —CH₂CF₃ | |
| | a-99 | | | | | —CONHMe | |
| | a-100 | | | | | —CH₂CONHCH₃ | |
| | a-101 | | | | | —CH₂COCH₃ | |
| | a-102 | | | | | —COCH₃ | |
| | a-103 | | | | | —Cl | |
| | a-104 | | | | | —Br | |
| | a-105 | | | | | —CH₂Cl | |
| | a-106 | | | | | —CH₂CH₂Cl | |
| | a-107 | | | | | —CHCHCl | |
| | a-108 | | | | | —CH(CH₃)₂ | |
| | a-109 | | | | | —CH=CHCH₃ | |
| | a-110 | —CN | —CCF₃ | H | H | —CO₂Me | |
| | a-111 | | | | | —CH₂CO₂Me | |
| | a-112 | | | | | —CH(CO₂Me)CH₃ | |
| | a-113 | | | | | —CH₂CO₂CH₂CF₃ | |
| | a-114 | | | | | —CO₂CH₂CF₃ | |
| | a-115 | | | | | —CH₂CO₂CH(CF₃)₂ | |
| | a-116 | | | | | —CH₂COCF₃ | |
| | a-117 | | | | | —COCF₃ | |
| | a-118 | | | | | —CN | |
| | a-119 | | | | | —CH₂CN | |
| | a-120 | | | | | —CF₃ | |
| | a-121 | | | | | —CH₂CF₃ | |
| | a-122 | | | | | —CONHMe | |
| | a-123 | | | | | —CH₂CONHCH₃ | |
| | a-124 | | | | | —CH₂COCH₃ | |
| | a-125 | | | | | —COCH₃ | |
| | a-126 | | | | | —Cl | |
| | a-127 | | | | | —Br | |
| | a-128 | | | | | —CH₂Cl | |
| | a-129 | | | | | —CH₂CH₂Cl | |
| | a-130 | | | | | —CHCHCl | |
| | a-131 | | | | | —CH(CH₃)₂ | |
| | a-132 | | | | | —CH=CHCH₃ | |
| | a-133 | —CN | —Cl | H | —CO₂Me | —CH₂CO₂Me | |
| | a-134 | | —CF₃ | | | | |
| | a-135 | | —OCF₃ | | | | |
| | a-136 | —CF₃ | —CN | | | | |
| | a-137 | | —OCF₃ | | | | |
| | a-138 | | —SOCF₃ | | | | |

Embodiment 5: Synthesis of Compounds b-1 to b-138 by Using a Method E

Method E:

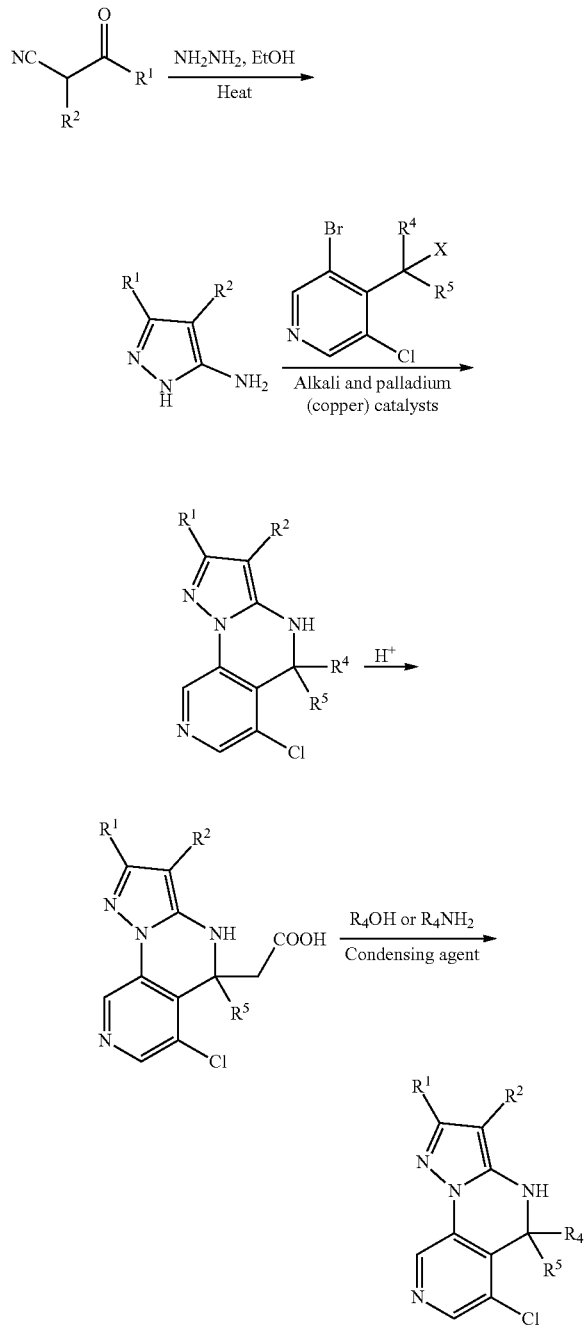

Taking a compound b-87 for example, a specific synthesis process was as follows:

S1: 5-amino-1H-pyrazole-3-trifluoromethyl (Referring to Document Journal of Medical Chemistry (2017) 60: 5099)

Under the protection of nitrogen, sodium hydride (2.5 mmol) was added to 20 ml of anhydrous tetrahydrofuran at 0° C., then anhydrous acetonitrile (2.0 mmol) and ethyl trifluoroacetate (1.0 mmol) were added to the reaction solution, heated and refluxed, and then the heating was stopped after 20 hours. The mixture was cooled to room temperature, and concentrated in vacuum. The mixture was extracted with ethyl ether and water, and diluted hydrochloric acid was added to adjust a pH to 2, then the mixture was extracted with ethyl ether, and concentrated in vacuum to obtain brown oily matter 4,4,4-trifluoro-3-carbonyl butyronitrile. The intermediate was directly used in next step without further purification.

Methanesulfonic acid (2.0 ml) was added to a mixture of 4,4,4-trifluoro-3-carbonyl butyronitrile (1.0 mmol) and hydrazine hydrate (1.0 ml), and the mixture was heated to 80° C. and reacted for 10 hours. Then, water and ethyl acetate were added for extraction, and concentrated in vacuum. The residues obtained were purified by column chromatography to obtain the target compound 5-amino-1H-pyrazole-3-trifluoromethyl which was as a yellow liquid (yield of the two steps: 15%), 1H NMR (400 MHz, DMSO-d6): δ 12.15 (s, 1H), 5.53 (s, 1H), 5.35 (s, 2H).

S2:6-chloro-2-trifluoromethyl-4,5-dihydropyrazole[1,5-α]quinazoline[4,3-e]pyridine-5-methyl formate Under the protection of nitrogen, a DMF mixture of 5-amino-1H-pyrazole-3-trifluoromethyl (1.0 mmol), 2-bromo-2-(3-bromo-5-chloropyridine-4-yl)-methyl acetate (1.0 mmol), cuprous iodide (0.2 mmol) and sodium ethoxide (0.5 mmol) was stirred at 100° C. for 24 hours. The mixture was cooled to room temperature, and then concentrated in vacuum, and the residues were purified by column chromatography to obtain the target compound 6-chloro-2-trifluoromethyl-4,5-dihydropyrazole[1,5-α]quinazoline[4,3-e]pyridine-5-methyl formate (yield: 35%).

S3: 6-chloro-2-trifluoromethyl-3-trifluoromethyl-sulfinyl-4,5-dihydropyrazole[1,5-α]quinazoline[4,3-e]pyridine-5-methyl formate Under the protection of nitrogen, an anhydrous toluene mixture of 6-chloro-2-trifluoromethyl-4,5-dihydropyrazole[1,5-α]quinazoline[4,3-e]pyridine-5-methyl formate (0.2 mmol), trifluoromethylsulfinyl chloride (0.5 mmol) and dimethylamine p-toluenesulfonate was stirred and heated at 100° C. for 24 hours. The mixture was cooled to room temperature, and then concentrated in vacuum, and the residues were purified by column chromatography to obtain the target compound 6-chloro-2-trifluoromethyl-3-trifluoromethylsulfinyl-4,5-dihydropyrazole[1,5-α]quinazoline[4,3-e]pyridine-5-methyl formate, wherein the yield was 85%.

The compounds b-1 to b-138 were synthesized with reference to the method of the compound b-87 (wherein cyclization steps also included similar cyclization methods mentioned in documents such as Synthetic Communications (2015) 45: 2426; Tetrahedron Letters (2014) 55: 4997; and WO2007149907) with a difference that different raw materials were selected for reaction according to different target compounds, or the compounds were derived from the synthesized target products through hydrolysis, simple esterification or amidation or reduction-oxidation. Specific compounds were as shown in Table 8.

TABLE 8

Compound Structure with a General Formula Shown in Formula (b)

| Structural formula | Compound | $R^1$ | $R^2$ | $R^3$ | $R^4$ | $R^5$ | $R^6$ |
|---|---|---|---|---|---|---|---|
| Formula (b) | b-1 | —CN | SOCF$_3$ | H | —CO$_2$Me | —CH$_2$CO$_2$Me | 5-Cl |
| | b-2 | | | | | —CH$_2$CN | |
| | b-3 | | | | | —CH$_2$CONH$_2$ | |
| | b-4 | | | | | —CH$_2$CONHCH$_3$ | |
| | b-5 | | | | | —CH$_2$CH$_2$OH | |
| | b-6 | | | | | —CH(CO$_2$Me)CH$_3$ | |
| | b-7 | | | —CH$_3$ | | —CH$_2$CO$_2$Me | |
| | b-8 | | | —CH$_2$CH$_2$Cl | | —CH$_2$CO$_2$Me | |
| | b-9 | | | H | | —CH$_2$CO$_2$Et | |
| | b-10 | | | | | —CH$_2$CO$_2$CH$_2$CF$_3$ | |
| | b-11 | | | | | —CH$_2$CO$_2$CH$_2$CHF$_2$ | |
| | b-12 | | | | | —CH$_2$CO$_2$CH(CF$_3$)$_2$ | |
| | b-13 | | | | | —CH$_2$CO$_2$C(CH$_3$)$_2$CF$_3$ | |
| | b-14 | | | | | —CH$_2$CO$_2$C(CF$_3$)$_2$CH$_3$ | |
| | b-15 | | | | | —CH$_2$CO$_2$CH(CF$_3$)OCH$_3$ | |
| | b-16 | | | | | —CH$_2$Ph | |
| | b-17 | | | | | —CH$_2$COCH$_3$ | |
| | b-18 | | | | | —CH$_2$Br | |
| | b-19 | | | | | —CH$_2$CF$_3$ | |
| | b-20 | | | | | —CH$_2$COCF$_3$ | |
| | b-21 | | —SOCH$_2$CH$_3$ | | | —CH$_2$CO$_2$Me | |
| | b-22 | | —SOCF$_3$ | H | —CO$_2$Et | —CH$_2$CO$_2$Et | |
| | b-23 | | | | | —CH$_2$CO$_2$Me | |
| | b-24 | | | | | —CH$_2$CO$_2$CH$_2$CF$_3$ | |
| | b-25 | | | | —COCF$_3$ | —CH$_2$COCF$_3$ | |
| | b-26 | | | | | —CH$_2$COCH$_3$ | |
| | b-27 | | | | | —CH$_2$Ph | |
| | b-28 | | | | | —CH$_2$CO$_2$Me | |
| | b-29 | | | | | —CH$_2$Br | |
| | b-30 | | | | | —CH$_2$CN | |
| | b-31 | | | | | —CH$_2$CF$_3$ | |
| | b-32 | | | | —COCH$_3$ | —CH$_2$COCH$_3$ | |
| | b-33 | | | | | —CH$_2$CO$_2$Me | |
| | b-34 | | | | | —CH$_2$Br | |
| | b-35 | | | | | —CH$_2$CN | |
| | b-36 | | | | | —CH$_2$CF$_3$ | |
| | b-37 | | | | | —CH$_2$COCF$_3$ | |
| | b-38 | | | | —CONHMe | —CH$_2$COCH$_3$ | |
| | b-39 | | | | | —CH$_2$CO$_2$Me | |
| | b-40 | | | | | —CH$_2$Br | |
| | b-41 | | | | | —CH$_2$CF$_3$ | |
| | b-42 | | | | | —CH$_2$COCF$_3$ | |
| | b-43 | | | | —NHMe | —CH$_2$CN | |
| | b-44 | | | | —Cl | —Cl | |
| | b-45 | | | | | —CH$_2$Br | |
| | b-46 | | | | | —CH$_2$Cl | |
| | b-47 | | | | | —CH$_2$CN | |
| | b-48 | | | | | —CH$_2$CF$_3$ | |
| | b-49 | | | | —Br | —CH$_2$Cl | |
| | b-50 | | | | | —CH$_2$COCF$_3$ | |
| | b-51 | | | | —CH$_3$ | —CH$_3$ | |
| | b-52 | | | | —CN | —CN | |
| | b-53 | | | | | —CH$_2$CN | |
| | b-54 | | | | | —CH$_2$CF$_3$ | |
| | b-55 | | | | | —CH$_2$Cl | |
| | b-56 | | | | | —CH$_2$CO$_2$Me | |
| | b-57 | | | | | —CH$_2$COCF$_3$ | |
| | b-58 | | | | CF$_3$ | —CF$_3$ | |
| | b-59 | | | | | —CH$_2$CN | |
| | b-60 | | | | | —CH$_2$CF$_3$ | |
| | b-61 | | | | | —CH$_2$Cl | |
| | b-62 | | | | | —CH$_2$CO$_2$Me | |
| | b-63 | | | | | —CH$_2$COCF$_3$ | |
| | b-64 | —CN | —SOCF$_3$ | H | H | —CO$_2$Me | |
| | b-65 | | | | | —CH$_2$CO$_2$Me | |
| | b-66 | | | | | —CH(CO$_2$Me)CH$_3$ | |
| | b-67 | | | | | —CH$_2$CO$_2$CH$_2$CF$_3$ | |
| | b-68 | | | | | —CO$_2$CH$_2$CF$_3$ | |
| | b-69 | | | | | —CH$_2$CO$_2$CH(CF$_3$)$_2$ | |
| | b-70 | | | | | —CH$_2$COCF$_3$ | |
| | b-71 | | | | | —COCF$_3$ | |
| | b-72 | | | | | —CN | |
| | b-73 | | | | | —CH$_2$CN | |
| | b-74 | | | | | —CF$_3$ | |
| | b-75 | | | | | —CH$_2$CF$_3$ | |

TABLE 8-continued

Compound Structure with a General Formula Shown in Formula (b)

| Structural formula | Compound | R$^1$ | R$^2$ | R$^3$ | R$^4$ | R$^5$ | R$^6$ |
|---|---|---|---|---|---|---|---|
| | b-76 | | | | | —CONHMe | |
| | b-77 | | | | | —CH$_2$CONHCH$_3$ | |
| | b-78 | | | | | —CH$_2$COCH$_3$ | |
| | b-79 | | | | | —COCH$_3$ | |
| | b-80 | | | | | —Cl | |
| | b-81 | | | | | —Br | |
| | b-82 | | | | | —CH$_2$Cl | |
| | b-83 | | | | | —CH$_2$CH$_2$Cl | |
| | b-84 | | | | | —CHCHCl | |
| | b-85 | | | | | —CH(CH$_3$)$_2$ | |
| | b-86 | | | | | —CH=CHCH$_3$ | |
| | b-87 | —CF$_3$ | —SOCF$_3$ | H | H | —CO$_2$Me | |
| | b-88 | | | | | —CH$_2$CO$_2$Me | |
| | b-89 | | | | | —CH(CO$_2$Me)CH$_3$ | |
| | b-90 | | | | | —CH$_2$CO$_2$CH$_2$CF$_3$ | |
| | b-91 | | | | | —CO$_2$CH$_2$CF$_3$ | |
| | b-92 | | | | | —CH$_2$CO$_2$CH(CF$_3$)$_2$ | |
| | b-93 | | | | | —CH$_2$COCF$_3$ | |
| | b-94 | | | | | —COCF$_3$ | |
| | b-95 | | | | | —CN | |
| | b-96 | | | | | —CH$_2$CN | |
| | b-97 | | | | | —CF$_3$ | |
| | b-98 | | | | | —CH$_2$CF$_3$ | |
| | b-99 | | | | | —CONHMe | |
| | b-100 | | | | | —CH$_2$CONHCH$_3$ | |
| | b-101 | | | | | —CH$_2$COCH$_3$ | |
| | b-102 | | | | | —COCH$_3$ | |
| | b-103 | | | | | —Cl | |
| | b-104 | | | | | —Br | |
| | b-105 | | | | | —CH$_2$Cl | |
| | b-106 | | | | | —CH$_2$CH$_2$Cl | |
| | b-107 | | | | | —CHCHCl | |
| | b-108 | | | | | —CH(CH$_3$)$_2$ | |
| | b-109 | | | | | —CH=CHCH$_3$ | |
| | b-110 | —CN | —OCF$_3$ | H | H | —CO$_2$Me | |
| | b-111 | | | | | —CH$_2$CO$_2$Me | |
| | b-112 | | | | | —CH(CO$_2$Me)CH$_3$ | |
| | b-113 | | | | | —CH$_2$CO$_2$CH$_2$CF$_3$ | |
| | b-114 | | | | | —CO$_2$CH$_2$CF$_3$ | |
| | b-115 | | | | | —CH$_2$CO$_2$CH(CF$_3$)$_2$ | |
| | b-116 | | | | | —CH$_2$COCF$_3$ | |
| | b-117 | | | | | —COCF$_3$ | |
| | b-118 | | | | | —CN | |
| | b-119 | | | | | —CH$_2$CN | |
| | b-120 | | | | | —CF$_3$ | |
| | b-121 | | | | | —CH$_2$CF$_3$ | |
| | b-122 | | | | | —CONHMe | |
| | b-123 | | | | | —CH$_2$CONHCH$_3$ | |
| | b-124 | | | | | —CH$_2$COCH$_3$ | |
| | b-125 | | | | | —COCH$_3$ | |
| | b-126 | | | | | —Cl | |
| | b-127 | | | | | —Br | |
| | b-128 | | | | | —CH$_2$Cl | |
| | b-129 | | | | | —CH$_2$CH$_2$Cl | |
| | b-130 | | | | | —CHCHCl | |
| | b-131 | | | | | —CH(CH$_3$)$_2$ | |
| | b-132 | | | | | —CH=CHCH$_3$ | |
| | b-133 | —CN | —Cl | H | —CO$_2$Me | —CH$_2$CO$_2$Me | |
| | b-134 | | —CF$_3$ | | | | |
| | b-135 | | —OCF$_3$ | | | | |
| | b-136 | —CF3 | —CN | | | | |
| | b-137 | | —OCF$_3$ | | | | |
| | b-138 | | —SOCF$_3$ | | | | |

91

Embodiment 6: Synthesis of Compounds c-1 To c-349 by Using a Method F

Method F:

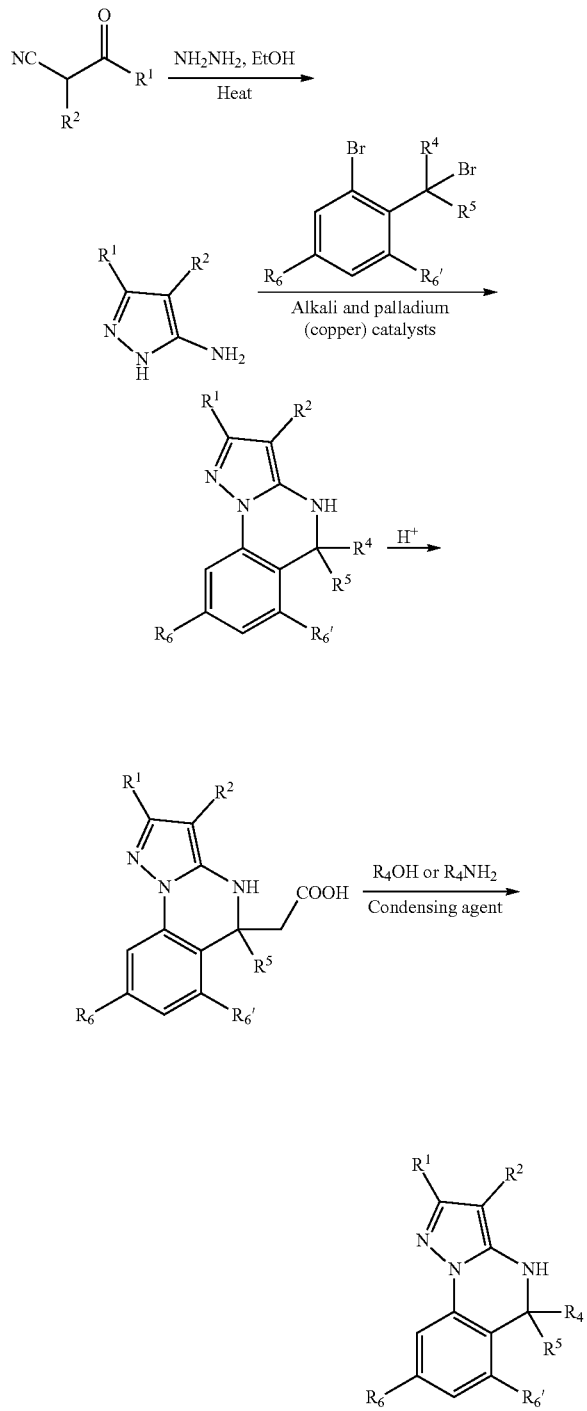

Taking a compound c-27 for example, a specific synthesis process was as follows:

92

S1: 6-chloro-2-cyano-5-(2'2-diethoxy)-8-trifluoromethyl-4,5-dihydropyrazole[1,5-α]quinazoline-5-ethyl formate Under the protection of nitrogen, a DMF mixture of 5-amino-1H-pyrazole-3-cyano (1.0 mmol), 2-bromo-2-(2-bromo-6-chloro-4-trifluoromethylphenyl)diethyl malate (1.0 mmol), cuprous iodide (0.2 mmol) and caesium carbonate (0.5 mmol) was stirred at 100° C. for 24 hours. The mixture was cooled to room temperature, and then filtered. The filtrate was concentrated in vacuum, and the residues were purified by column chromatography to obtain the target compound 6-chloro-2-cyano-5-(2'2-diethoxy)-8-trifluoromethyl-4,5-dihydropyrazole[1,5-α]quinazoline-5-ethyl formate (yield: 30%).

S2: 6-chloro-2-cyano-5-(2'2-diethoxy)-8-trifluoromethyl-3-trifluoromethylsulfinyl-4,5-dihydropyrazole[1,5-α]quinazoline-5-ethyl formate Under the protection of nitrogen, an anhydrous toluene mixture of 6-chloro-2-cyano-5-(2'2-diethoxy)-8-trifluoromethyl-4,5-dihydropyrazole[1,5-α]quinazoline-5-ethyl formate (0.2 mmol), trifluoromethylsulfinyl chloride (0.5 mmol) and dimethylamine p-toluenesulfonate was stirred and heated at 100° C. for 24 hours. The mixture was cooled to room temperature, and then concentrated in vacuum, and the residues were purified by column chromatography to obtain the target compound 6-chloro-2-cyano-5-(2'2-diethoxy)-8-trifluoromethyl-3-trifluoromethylsulfinyl-4,5-dihydropyrazole[1,5-α]quinazoline-5-ethyl formate, wherein the yield was 82%.

S3: 2-(6-chloro-2-cyano-5-(2'2-diethoxy)-8-trifluoromethyl-3-trifluoromethylsulfinyl-4,5-dihydropyrazole[1,5-α]quinazoline-5-yl)-acetic acid 6-chloro-2-cyano-5-(2'2-diethoxy)-8-trifluoromethyl-3-trifluoromethylsulfinyl-4,5-dihydropyrazole[1,5-α]quinazoline-5-ethyl formate (1.0 mmol) was dissolved in 5 ml of dioxane, and then 10 ml of 1N HCl was added thereto. The mixture was heated and refluxed for 5 hours, and then ethyl acetate was added for extraction. Then the mixture was concentrated in vacuum, and the residues were purified by column chromatography to obtain the target compound 2-(6-chloro-2-cyano-5-(2'2-diethoxy)-8-trifluoromethyl-3-trifluoromethylsulfinyl-4,5-dihydropyrazole[1,5-]quinazoline-5-yl)-acetic acid, wherein the yield was 78.

The compounds c-1 to c-349 were synthesized with reference to the method of the compound c-27 (wherein cyclization steps also included similar cyclization methods mentioned in documents such as WO2007144669) with a difference that different raw materials were selected for reaction according to different target compounds, or the compounds were derived from the synthesized target products through hydrolysis, simple esterification or amidation or reduction-oxidation. Specific compounds were as shown in Table 9.

TABLE 9

Compound Structure with a General Formula Shown in Formula (c)

| Structural formula | Compound | $R^1$ | $R^2$ | $R^3$ | $R^4$ | $R^5$ | $R^6$ |
|---|---|---|---|---|---|---|---|
| General formula (c) | c-1 | —CN | —CN | H | —CO₂Me | —CH₂CO₂Me | 3-Cl, and 5-CF₃ |
| | c-2 | | —CF₃ | | | | |
| | c-3 | | —OCF₃ | | | | |
| | c-4 | —CF₃ | —CN | | | | |
| | c-5 | | —CF₃ | | | | |
| | c-6 | | —OCF₃ | | | | |
| | c-7 | | —SOCF₃ | | | | |
| | c-8 | —CN | —SOCF₃ | H | —CO₂Me | —CH₂CO₂Me | |
| | c-9 | | | | | —CH₂CN | |
| | c-10 | | | | | —CH₂CONH₂ | |
| | c-11 | | | | | —CH₂CONHCH₃ | |
| | c-12 | | | | | —CH₂CH₂OH | |
| | c-13 | | | | | —CH(CO₂Me)CH₃ | |
| | c-14 | | | —CH₃ | | —CO₂Me | |
| | c-15 | | | —Ac | | | |
| | c-16 | | | —CH₂CH₂Cl | | | |
| | c-17 | | | H | | —CH₂CO₂Et | |
| | c-18 | | | | | —COOH | |
| | c-19 | | | | | —CH₂CO₂CH₂CF₃ | |
| | c-20 | | | | | —CH₂CO₂CH₂CHF₂ | |
| | c-21 | | | | | —CH₂CO₂CH(CF₃)₂ | |
| | c-22 | | | | | —CH₂CO₂C(CH₃)₂CF₃ | |
| | c-23 | | | | | —CH₂CO₂C(CF₃)₂CH₃ | |
| | c-24 | | | | | —CH₂CO₂C(CF₃)OCH₃ | |
| | c-25 | | | | —CO₂Et | —CH₂CO₂Me | |
| | c-26 | | | | | —CH₂CO₂Et | |
| | c-27 | | | | | —CH₂CO₂H | |
| | c-28 | | | | | —CH₂CO₂CH₂CF₃ | |
| | c-29 | | | | | —CH₂CO₂CH₂CHF₂ | |
| | c-30 | | | | | —CH₂CO₂CH(CF₃)₂ | |
| | c-31 | | | | | —CH₂CO₂C(CH₃)₂CF₃ | |
| | c-32 | | | | | —CH₂CO₂C(CF₃)₂CH₃ | |
| | c-33 | | | | | —CH₂CO₂C(CF₃)OCH₃ | |
| | c-34 | | | | —COCF₃ | —CH₂COCF₃ | |
| | c-35 | | | | | —CH₂COCH₃ | |
| | c-36 | | | | | —CH₂Ph | |
| | c-37 | | | | | —CH(CH₃)₂ | |
| | c-38 | | | | | —CH₂CO₂Me | |
| | c-39 | | | | | —COCH₃ | |
| | c-40 | | | | | —CO₂Me | |
| | c-41 | | | | | —CH₂Br | |
| | c-42 | | | | | —CH₂CH₂Cl | |
| | c-43 | | | | | —CN | |
| | c-44 | | | | | —CH₂CN | |
| | c-45 | | | | | —CF₃ | |
| | c-46 | | | | | —CH₂CF₃ | |
| | c-47 | | | | —COCH₃ | —CH₂COCF₃ | |
| | c-48 | | | | | —CH₂COCH₃ | |
| | c-49 | | | | | —CH₂Ph | |
| | c-50 | | | | | —CH(CH₃)₂ | |
| | c-51 | | | | | —CH₂CO₂Me | |
| | c-52 | | | | | —COCH₃ | |
| | c-53 | | | | | —CO₂Me | |
| | c-54 | | | | | —CH₂Br | |
| | c-55 | | | | | —CH₂CH₂Cl | |
| | c-56 | | | | | —CN | |
| | c-57 | | | | | —CH₂CN | |
| | c-58 | | | | | —CF₃ | |
| | c-59 | | | | | —CH₂CF₃ | |
| | c-60 | | | | —CO₂Me | —CO₂Me | |
| | c-61 | | | | | —CH₂Ph | |
| | c-62 | | | | | —CH₃ | |
| | c-63 | | | | | —CH₂COCH₃ | |
| | c-64 | | | | | —CH₂Br | |
| | c-65 | | | | | —CH₂CH₂Cl | |
| | c-66 | | | | | —Br | |
| | c-67 | | | | | —CN | |
| | c-68 | | | | | —CF₃ | |
| | c-69 | | | | | —CH₂CF₃ | |
| | c-70 | | | | | —CH₂COCF₃ | |
| | c-71 | | | | —CONHMe | —CH₂COCH₃ | |
| | c-72 | | | | | —COCH₃ | |
| | c-73 | | | | | —CO₂Me | |
| | c-74 | | | | | —CH₂CO₂Me | |
| | c-75 | | | | | —CH₂Ph | |

TABLE 9-continued

Compound Structure with a General Formula Shown in Formula (c)

| Structural formula | Compound | R¹ | R² | R³ | R⁴ | R⁵ | R⁶ |
|---|---|---|---|---|---|---|---|
| | c-76 | | | | | —CH₃ | |
| | c-77 | | | | | —Br | |
| | c-78 | | | | | —CH₂Br | |
| | c-79 | | | | | —CH₂CH₂Cl | |
| | c-80 | | | | | —CN | |
| | c-81 | | | | | —CH₂CN | |
| | c-82 | | | | | —CF₃ | |
| | c-83 | | | | | —CH₂CF₃ | |
| | c-84 | | | | | —CH₂COCF₃ | |
| | c-85 | | | | | —COCF₃ | |
| | c-86 | | | | —F | —F | |
| | c-87 | | | | —Cl | —Cl | |
| | c-88 | | | | | —CH₂Br | |
| | c-89 | | | | | —CH₂Cl | |
| | c-90 | | | | | —CN | |
| | c-91 | | | | | —CH₂CN | |
| | c-92 | | | | | —CF₃ | |
| | c-93 | | | | | —CH₂CF₃ | |
| | c-94 | | | | —Br | —Br | |
| | c-95 | | | | | —CH₂Cl | |
| | c-96 | | | | | —CH₂COCF₃ | |
| | c-97 | | | | | —COCF₃ | |
| | c-98 | | | | —CH₃ | —CH₃ | |
| | c-99 | | | | | —CH₂CH₃ | |
| | c-100 | | | | —CN | —CN | |
| | c-101 | | | | | —CH₂CN | |
| | c-102 | | | | | —CF₃ | |
| | c-103 | | | | | —CH₂CF₃ | |
| | c-104 | | | | | —CH₂Cl | |
| | c-105 | | | | | —CH₂CO₂Me | |
| | c-106 | | | | | —COCH₃ | |
| | c-107 | | | | | —COCF₃ | |
| | c-108 | | | | | —CH₂COCF₃ | |
| | c-109 | | | | —CF₃ | —CF₃ | |
| | c-110 | | | | | —CH₂CF₃ | |
| | c-111 | | | | | —CH₂CN | |
| | c-112 | | | | | —CH₂Cl | |
| | c-113 | | | | | —CH₂CO₂Me | |
| | c-114 | | | | | —COCH₃ | |
| | c-115 | | | | | —COCF₃ | |
| | c-116 | | | | | —CH₂COCF₃ | |
| | c-117 | | | | —CO₂nBu | —CH₂CO₂nBu | |
| | c-118 | —SOCH₂CH₃ | | | —CO₂Me | —CH₂CO₂Me | |
| | c-119 | —CN | —SOCF₃ | H | H | —CO₂Me | |
| | c-120 | | | | | —CH₂CO₂Me | |
| | c-121 | | | | | —C(CO₂Me)CH₃ | |
| | c-122 | | | | | —CH₂CO₂CH₂CF₃ | |
| | c-123 | | | | | —CO₂CH₂CF₃ | |
| | c-124 | | | | | —CH₂CO₂CH(CF₃)₂ | |
| | c-125 | | | | | —CH₂COCF₃ | |
| | c-126 | | | | | —COCF₃ | |
| | c-127 | | | | | —CN | |
| | c-128 | | | | | —CH₂CN | |
| | c-129 | | | | | —CF₃ | |
| | c-130 | | | | | —CH₂CF₃ | |
| | c-131 | | | | | —CONHMe | |
| | c-132 | | | | | —CH₂CONHCH₃ | |
| | c-133 | | | | | —CH₂COCH₃ | |
| | c-134 | | | | | —COCH₃ | |
| | c-135 | | | | | —Cl | |
| | c-136 | | | | | —Br | |
| | c-137 | | | | | —CH₂Cl | |
| | c-138 | | | | | —CH₂CH₂Cl | |
| | c-139 | | | | | —CH=CHCl | |
| | c-140 | | | | | —CH(CH₃)₂ | |
| | c-141 | | | | | —CH=CHCH₃ | |
| | c-142 | —CF₃ | —SOCF₃ | H | H | —CO₂Me | |
| | c-143 | | | | | —CH₂CO₂Me | |
| | c-144 | | | | | —C(CO₂Me)CH₃ | |
| | c-145 | | | | | —CH₂CO₂CH₂CF₃ | |
| | c-146 | | | | | —CO₂CH₂CF₃ | |
| | c-147 | | | | | —CH₂CO₂CH(CF₃)₂ | |
| | c-148 | | | | | —CH₂COCF₃ | |
| | c-149 | | | | | —COCF₃ | |
| | c-150 | | | | | —CN | |

TABLE 9-continued

Compound Structure with a General Formula Shown in Formula (c)

| Structural formula | Compound | R¹ | R² | R³ | R⁴ | R⁵ | R⁶ |
|---|---|---|---|---|---|---|---|
| | c-151 | | | | | —CH$_2$CN | |
| | c-152 | | | | | —CF$_3$ | |
| | c-153 | | | | | —CH$_2$CF$_3$ | |
| | c-154 | | | | | —CONHMe | |
| | c-155 | | | | | —CH$_2$CONHCH$_3$ | |
| | c-156 | | | | | —CH$_2$COCH$_3$ | |
| | c-157 | | | | | —COCH$_3$ | |
| | c-158 | | | | | —Cl | |
| | c-159 | | | | | —Br | |
| | c-160 | | | | | —CH$_2$Cl | |
| | c-161 | | | | | —CH$_2$CH$_2$Cl | |
| | c-162 | | | | | —CH=CHCl | |
| | c-163 | | | | | —CH(CH$_3$)$_2$ | |
| | c-164 | | | | | —CH=CHCH$_3$ | |
| | c-165 | —CN | —OCF$_3$ | H | H | —CO$_2$Me | |
| | c-166 | | | | | —CH$_2$CO$_2$Me | |
| | c-167 | | | | | —C(CO$_2$Me)CH$_3$ | |
| | c-168 | | | | | —CH$_2$CO$_2$CH$_2$CF$_3$ | |
| | c-169 | | | | | —CO$_2$CH$_2$CF$_3$ | |
| | c-170 | | | | | —CH$_2$CO$_2$CH(CF$_3$)$_2$ | |
| | c-171 | | | | | —CH$_2$COCF$_3$ | |
| | c-172 | | | | | —COCF$_3$ | |
| | c-173 | | | | | —CN | |
| | c-174 | | | | | —CH$_2$CN | |
| | c-175 | | | | | —CF$_3$ | |
| | c-176 | | | | | —CH$_2$CF$_3$ | |
| | c-177 | | | | | —CONHMe | |
| | c-178 | | | | | —CH$_2$CONHCH$_3$ | |
| | c-179 | | | | | —CH$_2$COCH$_3$ | |
| | c-180 | | | | | —COCH$_3$ | |
| | c-181 | | | | | —Cl | |
| | c-182 | | | | | —Br | |
| | c-183 | | | | | —CH$_2$Cl | |
| | c-184 | | | | | —CH$_2$CH$_2$Cl | |
| | c-185 | | | | | —CH=CHCl | |
| | c-186 | | | | | —CH(CH$_3$)$_2$ | |
| | c-187 | | | | | —CH=CHCH$_3$ | |
| | c-188 | —CN | —SOCF$_3$ | H | —CO$_2$Me | —CH$_2$CO$_2$Me | 3-Br, and 5-CF$_3$ |
| | c-189 | | | | | —CH$_2$CO$_2$Et | |
| | c-190 | | | | | —CH$_2$CO$_2$CH$_2$CF$_3$ | |
| | c-191 | | | | | —CH$_2$CO$_2$CH$_2$CHF$_2$ | |
| | c-192 | | | | —CO$_2$Et | —CH$_2$CO$_2$Me | |
| | c-193 | | | | | —CH$_2$CO$_2$Et | |
| | c-194 | | | | —CO$_2$Me | —CH$_2$CO$_2$Me | 3-CF$_3$, and 5-CF$_3$ |
| | c-195 | | | | | —CH$_2$CO$_2$Et | |
| | c-196 | | | | | —CH$_2$CO$_2$CH$_2$CF$_3$ | |
| | c-197 | | | | | —CH$_2$CO$_2$CH$_2$CHF$_2$ | |
| | c-198 | | | | —CO$_2$Et | —CH$_2$CO$_2$Me | |
| | c-199 | | | | | —CH$_2$CO$_2$Et | |
| | c-200 | | | | —CO$_2$Me | —CH$_2$CO$_2$Me | 3-Me, and 5-CF$_3$ |
| | c-201 | | | | | —CH$_2$CO$_2$Et | |
| | c-202 | | | | | —CH$_2$CO$_2$CH$_2$CF$_3$ | |
| | c-203 | | | | | —CH$_2$CO$_2$CH$_2$CHF$_2$ | |
| | c-204 | | | | —CO$_2$Et | —CH$_2$CO$_2$Me | |
| | c-205 | | | | | —CH$_2$CO$_2$Et | |
| | c-206 | | | | —CO$_2$Me | —CH$_2$CO$_2$Me | 3-CN, and 5-CF$_3$ |
| | c-207 | | | | | —CH$_2$CO$_2$Et | |
| | c-208 | | | | | —CH$_2$CO$_2$CH$_2$CF$_3$ | |
| | c-209 | | | | | —CH$_2$CO$_2$CH$_2$CHF$_2$ | |
| | c-210 | | | | —CO$_2$Et | —CH$_2$CO$_2$Me | |
| | c-211 | | | | | —CH$_2$CO$_2$Et | |
| | c-212 | | | | —CO$_2$Me | —CH$_2$CO$_2$Me | 3-CO$_2$Me, and 5-CF$_3$ |
| | c-213 | | | | | —CH$_2$CO$_2$Et | |
| | c-214 | | | | | —CH$_2$CO$_2$CH$_2$CF$_3$ | |
| | c-215 | | | | | —CH$_2$CO$_2$CH$_2$CHF$_2$ | |
| | c-216 | | | | —CO$_2$Et | —CH$_2$CO$_2$Me | |
| | c-217 | | | | | —CH$_2$CO$_2$Et | |
| | c-218 | | | | —CO$_2$Me | —CH$_2$CO$_2$Me | 3-NO$_2$, and 5-CF$_3$ |
| | c-219 | | | | | —CH$_2$CO$_2$Et | |
| | c-220 | | | | | —CH$_2$CO$_2$CH$_2$CF$_3$ | |
| | c-221 | | | | | —CH$_2$CO$_2$CH$_2$CHF$_2$ | |
| | c-222 | | | | —CO$_2$Et | —CH$_2$CO$_2$Me | |
| | c-223 | | | | | —CH$_2$CO$_2$Et | |
| | c-224 | —CN | —SOCF$_3$ | H | —CO$_2$Me | —CH$_2$CO$_2$Me | 3-Cl, and 5- |
| | c-225 | | | | | —CH$_2$CO$_2$Et | |

TABLE 9-continued

Compound Structure with a General Formula Shown in Formula (c)

| Structural formula | Compound | R¹ | R² | R³ | R⁴ | R⁵ | R⁶ |
|---|---|---|---|---|---|---|---|
| | c-226 | | | | | —CH₂CO₂CH₂CF₃ | OCF₃ |
| | c-227 | | | | | —CH₂CO₂CH₂CHF₂ | |
| | c-228 | | | | —CO₂Et | —CH₂CO₂Me | |
| | c-229 | | | | | —CH₂CO₂Et | |
| | c-230 | | | | —CO₂Me | —CH₂CO₂Me | 3-Br, |
| | c-231 | | | | | —CH₂CO₂Et | and 5- |
| | c-232 | | | | | —CH₂CO₂CH₂CF₃ | OCF₃ |
| | c-233 | | | | | —CH₂CO₂CH₂CHF₂ | |
| | c-234 | | | | —CO₂Et | —CH₂CO₂Me | |
| | c-235 | | | | | —CH₂CO₂Et | |
| | c-236 | | | | —CO₂Me | —CH₂CO₂Me | 3-Me, |
| | c-237 | | | | | —CH₂CO₂Et | and 5- |
| | c-238 | | | | | —CH₂CO₂CH₂CF₃ | OCF₃ |
| | c-239 | | | | | —CH₂CO₂CH₂CHF₂ | |
| | c-240 | | | | —CO₂Et | —CH₂CO₂Me | |
| | c-241 | | | | | —CH₂CO₂Et | |
| | c-242 | | | | —CO₂Me | —CH₂CO₂Me | 3-CN, |
| | c-243 | | | | | —CH₂CO₂Et | and 5- |
| | c-244 | | | | | —CH₂CO₂CH₂CF₃ | OCF₃ |
| | c-245 | | | | | —CH₂CO₂CH₂CHF₂ | |
| | c-246 | | | | —CO₂Et | —CH₂CO₂Me | |
| | c-247 | | | | | —CH₂CO₂Et | |
| | c-248 | | | | —CO₂Me | —CH₂CO₂Me | 3-CH₃, |
| | c-249 | | | | | —CH₂CO₂Et | and |
| | c-250 | | | | | —CH₂CO₂CH₂CF₃ | 5-OCF₃ |
| | c-251 | | | | | —CH₂CO₂CH₂CHF₂ | |
| | c-252 | | | | —CO₂Et | —CH₂CO₂Me | |
| | c-253 | | | | | —CH₂CO₂Et | |
| | c-254 | | | | —CO₂Me | —CH₂CO₂Me | 3-CO₂Me, |
| | c-255 | | | | | —CH₂CO₂Et | and |
| | c-256 | | | | | —CH₂CO₂CH₂CF₃ | 5-OCF₃ |
| | c-257 | | | | | —CH₂CO₂CH₂CHF₂ | |
| | c-258 | | | | —CO₂Et | —CH₂CO₂Me | |
| | c-259 | | | | | —CH₂CO₂Et | |
| | c-260 | | | | —CO₂Me | —CH₂CO₂Me | 3-NO₂, |
| | c-261 | | | | | —CH₂CO₂Et | and |
| | c-262 | | | | | —CH₂CO₂CH₂CF₃ | 5-OCF₃ |
| | c-263 | | | | | —CH₂CO₂CH₂CHF₂ | |
| | c-264 | | | | —CO₂Et | —CH₂CO₂Me | |
| | c-265 | | | | | —CH₂CO₂Et | |
| | c-266 | —CN | —SOCF₃ | H | —CO₂Me | —CH₂CO₂Me | 3-Cl, |
| | c-267 | | | | | —CH₂CO₂Et | and 5-NO₂ |
| | c-268 | | | | | —CH₂CO₂CH₂CF₃ | |
| | c-269 | | | | | —CH₂CO₂CH₂CHF₂ | |
| | c-270 | | | | —CO₂Et | —CH₂CO₂Me | |
| | c-271 | | | | | —CH₂CO₂Et | |
| | c-272 | | | | —CO₂Me | —CH₂CO₂Me | 3-Br, |
| | c-273 | | | | | —CH₂CO₂Et | and 5- |
| | c-274 | | | | | —CH₂CO₂CH₂CF₃ | NO₂ |
| | c-275 | | | | | —CH₂CO₂CH₂CHF₂ | |
| | c-276 | | | | —CO₂Et | —CH₂CO₂Me | |
| | c-277 | | | | | —CH₂CO₂Et | |
| | c-278 | | | | —CO₂Me | —CH₂CO₂Me | 3-Me, |
| | c-279 | | | | | —CH₂CO₂Et | and 5- |
| | c-280 | | | | | —CH₂CO₂CH₂CF₃ | NO₂ |
| | c-281 | | | | | —CH₂CO₂CH₂CHF₂ | |
| | c-282 | | | | —CO₂Et | —CH₂CO₂Me | |
| | c-283 | | | | | —CH₂CO₂Et | |
| | c-284 | | | | —CO₂Me | —CH₂CO₂Me | 3-CN, |
| | c-285 | | | | | —CH₂CO₂Et | and 5- |
| | c-286 | | | | | —CH₂CO₂CH₂CF₃ | NO₂ |
| | c-287 | | | | | —CH₂CO₂CH₂CHF₂ | |
| | c-288 | | | | —CO₂Et | —CH₂CO₂Me | |
| | c-289 | | | | | —CH₂CO₂Et | |
| | c-290 | | | | —CO₂Me | —CH₂CO₂Me | 3-CF₃, |
| | c-291 | | | | | —CH₂CO₂Et | and 5- |
| | c-292 | | | | | —CH₂CO₂CH₂CF₃ | NO₂ |
| | c-293 | | | | | —CH₂CO₂CH₂CHF₂ | |
| | c-294 | | | | —CO₂Et | —CH₂CO₂Me | |
| | c-295 | | | | | —CH₂CO₂Et | |
| | c-296 | | | | —CO₂Me | —CH₂CO₂Me | 3-CO₂Me, |
| | c-297 | | | | | —CH₂CO₂Et | and 5-NO₂ |
| | c-298 | | | | | —CH₂CO₂CH₂CF₃ | |
| | c-299 | | | | | —CH₂CO₂CH₂CHF₂ | |
| | c-300 | | | | —CO₂Et | —CH₂CO₂Me | |

TABLE 9-continued

Compound Structure with a General Formula Shown in Formula (c)

| Structural formula | Compound | R¹ | R² | R³ | R⁴ | R⁵ | R⁶ |
|---|---|---|---|---|---|---|---|
| | c-301 | | | | | —CH$_2$CO$_2$Et | |
| | c-302 | | | | —CO$_2$Me | —CH$_2$CO$_2$Me | 3-NO$_2$, |
| | c-303 | | | | | —CH$_2$CO$_2$Et | and |
| | c-304 | | | | | —CH$_2$CO$_2$CH$_2$CF$_3$ | 5-NO$_2$ |
| | c-305 | | | | | —CH$_2$CO$_2$CH$_2$CHF$_2$ | |
| | c-306 | | | | —CO$_2$Et | —CH$_2$CO$_2$Me | |
| | c-307 | | | | | —CH$_2$CO$_2$Et | |
| | c-308 | —CN | —SOCF$_3$ | H | —CO$_2$Me | —CH$_2$CO$_2$Me | 3-Cl, and |
| | c-309 | | | | | —CH$_2$CO$_2$Et | 5-Cl |
| | c-310 | | | | | —CH$_2$CO$_2$CH$_2$CF$_3$ | |
| | c-311 | | | | | —CH$_2$CO$_2$CH$_2$CHF$_2$ | |
| | c-312 | | | | —CO$_2$Et | —CH$_2$CO$_2$Me | |
| | c-313 | | | | | —CH$_2$CO$_2$Et | |
| | c-314 | | | | —CO$_2$Me | —CH$_2$CO$_2$Me | 3-Br, and |
| | c-315 | | | | | —CH$_2$CO$_2$Et | 5-Cl |
| | c-316 | | | | | —CH$_2$CO$_2$CH$_2$CF$_3$ | |
| | c-317 | | | | | —CH$_2$CO$_2$CH$_2$CHF$_2$ | |
| | c-318 | | | | —CO$_2$Et | —CH$_2$CO$_2$Me | |
| | c-319 | | | | | —CH$_2$CO$_2$Et | |
| | c-320 | | | | —CO$_2$Me | —CH$_2$CO$_2$Me | |
| | c-321 | | | | | —CH$_2$CO$_2$Et | 3-Me, |
| | c-322 | | | | | —CH$_2$CO$_2$CH$_2$CF$_3$ | and 5-Cl |
| | c-323 | | | | | —CH$_2$CO$_2$CH$_2$CHF$_2$ | |
| | c-324 | | | | —CO$_2$Et | —CH$_2$CO$_2$Me | |
| | c-325 | | | | | —CH$_2$CO$_2$Et | |
| | c-326 | | | | —CO$_2$Me | —CH$_2$CO$_2$Me | 3-CN, |
| | c-327 | | | | | —CH$_2$CO$_2$Et | and 5- |
| | c-328 | | | | | —CH$_2$CO$_2$CH$_2$CF$_3$ | Cl |
| | c-329 | | | | | —CH$_2$CO$_2$CH$_2$CHF$_2$ | |
| | c-330 | | | | —CO$_2$Et | —CH$_2$CO$_2$Me | |
| | c-331 | | | | | —CH$_2$CO$_2$Et | |
| | c-332 | | | | —CO$_2$Me | —CH$_2$CO$_2$Me | 3-CF$_3$, |
| | c-333 | | | | | —CH$_2$CO$_2$Et | and 5-Cl |
| | c-334 | | | | | —CH$_2$CO$_2$CH$_2$CF$_3$ | |
| | c-335 | | | | | —CH$_2$CO$_2$CH$_2$CHF$_2$ | |
| | c-336 | | | | —CO$_2$Et | —CH$_2$CO$_2$Me | |
| | c-337 | | | | | —CH$_2$CO$_2$Et | |
| | c-338 | | | | —CO$_2$Me | —CH$_2$CO$_2$Me | 3-CO$_2$Me, |
| | c-339 | | | | | —CH$_2$CO$_2$Et | and 5-Cl |
| | c-340 | | | | | —CH$_2$CO$_2$CH$_2$CF$_3$ | |
| | c-341 | | | | | —CH$_2$CO$_2$CH$_2$CHF$_2$ | |
| | c-342 | | | | —CO$_2$Et | —CH$_2$CO$_2$Me | |
| | c-343 | | | | | —CH$_2$CO$_2$Et | |
| | c-344 | | | | —CO$_2$Me | —CH$_2$CO$_2$Me | 3-NO$_2$, and |
| | c-345 | | | | | —CH$_2$CO$_2$Et | 5-Cl |
| | c-346 | | | | | —CH$_2$CO$_2$CH$_2$CF$_3$ | |
| | c-347 | | | | | —CH$_2$CO$_2$CH$_2$CHF$_2$ | |
| | c-348 | | | | —CO$_2$Et | —CH$_2$CO$_2$Me | |
| | c-349 | | | | | —CH$_2$CO$_2$Et | |

Embodiment 7: Synthesis of Compounds d-1 to d-142 by Using a Method G

Method G:

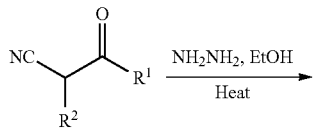

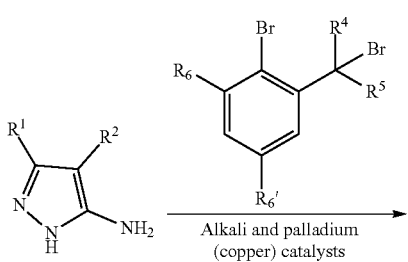

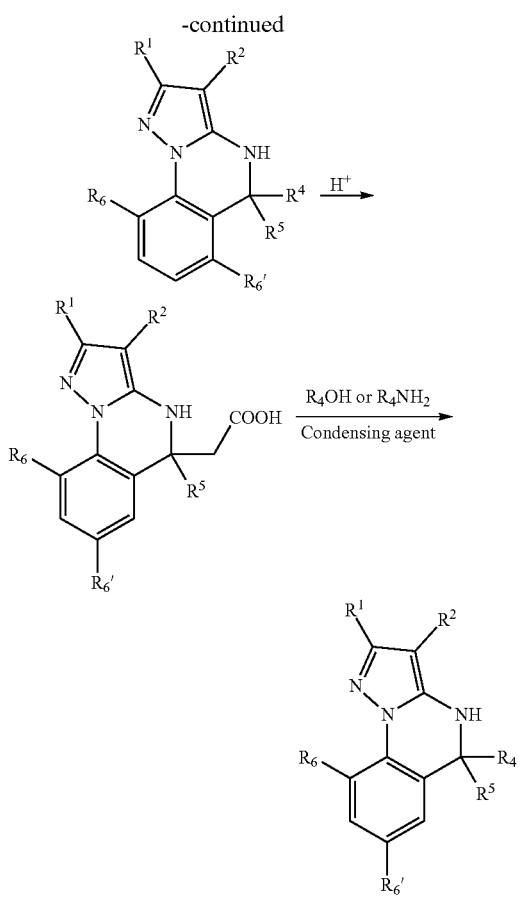

Taking a compound d-12 for example, a specific synthesis process was as follows:

S1: 9-chloro-2-cyano-3-cyclohexanethiol-5-(2'2-dimethoxy)-7-trifluoromethyl-4,5-dihydropyrazole[1,5-α]quinazoline-5-methyl formate (Referring to Document Synthetic Communications (2012) 42: 3472)

Under the protection of nitrogen, an anhydrous acetonitrile mixture of 9-chloro-2-cyano-5-(2'2-dimethoxy)-7-trifluoromethyl-4,5-dihydropyrazole[1,5-α]quinazoline-5-methyl formate (2.0 mmol, synthesized with a method similar to S of the compound c-27, with a yield of 26%), dicyclohexyl disulfide (1.0 mmol), ferric tribromide (0.5 mmol) and elemental iodine (0.5 mmol) was stirred at 85° C. for 24 hours. The mixture was cooled to room temperature, and then concentrated in vacuum, and the residues were purified by column chromatography to obtain the target compound 9-chloro-2-cyano-3-cyclohexanethiol-5-(2'2-dimethoxy)-7-trifluoromethyl-4,5-dihydropyrazole[1,5-α]quinazoline-5-methyl formate (yield: 90%).

S2: 9-chloro-2-cyano-3-cyclohexanesulfinyl-5-(2'2-dimethoxy)-7-trifluoromethyl-4,5-dihydropyrazole[1,5-α]quinazoline-5-methyl formate 9-chloro-2-cyano-3-cyclohexanethiol-5-(2'2-dimethoxy)-7-trifluoromethyl-4,5-dihydropyrazole[1,5-α]quinazoline-5-methyl formate (1.0 mmol) was dissolved in anhydrous methylene chloride, and cooled to −15° C. Then, m-chloroperoxybenzoic acid (85%, 1.1 mmol) was added thereto, and the mixture was reacted at low temperature for 1 hour under stirring. The mixture was cooled to room temperature, added with an aqueous solution of sodium hydrogen carbonate, extracted with methylene chloride, and concentrated in vacuum. The residues were purified by column chromatography to obtain the target compound 9-chloro-2-cyano-3-cyclohexanesulfinyl-5-(2'2-dimethoxy)-7-trifluoromethyl-4,5-dihydropyrazole[1,5-α]quinazoline-5-methyl formate, wherein the yield was 97%.

The compounds d-1 to d-142 were synthesized with reference to the method of the compound d-12 (wherein cyclization steps also included similar cyclization methods mentioned in documents such as Tetrahedron Letters (2015) 56: 1367; WO2016046404; Synthetic Communications (2015) 45: 2426; Tetrahedron Letters (2014) 55: 4997; and WO2007149907), with a difference that different raw materials were selected for reaction according to different target compounds, or the compounds were derived from the synthesized target products through hydrolysis, simple esterification or amidation or reduction-oxidation. Specific compounds were as shown in Table 10.

TABLE 10

CompoundStructure with a General FormulaShown in Formula (d)

| Structural formula | Compound | $R^1$ | $R^2$ | $R^3$ | $R^4$ | $R^5$ | $R^6$ |
|---|---|---|---|---|---|---|---|
| General formula (d) | d-1 | —CN | —$CF_3$ | H | —$CO_2Me$ | —$CH_2CO_2Me$ | 4-$CF_3$, and 6-Cl |
| | d-2 | | —Br | | | | |
| | d-3 | | —$OCF_3$ | | | | |
| | d-4 | | —Cl | | | | |
| | d-5 | —$CF_3$ | —$CF_3$ | | | | |
| | d-6 | | —$OCF_3$ | | | | |
| | d-7 | | —CN | | | | |
| | d-8 | —$COCH_3$ | —$SOCF_3$ | H | —$CO_2Me$ | —$CH_2CO_2Me$ | |
| | d-9 | —$CH_2NH_2$ | | | | | |
| | d-10 | —CN | —SOPh | | | | |
| | d-11 | | —$SOCH_2Ph$ | | | | |
| | d-12 | | —$SOC_6H_{13}$ | | | | |
| | d-13 | | —$SOCH_3$ | | | | |
| | d-14 | | —$SOCH_2CH_3$ | | | | |

TABLE 10-continued

Compound Structure with a General Formula Shown in Formula (d)

| Structural formula | Compound | R¹ | R² | R³ | R⁴ | R⁵ | R⁶ |
|---|---|---|---|---|---|---|---|
| | d-15 | | 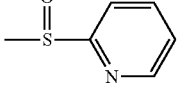 | | | | |
| | d-16 | | 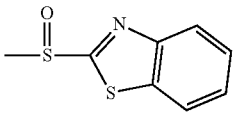 | | | | |
| | d-17 | | 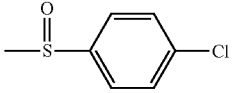 | | | | |
| | d-18 | | 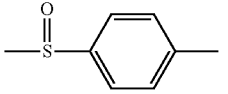 | | | | |
| | d-19 | —CF₃ | —SOCF₃ | H | —CO₂Me | —CH₂CO₂Me | |
| | d-20 | —CN | —SOCF₃ | H | —CO₂Me | —CH₂CONH₂ | |
| | d-21 | | | | | —CH₂CONHCH₃ | |
| | d-22 | | | | | —CH₂CON(CH₃)₂ | |
| | d-23 | | | | | —CH₂CH₂OH | |
| | d-24 | | | | | —CH(CO₂Me)CH₃ | |
| | d-25 | | | | | —CH₂CO₂H | |
| | d-26 | | | | | —CH₂CO₂Et | |
| | d-27 | | | | | —CH₂CO₂CH₂CF₃ | |
| | d-28 | | | | | —CH₂CO₂CH₂CHF₂ | |
| | d-29 | | | | | —CH₂CO₂CH(CF₃)₂ | |
| | d-30 | | | | | —CH₂CO₂C(CH₃)₂CF₃ | |
| | d-31 | | | | | —CH₂CO₂C(CF₃)₂CH₃ | |
| | d-32 | | | | | —CH₂CO₂CH(CF₃)OCH₃ | |
| | d-33 | | | | | —CH₂COCH₃ | |
| | d-34 | | | | | —CH₂Br | |
| | d-35 | | | | | —CH₂CF₃ | |
| | d-36 | | | | | —CH₂COCF₃ | |
| | d-37 | | | | —CO₂Et | —CH₂CO₂Et | |
| | d-38 | | | | | —CH₂CO₂H | |
| | d-39 | | | | | —CH₂CO₂Me | |
| | d-40 | | | | | —CH₂CO₂CH₂CF₃ | |
| | d-41 | | | | | —CH₂CO₂CH₂CHF₂ | |
| | d-42 | | | | | —CH₂CO₂CH(CF₃)₂ | |
| | d-43 | | | | | —CH₂CO₂C(CH₃)₂CF₃ | |
| | d-44 | | | | | —CH₂CO₂C(CF₃)₂CH₃ | |
| | d-45 | | | | | —CH₂CO₂CH(CF₃)OCH₃ | |
| | d-46 | | | | —COCH₃ | —CH₂COCH₃ | |
| | d-47 | | | | | —CH₂CO₂Me | |
| | d-48 | | | | | —CH₂CF₃ | |
| | d-49 | | | | | —CH₂COCF₃ | |
| | d-50 | | | | —COCF₃ | —CH₂COCF₃ | |
| | d-51 | | | | | —CH₂COCH₃ | |
| | d-52 | | | | | —CH₂Ph | |
| | d-53 | | | | | —CH(CH₃)₂ | |
| | d-54 | | | | | —CH₂CO₂Me | |
| | d-55 | | | | | —CH₂CF₃ | |
| | d-56 | | | | —CONHMe | —CH₂COCF₃ | |
| | d-57 | | | | | —CH₂Br | |
| | d-58 | | | | —NHMe | —CH₂CN | |
| | d-59 | | | | | —Cl | |
| | d-60 | | | | —Cl | —CH₂CN | |
| | d-61 | | | | | —CH₂CF₃ | |
| | d-62 | | | | —Br | —CH₂Cl | |
| | d-63 | | | | | —CH₂COCF₃ | |
| | d-64 | | | | | —CH₂COCF₃ | |
| | d-65 | | | | —CN | —CH₂CF₃ | |
| | d-66 | | | | | —CH₂Cl | |
| | d-67 | | | | | —CH₂CO₂Me | |
| | d-68 | | | | —CF₃ | —CH₂COCF₃ | |
| | d-69 | | | | | —CH₂CF₃ | |
| | d-70 | | | | | —CH₂CN | |

TABLE 10-continued

Compound Structure with a General Formula Shown in Formula (d)

| Structural formula | Compound | R¹ | R² | R³ | R⁴ | R⁵ | R⁶ |
|---|---|---|---|---|---|---|---|
| | d-71 | | | | | —CH₂CO₂Me | |
| | d-72 | | | | —CO₂nBu | —CH₂CO₂nBu | |
| | d-73 | | | | —COOCH(CH₃)₂ | —COOCH(CH₃)₂ | |
| | d-74 | —CN | —SOCF₃ | H | H | —CO₂Me | |
| | d-75 | | | | | —CH₂CO₂Me | |
| | d-76 | | | | | —C(CO₂Me)CH₃ | |
| | d-77 | | | | | —CH₂CO₂CH₂CF₃ | |
| | d-78 | | | | | —CO₂CH₂CF₃ | |
| | d-79 | | | | | —CH₂CO₂CH(CF₃)2 | |
| | d-80 | | | | | —CH₂COCF₃ | |
| | d-81 | | | | | —COCF₃ | |
| | d-82 | | | | | —CN | |
| | d-83 | | | | | —CH₂CN | |
| | d-84 | | | | | —CF₃ | |
| | d-85 | | | | | —CH₂CF₃ | |
| | d-86 | | | | | —CONHMe | |
| | d-87 | | | | | —CH₂CONHCH₃ | |
| | d-88 | | | | | —CH₂COCH₃ | |
| | d-89 | | | | | —COCH₃ | |
| | d-90 | | | | | —Cl | |
| | d-91 | | | | | —Br | |
| | d-92 | | | | | —CH₂Cl | |
| | d-93 | | | | | —CH₂CH₂Cl | |
| | d-94 | | | | | —CH=CHCl | |
| | d-95 | | | | | —CH(CH₃)₂ | |
| | d-96 | | | | | —CH=CHCH₃ | |
| | d-97 | —CF₃ | —SOCF₃ | H | H | —CO₂Me | |
| | d-98 | | | | | —CH₂CO₂Me | |
| | d-99 | | | | | —C(CO₂Me)CH₃ | |
| | d-100 | | | | | —CH₂CO₂CH₂CF₃ | |
| | d-101 | | | | | —CO₂CH₂CF₃ | |
| | d-102 | | | | | —CH₂CO₂CH(CF₃)2 | |
| | d-103 | | | | | —CH₂COCF₃ | |
| | d-104 | | | | | —COCF₃ | |
| | d-105 | | | | | —CN | |
| | d-106 | | | | | —CH₂CN | |
| | d-107 | | | | | —CF₃ | |
| | d-108 | | | | | —CH₂CF₃ | |
| | d-109 | | | | | —CONHMe | |
| | d-110 | | | | | —CH₂CONHCH₃ | |
| | d-111 | | | | | —CH₂COCH₃ | |
| | d-112 | | | | | —COCH₃ | |
| | d-113 | | | | | —Cl | |
| | d-114 | | | | | —Br | |
| | d-115 | | | | | —CH₂Cl | |
| | d-116 | | | | | —CH₂CH₂Cl | |
| | d-117 | | | | | —CH=CHCl | |
| | d-118 | | | | | —CH(CH₃)₂ | |
| | d-119 | | | | | —CH=CHCH₃ | |
| | d-120 | —CN | —OCF₃ | H | H | —CO₂Me | |
| | d-121 | | | | | —CH₂CO₂Me | |
| | d-122 | | | | | —C(CO₂Me)CH₃ | |
| | d-123 | | | | | —CH₂CO₂CH₂CF₃ | |
| | d-124 | | | | | —CO₂CH₂CF₃ | |
| | d-125 | | | | | —CH₂CO₂CH(CF₃)2 | |
| | d-126 | | | | | —CH₂COCF₃ | |
| | d-127 | | | | | —COCF₃ | |
| | d-128 | | | | | —CN | |
| | d-129 | | | | | —CH₂CN | |
| | d-130 | | | | | —CF₃ | |
| | d-131 | | | | | —CH₂CF₃ | |
| | d-132 | | | | | —CONHMe | |
| | d-133 | | | | | —CH₂CONHCH₃ | |
| | d-134 | | | | | —CH₂COCH₃ | |
| | d-135- | | | | | —COCH₃ | |
| | d-136 | | | | | —Cl | |
| | d-137 | | | | | —Br | |
| | d-138 | | | | | —CH₂Cl | |
| | d-139 | | | | | —CH₂CH₂Cl | |
| | d-140 | | | | | —CH=CHCl | |
| | d-141 | | | | | —CH(CH₃)₂ | |
| | d-142 | | | | | —CH=CHCH₃ | |

Embodiment 8: Synthesis of Compounds e-1 to e-24 by Using a Method H

Method H:

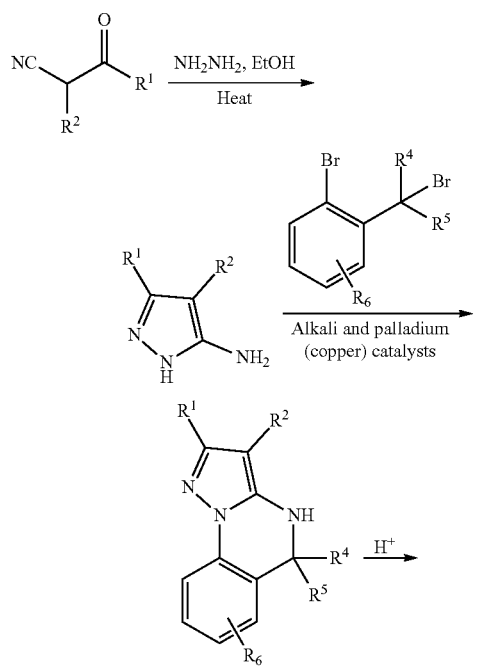

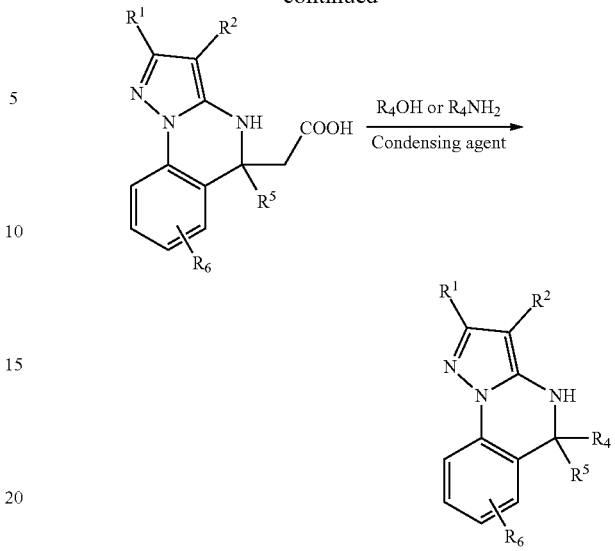

The compounds e-1 to e-24 were synthesized with the methods of the compound series c and (wherein cyclization steps also included similar cyclization methods mentioned in documents such as WO2016046404; WO2013174822; Synthetic Communications (2015) 45: 2426; Tetrahedron Letters (2014) 55: 4997; and WO2007149907), with a difference that different raw materials were selected for reaction according to different target compounds, or the compounds were derived from the synthesized target products through hydrolysis, simple esterification or amidation or reduction-oxidation. Specific compounds were as shown in Table 11.

TABLE 11

Compound Structure with a General Formula Shown in Formula (e)

| Structural formula | Compound | $R^1$ | $R^2$ | $R^3$ | $R^4$ | $R^5$ | $R^6$ |
|---|---|---|---|---|---|---|---|
| General formula (e) | e-1 | —CN | —SOCF$_3$ | H | —CO$_2$Me | —CH$_2$CO$_2$Me | 3-Cl, and 6-CF$_3$ |
| | e-2 | | | | | —CH$_2$CO$_2$Et | |
| | e-3 | | | | | —CH$_2$CO$_2$CH$_2$CF$_3$ | |
| | e-4 | | | | | —CH$_2$CO$_2$CH$_2$CHF$_2$ | |
| | e-5 | | | | —CO$_2$Et | —CH$_2$CO$_2$Et | |
| | e-6 | | | | | —CH$_2$CO$_2$Me | |
| | e-7 | —CN | —SOCF$_3$ | H | —CO$_2$Me | —CH$_2$CO$_2$Me | 3-Cl, and 4-CF$_3$ |
| | e-8 | | | | | —CH$_2$CO$_2$Et | |
| | e-9 | | | | | —CH$_2$CO$_2$CH$_2$CF$_3$ | |
| | e-10 | | | | | —CH$_2$CO$_2$CH$_2$CHF$_2$ | |
| | e-11 | | | | —CO$_2$Et | —CH$_2$CO$_2$Et | |
| | e-12 | | | | | —CH$_2$CO$_2$Me | |
| | e-13 | —CN | —SOCF$_3$ | H | —CO$_2$Me | —CH$_2$CO$_2$Me | 5-Cl, and 6-CF$_3$ |
| | e-14 | | | | | —CH$_2$CO$_2$Et | |
| | e-15 | | | | | —CH$_2$CO$_2$CH$_2$CF$_3$ | |
| | e-16 | | | | | —CH$_2$CO$_2$CH$_2$CHF$_2$ | |
| | e-17 | | | | —CO$_2$Et | —CH$_2$CO$_2$Et | |
| | e-18 | | | | | —CH$_2$CO$_2$Me | |
| | e-19 | —CN | —SOCF$_3$ | H | —CO$_2$Me | —CH$_2$CO$_2$Me | 4-Cl, and 5-CF$_3$ |
| | e-20 | | | | | —CH$_2$CO$_2$Et | |
| | e-21 | | | | | —CH$_2$CO$_2$CH$_2$CF$_3$ | |
| | e-22 | | | | | —CH$_2$CO$_2$CH$_2$CHF$_2$ | |
| | e-23 | | | | —CO$_2$Et | —CH$_2$CO$_2$Et | |
| | e-24 | | | | | —CH$_2$CO$_2$Me | |

Hydrogen spectrum and mass spectrum data of nuclear magnetic resonance of some compounds shown in the general formula (a) of Table 7 were shown in Table 12.

TABLE 12

Hydrogen Spectrum and Mass Spectrum Data of Nuclear Magnetic Resonance of Some Compounds Shown in General Formula (a)

| Compound | $^1$H-NMR(600 MHz) | MS (ESI) |
|---|---|---|
| a-1 | $^1$H NMR (600 MHz, CDCl$_3$) δ 8.35 (s, 1H), 7.56 (s, 1H), 7.45 (brs, 1H), 3.74 (s, 3H), 3.60(s, 3H), 3.33-3.25(m, 2H). | [M + H]$^+$ 512.1 |
| a-2 | $^1$H NMR (600 MHz, CDCl$_3$) δ 8.43 (s, 1H), 7.60 (s, 1H), 7.20 (brs, 1H), 3.61(s, 3H), 3.31-3.26(m, 2H). | [M + H]$^+$ 479.0 |
| a-3 | $^1$H NMR (600 MHz, CDCl$_3$) δ 8.36 (s, 1H), 7.50 (s, 1H), 7.49 (brs, 1H), 6.98 (brs, 2H), 3.74(s, 3H), 3.33-3.25(m, 2H). | [M + H]$^+$ 497.1 |
| a-4 | $^1$H NMR (600 MHz, CDCl$_3$) δ 8.35 (s, 1H), 7.55 (s, 1H), 7.49 (brs, 1H), 7.24 (brs, 1H), 3.74(s, 3H), 3.33-3.25(m, 2H), 2.80(s, 3H). | [M + H]$^+$ 510.9 |
| a-5 | $^1$H NMR (600 MHz, CDCl$_3$) δ 8.37 (s, 1H), 7.45 (s, 1H), 7.39 (brs, 1H), 4.34 (brs, 1H), 3.80(dd, J = 6.4, 2.0 Hz, 2H), 3.74(s, 3H), 3.34-3.25(dd, J = 6.4, 2.0 Hz, 2H). | [M + H]$^+$ 484.2 |
| a-6 | $^1$H NMR (600 MHz, CDCl$_3$) δ 8.37 (s, 1H), 7.45 (s, 1H), 7.39 (brs, 1H), 3.84 (s, 3H), 3.74(s, 3H), 3.25(dd, J = 5.4, 1.80 Hz, 1H), 1.14(d, J = 8.0, 3H). | [M + H]$^+$ 526.0 |
| a-7 | $^1$H NMR (600 MHz, CDCl$_3$) δ 8.35 (s, 1H), 7.56 (s, 1H), 3.74 (s, 3H), 3.60(s, 3H), 3.33-3.25(m, 2H), 3.04 (s, 3H). | [M + H]$^+$ 526.1 |
| a-8 | $^1$H NMR (600 MHz, CDCl$_3$) δ 8.35 (s, 1H), 7.56 (s, 1H), 3.74 (s, 3H), 3.60(s, 3H), 3.63-3.55(m, 2H), 3.53-3.48(m, 2H), 3.33-3.25(m, 2H). | [M + H]$^+$ 574.1 |
| a-9 | $^1$H NMR (600 MHz, CDCl$_3$) δ 8.37 (s, 1H), 7.45 (s, 1H), 7.39 (brs, 1H), 3.84 (dd, J = 5.4, 1.80 Hz, 2H), 3.74(s, 3H), 3.34-3.25(m, 2H), 1.14(t, J = 8.0, 3H). | [M + H]$^+$ 526.0 |
| a-10 | $^1$H NMR (600 MHz, CDCl$_3$) δ 8.36 (s, 1H), 8.15 (s, 1H), 7.54 (t, J = 2.3 Hz, 1H), 4.78-4.63 (m, 2H), 4.49-4.29 (m, 2H), 3.82 (d, J = 4.8 Hz, 3H), 3.71-3.46 (m, 2H). | [M + H]$^+$ 580.0 |
| a-11 | $^1$H NMR (600 MHz, CDCl$_3$) δ 8.34 (s, 1H), 7.59 (s, 1H), 6.92 (s, 1H), 5.87 (tdt, J = 54.7, 24.2, 3.9 Hz, 1H), 4.35-4.12 (m, 2H), 3.83 (d, J = 6.8 Hz, 3H), 3.63-3.35 (m, 2H). | [M + H]$^+$ 562.1 |
| a-12 | $^1$H NMR (600 MHz, CDCl$_3$) δ 8.16 (s, 1H), 7.61 (s, 1H), 6.95 (s, 1H), 5.69-5.59 (m, 1H), 3.85 (d, J = 21.5 Hz, 3H), 3.81-3.62 (m, 2H). | [M + H]$^+$ 648.2 |
| a-14 | $^1$H NMR (600 MHz, CDCl$_3$) δ 8.15 (d, J = 1.8 Hz, 1H), 7.60 (d, J = 1.3 Hz, 1H), 6.87 (s, 1H), 3.83 (s, 3H), 3.71-3.50 (m, 2H), 1.87 (s, 1H). | [M + H]$^+$ 662.2 |
| a-16 | $^1$H NMR (600 MHz, CDCl$_3$) δ 8.35 (s, 1H), 7.56 (s, 1H), 7.45 (brs, 1H), 7.23-7.19(m, 5H), 3.74 (s, 3H), 3.33-3.25(m, 2H). | [M + H]$^+$ 530.1 |
| a-17 | $^1$H NMR (600 MHz, CDCl$_3$) δ 8.35 (s, 1H), 7.56 (s, 1H), 7.45 (brs, 1H), 3.74 (s, 3H), 3.33-3.25(m, 2H), 2.10 (s, 3H). | [M + H]$^+$ 496.0 |
| a-18 | $^1$H NMR (600 MHz, CDCl$_3$) δ 8.35 (s, 1H), 7.56 (s, 1H), 7.45 (brs, 1H), 3.72 (s, 3H), 3.13-3.05(m, 2H). | [M + H]$^+$ 531.9 |
| a-19 | H NMR (600 MHz, CDCl$_3$) δ 8.35 (s, 1H), 7.56 (s, 1H), 7.45 (brs, 1H), 3.68 (s, 3H), 3.03-2.95(m, 2H). | [M + H]$^+$ 521.9 |
| a-20 | $^1$H NMR (600 MHz, CDCl$_3$) δ 8.35 (s, 1H), 7.56 (s, 1H), 7.45 (brs, 1H), 3.72 (s, 3H), 3.10-3.04(m, 2H). | [M + H]$^+$ 549.9 |
| a-21 | $^1$H NMR (600 MHz, CDCl$_3$) δ 8.07 (S, 1H), 7.57 (S, 1H), 7.40 (s, 1H), 3.80 (d, J = 16.4 Hz, 3H), 3.61 (d, J = 31.8 Hz, 3H), 3.51-3.40 (m, 1H), 3.46-3.29 (m, 1H), 3.20-2.98 (m, 2H), 1.38-1.29 (m, 3H). | [M + H]$^+$ 472.0 |
| a-22 | $^1$H NMR (600 MHz, CDCl$_3$) δ 8.10 (m, 1H), 7.57 (s, 1H), 7.27 (s, 1H), 4.38-4.21 (m, 2H), 4.15-4.00 (m, 2H), 3.69-3.30 (m, 2H), 1.25 (td, J = 7.1, 1.4 Hz, 3H), 1.17 (dt, J = 16.7, 7.1 Hz, 3H). | [M + H]$^+$ 540.0 |
| a-26 | $^1$H NMR (600 MHz, CDCl$_3$) δ 8.35 (s, 1H), 7.56 (s, 1H), 7.45 (brs, 1H), 3.33-3.25(m, 2H), 2.10 (s, 3H). | [M + H]$^+$ 534.0 |
| a-27 | $^1$H NMR (600 MHz, CDCl$_3$) δ 8.35 (s, 1H), 7.55 (s, 1H), 7.44 (brs, 1H), 7.23-7.19(m, 5H), 3.33-3.25(m, 2H). | [M + H]$^+$ 568.1 |
| a-28 | $^1$H NMR (600 MHz, CDCl$_3$) δ 8.38 (s, 1H), 7.53 (s, 1H), 7.45 (brs, 1H), 3.74 (s, 3H), 3.33-3.25(m, 2H). | [M + H]$^+$ 550.1 |
| a-29 | $^1$H NMR (600 MHz, CDCl$_3$) δ 8.36 (s, 1H), 7.49 (s, 1H), 7.46 (brs, 1H), 3.13-3.06(m, 2H). | [M + H]$^+$ 569.9 |
| a-30 | $^1$H NMR (600 MHz, CDCl$_3$) δ 8.39 (s, 1H), 7.56 (s, 1H), 7.45 (brs, 1H), 3.13-3.05(m, 2H). | [M + H]$^+$ 516.9 |
| a-36 | $^1$H NMR (600 MHz, CDCl$_3$) δ 8.39 (s, 1H), 7.53 (s, 1H), 7.40 (brs, 1H), 3.13-3.05(m, 2H), 2.40 (s, 3H). | [M + H]$^+$ 506.0 |
| a-37 | $^1$H NMR (600 MHz, CDCl$_3$) δ 8.37 (s, 1H), 7.46 (s, 1H), 7.39 (brs, 1H), 3.11-3.06(m, 2H), 2.38 (s, 3H). | [M + H]$^+$ 534.0 |
| a-44 | $^1$H NMR (600 MHz, CDCl$_3$) δ 8.35 (s, 1H), 7.56 (s, 1H), 7.45 (brs, 1H). | [M + H]$^+$ 449.9 |
| a-45 | $^1$H NMR (600 MHz, CDCl$_3$) δ 8.35 (s, 1H), 7.56 (s, 1H), 7.45 (brs, 1H), 3.13-3.05(m, 2H). | [M + H]$^+$ 507.8 |
| a-47 | $^1$H NMR (600 MHz, CDCl$_3$) δ 8.35 (s, 1H), 7.55 (s, 1H), 7.45 (brs, 1H), 3.10-3.02(m, 2H). | [M + H]$^+$ 544.8 |
| a-51 | $^1$H NMR (600 MHz, CDCl$_3$) δ 8.35 (s, 1H), 7.56 (s, 1H), 7.45 (brs, 1H),1.37 (s, 6H). | [M + H]$^+$ 409.9 |
| a-52 | $^1$H NMR (600 MHz, CDCl$_3$) δ 8.35 (s, 1H), 7.56 (s, 1H), 7.45 (brs, 1H). | [M + H]$^+$ 432.0 |
| a-53 | $^1$H NMR (600 MHz, CDCl$_3$) δ 8.33 (s, 1H), 7.50 (s, 1H), 7.40 (brs, 1H), 3.10-3.02(m, 2H). | [M + H]$^+$ 544.8 |
| a-56 | $^1$H NMR (600 MHz, CDCl$_3$) δ 8.35 (s, 1H), 7.56 (s, 1H), 7.45 (brs, 1H), 3.60(s, 3H), 3.33-3.25(m, 2H). | [M + H]$^+$ 479.1 |
| a-57 | $^1$H NMR (600 MHz, CDCl$_3$) δ 8.36 (s, 1H), 7.58 (s, 1H), 7.47 (brs, 1H), 3.13-3.05(m, 2H). | [M + H]$^+$ 517.1 |
| a-59 | $^1$H NMR (600 MHz, CDCl$_3$) δ 8.23 (s, 1H), 7.47 (s, 1H), 7.20 (brs, 1H), 3.00-2.92(m, 2H). | [M + H]$^+$ 488.8 |
| a-62 | $^1$H NMR (600 MHz, CDCl$_3$) δ 8.35 (s, 1H), 7.56 (s, 1H), 7.45 (brs, 1H), 3.60(s, 3H), 3.31-3.23(m, 2H). | [M + H]$^+$ 522.1 |
| a-63 | $^1$H NMR (600 MHz, CDCl$_3$) δ 8.33 (s, 1H), 7.55 (s, 1H), 7.40 (brs, 1H), 3.14-3.05(m, 2H). | [M + H]$^+$ 559.9 |
| a-64 | $^1$H NMR (600 MHz, CDCl$_3$) δ 8.35 (s, 1H), 7.56 (s, 1H), 7.45 (brs, 1H), 4.74 (s, 1H), 3.60(s, 3H). | [M + H]$^+$ 440.1 |

TABLE 12-continued

Hydrogen Spectrum and Mass Spectrum Data of Nuclear Magnetic Resonance of Some Compounds Shown in General Formula (a)

| Compound | $^1$H-NMR(600 MHz) | MS (ESI) |
|---|---|---|
| a-65 | $^1$H NMR (600 MHz, CDCl$_3$) δ 8.35 (s, 1H), 7.56 (s, 1H), 7.45 (brs, 1H), 4.74 (s, 1H), 3.60(s, 3H), 3.33-3.25(m, 2H). | [M + H]$^+$ 454.1 |
| a-71 | $^1$H NMR (600 MHz, CDCl$_3$) δ 8.35 (s, 1H), 7.58 (s, 1H), 7.43 (brs, 1H), 4.75 (s, 1H). | [M + H]$^+$ 477.9 |
| a-72 | $^1$H NMR (600 MHz, CDCl$_3$) δ 8.30 (s, 1H), 7.50 (s, 1H), 7.41 (brs, 1H), 4.65 (s, 1H). | [M + H]$^+$ 407.0 |
| a-80 | $^1$H NMR (600 MHz, CDCl$_3$) δ 8.38 (s, 1H), 7.61 (s, 1H), 7.38 (brs, 1H), 4.81 (s, 1H). | [M + H]$^+$ 415.9 |
| a-83 | $^1$H NMR (600 MHz, CDCl$_3$) δ 8.38 (s, 1H), 7.61 (s, 1H), 7.38 (brs, 1H), 4.81 (s, 1H), 3.63-3.55(m, 2H), 3.53-3.48(m, 2H). | [M + H]$^+$ 444.1 |
| a-86 | $^1$H NMR (600 MHz, CDCl$_3$) δ 8.39 (s, 1H), 7.58 (s, 1H), 7.48 (brs, 1H), 6.23(d, J = 8.3 Hz, 1H), 6.02(dd, J = 1.3, 8.3 Hz, 1H), 4.81 (s, 1H). | [M + H]$^+$ 441.9 |
| a-87 | $^1$H NMR (600 MHz, CDCl$_3$) δ 8.25 (s, 1H), 7.55 (s, 1H), 7.35 (brs, 1H), 4.74 (s, 1H), 3.60(s, 3H). | [M + H]$^+$ 483.1 |
| a-88 | $^1$H NMR (600 MHz, CDCl$_3$) δ 8.35 (s, 1H), 7.56 (s, 1H), 7.45 (brs, 1H), 4.74 (s, 1H), 3.60(s, 3H), 3.33-3.25(m, 2H). | [M + H]$^+$ 497.1 |
| a-95 | $^1$H NMR (600 MHz, CDCl$_3$) δ 8.30 (s, 1H), 7.50 (s, 1H), 7.41 (brs, 1H), 4.65 (s, 1H). | [M + H]$^+$ 449.9 |
| a-109 | $^1$H NMR (600 MHz, CDCl$_3$) δ 8.39 (s, 1H), 7.58 (s, 1H), 7.48 (brs, 1H), 6.23(d, J = 8.3 Hz, 1H), 6.02(dd, J = 1.3, 8.3 Hz, 1H), 4.81 (s, 1H), 1.63(d, J = 9.3 Hz, 3H). | [M + H]$^+$ 464.9 |
| a-111 | $^1$H NMR (600 MHz, CDCl$_3$) δ 8.36 (s, 1H), 7.56 (s, 1H), 7.45 (brs, 1H), 4.74 (s, 1H), 3.60(s, 3H), 3.32-3.25(m, 2H). | [M + H]$^+$ 422.1 |
| a-118 | $^1$H NMR (600 MHz, CDCl$_3$) δ 8.30 (s, 1H), 7.50 (s, 1H), 7.41 (brs, 1H), 4.65 (s, 1H). | [M + H]$^+$ 375.1 |
| a-122 | $^1$H NMR (600 MHz, CDCl$_3$) δ 8.35 (s, 1H), 7.65 (s, 1H), 7.50 (brs, 1H), 7.42 (brs, 1H), 4.65 (s, 1H), 2.82 (s, 3H). | [M + H]$^+$ 407.1 |
| a-132 | $^1$H NMR (600 MHz, CDCl$_3$) δ 8.40 (s, 1H), 7.58 (s, 1H), 7.48 (brs, 1H), 6.23(d, J = 8.3 Hz, 1H), 6.02(dd, J = 1.3, 8.3 Hz, 1H), 4.81 (s, 1H), 1.63(d, J = 9.3 Hz, 3H). | [M + H]$^+$ 389.9 |
| a-133 | $^1$H NMR (600 MHz, CDCl$_3$) δ 8.45 (s, 1H), 7.51 (s, 1H), 7.43 (brs, 1H), 3.76 (s, 3H), 3.61(s, 3H), 3.31-3.25(m, 2H). | [M + H]$^+$ 430.1 |
| a-134 | $^1$H NMR (600 MHz, CDCl$_3$) δ 8.35 (s, 1H), 7.56 (s, 1H), 7.45 (brs, 1H), 3.71 (s, 3H), 3.64(s, 3H), 3.32-3.26(m, 2H). | [M + H]$^+$ 464.1 |
| a-136 | $^1$H NMR (600 MHz, CDCl$_3$) δ 8.30 (s, 1H), 7.55 (s, 1H), 7.47 (brs, 1H), 3.74 (s, 3H), 3.66(s, 3H), 3.35-3.29(m, 2H). | [M + H]$^+$ 464.1 |

Hydrogen spectrum and mass spectrum data of nuclear magnetic resonance of some compounds shown in the general formula (b) of Table 8 were shown in Table 13.

TABLE 13

Hydrogen Spectrum and Mass Spectrum Data of Nuclear Magnetic Resonance of Some Compounds Shown in General Formula (b)

| Compound | $^1$H-NMR(600 MHz) | MS (ESI) |
|---|---|---|
| b-1 | $^1$H NMR (600 MHz, CDCl$_3$) δ 8.85 (s, 1H), 7.96 (s, 1H), 7.45 (brs, 1H), 3.74 (s, 3H), 3.60(s, 3H), 3.32-3.25(m, 2H). | [M + H]$^+$ 478.0 |
| b-2 | $^1$H NMR (600 MHz, CDCl$_3$) δ 8.86 (s, 1H), 7.97 (s, 1H), 7.21 (brs, 1H), 3.62(s, 3H), 3.31-3.27(m, 2H). | [M + H]$^+$ 445.0 |
| b-3 | $^1$H NMR (600 MHz, CDCl$_3$) δ 8.86 (s, 1H), 7.95 (s, 1H), 7.49 (brs, 1H), 6.28 (brs, 2H), 3.73(s, 3H), 3.33-3.26(m, 2H). | [M + H]$^+$ 463.1 |
| b-4 | $^1$H NMR (600 MHz, CDCl$_3$) δ 8.85 (s, 1H), 7.95 (s, 1H), 7.50 (brs, 1H), 7.25 (brs, 1H), 3.73(s, 3H), 3.35-3.26(m, 2H), 2.81(s, 3H). | [M + H]$^+$ 476.9 |
| b-5 | $^1$H NMR (600 MHz, CDCl$_3$) δ 8.87 (s, 1H), 7.85 (s, 1H), 7.49 (brs, 1H), 4.44 (brs, 1H), 3.81(dd, J = 6.4, 2.0 Hz, 2H), 3.77(s, 3H), 3.34-3.27(dd, J = 6.3, 2.1 Hz, 2H). | [M + H]$^+$ 450.1 |
| b-6 | $^1$H NMR (600 MHz, CDCl$_3$) δ 8.87 (s, 1H), 7.95 (s, 1H), 7.37 (brs, 1H), 3.85 (s, 3H), 3.75 (s, 3H), 3.25(dd, J = 5.5, 1.8 Hz, 1H), 1.15(d, J = 8.1, 3H). | [M + H]$^+$ 492.0 |
| b-7 | $^1$H NMR (600 MHz, CDCl$_3$) δ 8.85 (s, 1H), 7.96 (s, 1H), 3.76 (s, 3H), 3.61(s, 3H), 3.35-3.28(m, 2H), 3.06 (s, 3H). | [M + H]$^+$ 492.0 |
| b-8 | $^1$H NMR (600 MHz, CDCl$_3$) δ 8.86 (s, 1H), 7.98 (s, 1H), 3.75 (s, 3H), 3.59(s, 3H), 3.69-3.59(m, 2H), 3.54-3.48(m, 2H), 3.35-3.2(m, 2H). | [M + H]$^+$ 540.0 |
| b-9 | $^1$H NMR (600 MHz, CDCl$_3$) δ 8.89 (s, 1H), 7.47 (s, 1H), 7.34 (brs, 1H), 3.83 (dd, J = 5.4, 1.8 Hz, 2H), 3.76(s, 3H), 3.35-3.26(m, 2H), 1.13(t, J = 8.0, 3H). | [M + H]$^+$ 492.0 |
| b-10 | $^1$H NMR (600 MHz, CDCl$_3$) δ 8.86 (s, 1H), 8.15 (s, 1H), 7.54 (t, J = 2.5 Hz, 1H), 4.79-4.63 (m, 2H), 4.49-4.26 (m, 2H), 3.82 (d, J = 4.6 Hz, 3H), 3.72-3.46 (m, 2H). | [M + H]$^+$ 545.9 |
| b-11 | $^1$H NMR (600 MHz, CDCl$_3$) δ 8.84 (s, 1H), 7.99 (s, 1H), 6.95 (s, 1H), 5.89 (tdt, J = 54.7, 24.2, 3.9 Hz, 1H), 4.36-4.13 (m, 2H), 3.83 (d, J = 6.9 Hz, 3H), 3.64-3.35 (m, 2H). | [M + H]$^+$ 528.0 |
| b-12 | $^1$H NMR (600 MHz, CDCl$_3$) δ 8.96 (s, 1H), 7.67 (s, 1H), 6.96 (s, 1H), 5.68-5.57 (m, 1H), 3.85 (d, J = 22.5 Hz, 3H), 3.81-3.62 (m, 2H). | [M + H]$^+$ 613.9 |
| b-14 | $^1$H NMR (600 MHz, CDCl$_3$) δ 8.95 (d, J = 1.8 Hz, 1H), 7.90 (d, J = 1.3 Hz, 1H), 6.97 (s, 1H), 3.85 (s, 3H), 3.72-3.54 (m, 2H), 1.86 (s, 1H). | [M + H]$^+$ 628.0 |
| b-16 | $^1$H NMR (600 MHz, CDCl$_3$) δ 8.85 (s, 1H), 7.86 (s, 1H), 7.49 (brs, 1H), 7.22-7.18(m, 5H), 3.75 (s, 3H), 3.32-3.25(m, 2H). | [M + H]$^+$ 496.1 |
| b-17 | $^1$H NMR (600 MHz, CDCl$_3$) δ 8.95 (s, 1H), 7.58 (s, 1H), 7.46 (brs, 1H), 3.75 (s, 3H), 3.31-3.23(m, 2H), 2.13 (s, 3H). | [M + H]$^+$ 462.0 |
| b-18 | $^1$H NMR (600 MHz, CDCl$_3$) δ 8.95 (s, 1H), 7.86 (s, 1H), 7.44 (brs, 1H), 3.72 (s, 3H), 3.13-3.05(m, 2H). | [M + H]$^+$ 497.9 |
| b-19 | H NMR (600 MHz, CDCl$_3$) δ 8.86 (s, 1H), 7.77 (s, 1H), 7.51 (brs, 1H), 3.68 (s, 3H), 3.06-2.98(m, 2H). | [M + H]$^+$ 487.9 |
| b-20 | $^1$H NMR (600 MHz, CDCl$_3$) δ 8.95 (s, 1H), 7.86 (s, 1H), 7.45 (brs, 1H), 3.73 (s, 3H), 3.17-3.11(m, 2H). | [M + H]$^+$ 515.9 |
| b-21 | $^1$H NMR (600 MHz, CDCl$_3$) δ 8.97 (S, 1H), 7.97 (S, 1H), 7.48 (s, 1H), 3.81 (d, J = 16.5 Hz, 3H), 3.62 (d, J = 31.2 Hz, 3H), 3.50-3.40 (m, 1H), | [M + H]$^+$ 438.0 |

TABLE 13-continued

Hydrogen Spectrum and Mass Spectrum Data of Nuclear Magnetic Resonance of Some Compounds Shown in General Formula (b)

| Compound | $^1$H-NMR(600 MHz) | MS (ESI) |
|---|---|---|
| | 3.45-3.29 (m, 1H), 3.31-3.08 (m, 2H), 1.39-1.30 (m, 3H). | |
| b-23 | $^1$H NMR (600 MHz, CDCl$_3$) δ 8.93 (s, 1H), 7.97 (d, J = 1.9 Hz, 1H), 6.86 (brs, 1H), 4.40-4.20 (m, 2H), 3.63 (s, 3H), 3.53-3.31 (m, 2H), 1.25 (td, J = 7.2, 3.0 Hz, 3H). | [M + H]$^+$ 491.1 |
| b-25 | $^1$H NMR (600 MHz, CDCl$_3$) δ 8.93 (s, 1H), 7.97 (d, J = 1.9 Hz, 1H), 6.86 (brs, 1H), 4.30-4.10 (m, 2H). | [M + H]$^+$ 553.9 |
| b-27 | $^1$H NMR (600 MHz, CDCl$_3$) δ 8.99 (s, 1H), 7.95 (s, 1H), 7.44 (brs, 1H), 7.23-7.19(m, 5H), 3.35-3.25(m, 2H). | [M + H]$^+$ 534.0 |
| b-28 | $^1$H NMR (600 MHz, CDCl$_3$) δ 8.98 (s, 1H), 7.93 (s, 1H), 7.45 (brs, 1H), 3.75 (s, 3H), 3.33-3.25(m, 2H). | [M + H]$^+$ 515.9 |
| b-30 | $^1$H NMR (600 MHz, CDCl$_3$) δ 8.99 (s, 1H), 7.86 (s, 1H), 7.46 (brs, 1H), 3.13-3.05(m, 2H). | [M + H]$^+$ 482.9 |
| b-34 | $^1$H NMR (600 MHz, CDCl$_3$) δ 8.99 (s, 1H), 7.83 (s, 1H), 7.41 (brs, 1H), 3.14-3.06(m, 2H), 2.44 (s, 3H). | [M + H]$^+$ 481.9 |
| b-37 | $^1$H NMR (600 MHz, CDCl$_3$) δ 8.97 (s, 1H), 7.86 (s, 1H), 7.39 (brs, 1H), 3.11-3.06(m, 2H), 2.9 (s, 3H). | [M + H]$^+$ 499.9 |
| b-43 | $^1$H NMR (600 MHz, CDCl$_3$) δ 8.85 (s, 1H), 7.76 (s, 1H), 7.45 (brs, 1H), 5.45 (brs, 1H), 3.37 (s, 3H), 3.01-2.96(m, 2H). | [M + H]$^+$ 416.0 |
| b-47 | $^1$H NMR (600 MHz, CDCl$_3$) δ 8.95 (s, 1H), 7.85 (s, 1H), 7.40 (brs, 1H), 3.18-3.09(m, 2H). | [M + H]$^+$ 420.9 |
| b-48 | $^1$H NMR (600 MHz, CDCl$_3$) δ 8.95 (s, 1H), 7.85 (s, 1H), 7.40 (brs, 1H), 3.01-2.89(m, 2H). | [M + H]$^+$ 463.9 |
| b-50 | $^1$H NMR (600 MHz, CDCl$_3$) δ 8.89 (s, 1H), 7.75 (s, 1H), 7.32 (brs, 1H), 2.91-2.79(m, 2H). | [M + H]$^+$ 535.8 |
| b-54 | $^1$H NMR (600 MHz, CDCl$_3$) δ 8.85 (s, 1H), 7.70 (s, 1H), 7.30 (brs, 1H), 2.81-2.68(m, 2H). | [M + H]$^+$ 454.9 |
| b-56 | $^1$H NMR (600 MHz, CDCl$_3$) δ 8.95 (s, 1H), 7.86 (s, 1H), 7.45 (brs, 1H), 3.61(s, 3H), 3.35-3.25(m, 2H). | [M + H]$^+$ 445.0 |
| b-57 | $^1$H NMR (600 MHz, CDCl$_3$) δ 8.96 (s, 1H), 7.78 (s, 1H), 7.49 (brs, 1H), 3.14-3.05(m, 2H). | [M + H]$^+$ 482.9 |
| b-59 | $^1$H NMR (600 MHz, CDCl$_3$) δ 8.93 (s, 1H), 7.77 (s, 1H), 7.21 (brs, 1H), 3.01-2.95(m, 2H). | [M + H]$^+$ 454.9 |
| b-62 | $^1$H NMR (600 MHz, CDCl$_3$) δ 8.95 (s, 1H), 7.76 (s, 1H), 7.47 (brs, 1H), 3.61(s, 3H), 3.31-3.23(m, 2H). | [M + H]$^+$ 487.9 |
| b-63 | $^1$H NMR (600 MHz, CDCl$_3$) δ 8.93 (s, 1H), 7.75 (s, 1H), 7.42 (brs, 1H), 3.15-3.07(m, 2H). | [M + H]$^+$ 525.9 |
| b-66 | $^1$H NMR (600 MHz, CDCl$_3$) δ 8.87 (s, 1H), 7.95 (s, 1H), 7.37 (brs, 1H), 4.74 (s, 1H), 3.75(s, 3H), 3.25(dd, J = 5.5, 1.9 Hz, 1H), 1.15(d, J = 8.1, 3H). | [M + H]$^+$ 434.0 |
| b-68 | $^1$H NMR (600 MHz, CDCl$_3$) δ 8.80 (s, 1H), 7.90 (s, 1H), 7.41 (brs, 1H), 4.65 (m, 1H), 4.47 (s, 2H), 2.95-2.77(m, 2H). | [M + H]$^+$ 487.9 |
| b-70 | $^1$H NMR (600 MHz, CDCl$_3$) δ 8.81 (s, 1H), 7.91 (s, 1H), 7.42 (brs, 1H), 4.65 (m, 1H), 2.95-2.77(m, 2H). | [M + H]$^+$ 457.9 |
| b-73 | $^1$H NMR (600 MHz, CDCl$_3$) δ 8.82 (s, 1H), 7.92 (s, 1H), 7.41 (brs, 1H), 4.65 (m, 1H), 2.93-2.73(m, 2H). | [M + H]$^+$ 386.9 |
| b-80 | $^1$H NMR (600 MHz, CDCl$_3$) δ 8.89 (s, 1H), 7.95 (s, 1H), 7.42 (brs, 1H), 4.66 (m, 1H). | [M + H]$^+$ 381.9 |
| b-86 | $^1$H NMR (600 MHz, CDCl$_3$) δ 8.89 (s, 1H), 7.98 (s, 1H), 7.49 (brs, 1H), 6.24(d, J = 8.4 Hz, 1H), 6.03(dd, J = 1.4, 8.4 Hz, 1H), 4.82 (s, 1H). | [M + H]$^+$ 388.0 |
| b-87 | $^1$H NMR (600 MHz, CDCl$_3$) δ 8.85 (s, 1H), 7.95 (s, 1H), 7.41 (brs, 1H), 4.75 (s, 1H), 3.60(s, 3H). | [M + H]$^+$ 448.9 |
| b-88 | $^1$H NMR (600 MHz, CDCl$_3$) δ 8.85 (s, 1H), 7.96 (s, 1H), 7.45 (brs, 1H), 4.76 (s, 1H), 3.61(s, 3H), 3.34-3.26(m, 2H). | [M + H]$^+$ 462.9 |
| b-94 | $^1$H NMR (600 MHz, CDCl$_3$) δ 8.80 (s, 1H), 7.80 (s, 1H), 7.47 (brs, 1H), 4.66 (s, 1H). | [M + H]$^+$ 486.9 |
| b-99 | $^1$H NMR (600 MHz, CDCl$_3$) δ 8.81 (s, 1H), 7.82 (s, 1H), 7.27 (brs, 1H), 5.27 (brs, 1H), 4.66 (s, 1H), 2.86 (s, 3H). | [M + H]$^+$ 447.9 |
| b-104 | $^1$H NMR (600 MHz, CDCl$_3$) δ 8.80 (s, 1H), 7.78 (s, 1H), 7.38 (brs, 1H), 4.89 (s, 1H). | [M + H]$^+$ 468.8 |
| b-111 | $^1$H NMR (600 MHz, CDCl$_3$) δ 8.86 (s, 1H), 7.86 (s, 1H), 7.41 (brs, 1H), 4.68 (s, 1H), 3.61(s, 3H), 3.33-3.28(m, 2H). | [M + H]$^+$ 388.0 |
| b-116 | $^1$H NMR (600 MHz, CDCl$_3$) δ 8.83 (s, 1H), 8.01 (s, 1H), 7.39 (brs, 1H), 4.66 (m, 1H), 2.96-2.77(m, 2H). | [M + H]$^+$ 426.0 |
| b-118 | $^1$H NMR (600 MHz, CDCl$_3$) δ 8.90 (s, 1H), 7.80 (s, 1H), 7.37 (brs, 1H), 4.65 (s, 1H). | [M + H]$^+$ 341.0 |
| b-123 | $^1$H NMR (600 MHz, CDCl$_3$) δ 8.95 (s, 1H), 7.95 (s, 1H), 7.42 (brs, 1H), 7.36 (brs, 1H), 4.75 (s, 1H), 3.11-3.06(m, 2H), 2.82 (s, 3H). | [M + H]$^+$ 387.0 |
| b-131 | $^1$H NMR (600 MHz, CDCl$_3$) δ 8.87 (s, 1H), 7.91 (s, 1H), 7.42 (brs, 1H), 4.75 (d, J = 8.1, 1H), 2.11-2.06(m, 1H), 0.92 (d, J = 10.1, 6H). | [M + H]$^+$ 358.0 |
| b-134 | $^1$H NMR (600 MHz, CDCl$_3$) δ 8.85 (s, 1H), 7.96 (s, 1H), 7.45 (brs, 1H), 3.71 (s, 3H), 3.64(s, 3H), 3.32-3.26(m, 2H). | [M + H]$^+$ 430.1 |
| b-135 | $^1$H NMR (600 MHz, CDCl$_3$) δ 8.89 (s, 1H), 7.96 (s, 1H), 7.43 (brs, 1H), 3.73 (s, 3H), 3.63(s, 3H), 3.31-3.27(m, 2H). | [M + H]$^+$ 446.0 |
| b-136 | $^1$H NMR (600 MHz, CDCl$_3$) δ 8.90 (s, 1H), 7.95 (s, 1H), 7.47 (brs, 1H), 3.74 (s, 3H), 3.66(s, 3H), 3.35-3.29(m, 2H). | [M + H]$^+$ 430.0 |
| b-138 | $^1$H NMR (600 MHz, CDCl$_3$) δ 8.87(s, 1H), 7.96 (s, 1H), 7.43 (brs, 1H), 3.72 (s, 3H), 3.66(s, 3H), 3.32-3.26(m, 2H). | [M + H]$^+$ 521.1 |

Hydrogen spectrum and mass spectrum data of nuclear magnetic resonance of some compounds shown in the general formula (c) of Table 9 were shown in Table 14.

TABLE 14

Hydrogen Spectrum and Mass Spectrum Data of Nuclear Magnetic Resonance of Some Compounds Shown in General Formula (c)

| Compound | $^1$H-NMR(600 MHz) | MS (ESI) |
|---|---|---|
| c-2 | $^1$H NMR (600 MHz, CDCl$_3$) δ 8.14 (s, 1H), 7.57 (s, 1H), 7.05 (s, 1H), 3.82 (s, 3H), 3.64 (s, 3H), 3.57-3.25 (m, 2H). | [M + H]$^+$ 497.1 |
| c-4 | $^1$H NMR (600 MHz, CDCl$_3$) δ 8.15 (s, 1H), 7.60 (s, 1H), 7.05 (brs, 1H), 3.82 (s, 3H), 3.64 (s, 3H), 3.57-3.25 (m, 2H). | [M + H]$^+$ 497.2 |
| c-7 | $^1$H NMR (600 MHz, CDCl$_3$) δ 8.20 (s, 1H), 7.60 (s, 1H), 7.05 (brs, 1H), 3.82 (s, 3H), 3.64 (s, 3H), 3.57-3.25 (m, 2H). | [M + H]$^+$ 587.9 |
| c-8 | $^1$H NMR (600 MHz, CDCl$_3$) δ 8.13 (s, 1H), 7.58 (s, 1H), 7.28 (s, 1H), 3.82 | [M + H]$^+$ 544.9 |

TABLE 14-continued

Hydrogen Spectrum and Mass Spectrum Data of Nuclear Magnetic Resonance of Some Compounds Shown in General Formula (c)

| Compound | $^1$H-NMR(600 MHz) | MS (ESI) |
|---|---|---|
| | (s, 3H), 3.66 (s, 3H), 3.55-3.23 (m, 2H). $^1$H NMR (600 MHz, CDCl$_3$) δ 8.14 (s, 1H), 7.57 (s, 1H), 6.82 (s, 1H), 3.82 (s, 3H), 3.62 (s, 3H), 3.49 (d, J = 1.5 Hz, 2H). | |
| c-14 | $^1$H NMR (600 MHz, CDCl$_3$) δ 8.15 (s, 1H), 7.56 (s, 1H), 3.84 (s, 3H), 3.60(s, 3H), 3.33-3.25(m, 2H), 3.04 (s, 3H). | [M + H]$^+$ 559.1 |
| c-15 | $^1$H NMR (600 MHz, CDCl$_3$) δ 8.15 (s, 1H), 7.56 (s, 1H), 3.84 (s, 3H), 3.60(s, 3H), 3.33-3.25(m, 2H), 2.12 (s, 3H). | [M + H]$^+$ 587.1 |
| c-17 | $^1$H NMR (600 MHz, CDCl$_3$) δ 8.13 (d, J = 1.3 Hz, 1H), 7.57 (d, J = 1.2 Hz, 1H), 6.84 (s, 1H), 4.11-3.99 (m, 2H), 3.81 (s, 3H), 3.48 (d, J = 2.2 Hz, 2H), 1.16 (t, J = 7.1 Hz, 3H). | [M + H]$^+$ 559.0 |
| c-18 | $^1$H NMR (600 MHz, CDCl$_3$) δ 8.12 (d, J = 1.8 Hz, 1H), 7.57 (d, J = 1.8 Hz, 1H), 7.03 (s, 1H), 3.81 (s, 3H), 3.59-3.33 (m, 2H), 2.27 (s, 1H). | [M + H]$^+$ 530.9 |
| c-19 | $^1$H NMR (600 MHz, CDCl$_3$) δ 8.18-8.13 (m, 1H), 7.66-7.56 (m, 1H), 6.87 (s, 1H), 4.48-4.31 (m, 2H), 3.83 (d, J = 6.7 Hz, 3H), 3.70-3.48 (m, 2H). | [M + H]$^+$ 612.9 |
| c-20 | $^1$H NMR (600 MHz, CDCl$_3$) δ 8.14 (dd, J = 4.8, 1.7 Hz, 1H), 7.59 (d, J = 0.3 Hz, 1H), 5.87 (tdt, J = 54.7, 23.8, 3.9 Hz, 1H), 4.33-4.14 (m, 2H), 3.83 (d, J = 7.3 Hz, 3H), 3.60-3.37 (m, 2H). | [M + H]$^+$ 595.0 |
| c-21 | $^1$H NMR (600 MHz, CDCl$_3$) δ 8.16 (s, 1H), 7.61 (s, 1H), 6.95 (s, 1H), 5.69-5.59 (m, 1H), 3.85 (d, J = 21.5 Hz, 3H), 3.81-3.62 (m, 2H). | [M + H]$^+$ 680.9 |
| c-25 | $^1$H NMR (600 MHz, CDCl$_3$) δ 8.13 (dd, J = 4.9, 1.8 Hz, 1H), 7.57 (d, J = 1.8 Hz, 1H), 6.86 (s, 1H), 4.40-4.20 (m, 2H), 3.63 (d, J = 23.3 Hz, 3H), 3.53-3.31 (m, 2H), 1.25 (td, J = 7.1, 3.0 Hz, 3H). | [M + H]$^+$ 559.0 |
| c-26 | $^1$H NMR (600 MHz, CDCl$_3$) δ 8.15-8.10 (m, 1H), 7.57 (s, 1H), 7.27 (s, 1H), 4.38-4.21 (m, 2H), 4.15-4.00 (m, 2H), 3.69-3.30 (m, 2H), 1.25 (td, J = 7.1, 1.4 Hz, 3H), 1.17 (dt, J = 16.7, 7.1 Hz, 3H). | [M + H]$^+$ 572.9 |
| c-28 | $^1$H NMR (600 MHz, CDCl$_3$) δ 8.15 (dd, J = 4.5, 1.8 Hz, 1H), 7.65-7.57 (m, 1H), 6.84 (s, 1H), 4.48-4.22 (m, 4H), 3.71-3.46 (m, 2H), 1.25 (td, J = 7.1, 1.1 Hz, 3H). | [M + H]$^+$ 627.0 |
| c-29 | $^1$H NMR (600 MHz, CDCl$_3$) δ 8.14 (dd, J = 4.1, 1.8 Hz, 1H), 7.59 (t, J = 2.4 Hz, 1H), 5.88 (tdt, J = 54.7, 26.4, 3.9 Hz, 1H), 4.43-4.16 (m, 4H), 3.60-3.35 (m, 2H), 1.25 (t, J = 7.1 Hz, 3H). | [M + H]$^+$ 609.0 |
| c-34 | $^1$H NMR (600 MHz, CDCl$_3$) δ 8.15 (s, 1H), 7.56 (s, 1H), 7.45 (brs, 1H), 3.33-3.25(m, 2H). | [M + H]$^+$ 620.9 |
| c-36 | $^1$H NMR (600 MHz, CDCl$_3$) δ 8.15 (s, 1H), 7.55 (s, 1H), 7.44 (brs, 1H), 7.23-7.19(m, 5H), 3.33-3.25(m, 2H). | [M + H]$^+$ 601.0 |
| c-39 | $^1$H NMR (600 MHz, CDCl$_3$) δ 8.15 (s, 1H), 7.55 (s, 1H), 7.44 (brs, 1H), 2.43(s, 3H). | [M + H]$^+$ 552.9 |
| c-42 | $^1$H NMR (600 MHz, CDCl$_3$) δ 8.18 (s, 1H), 7.61 (s, 1H), 7.38 (brs, 1H), 3.63-3.55(m, 2H), 3.53-3.48(m, 2H). | [M + H]$^+$ 572.9 |
| c-47 | $^1$H NMR (600 MHz, CDCl$_3$) δ 8.18 (s, 1H), 7.61 (s, 1H), 7.38 (brs, 1H), 3.53-3.48(m, 2H), 2.49 (s, 3H). | [M + H]$^+$ 566.9 |
| c-53 | $^1$H NMR (600 MHz, CDCl$_3$) δ 8.20 (s, 1H), 7.61 (s, 1H), 7.38 (brs, 1H), 3.59 (s, 3H), 2.49 (s, 3H). | [M + H]$^+$ 514.9 |
| c-54 | $^1$H NMR (600 MHz, CDCl$_3$) δ 8.18 (s, 1H), 7.61 (s, 1H), 7.38 (brs, 1H), 3.23-3.19(m, 2H), 2.49 (s, 3H). | [M + H]$^+$ 549.0 |
| c-57 | $^1$H NMR (600 MHz, CDCl$_3$) δ 8.18 (s, 1H), 7.61 (s, 1H), 7.38 (brs, 1H), 3.13-3.08(m, 2H), 2.49 (s, 3H). | [M + H]$^+$ 495.9 |
| c-61 | $^1$H NMR (600 MHz, CDCl$_3$) δ 8.13 (d, J = 1.3 Hz, 1H), 7.57 (d, J = 1.2 Hz, 1H), 7.35-7.19 (m, 5H), 6.84 (s, 1H), 3.81 (s, 3H), 3.53-3.38(m, 2H). | [M + H]$^+$ 563.1 |
| c-64 | $^1$H NMR (600 MHz, CDCl$_3$) δ 8.15 (d, J = 1.5 Hz, 1H), 7.57 (d, J = 1.2 Hz, 1H), 6.84 (s, 1H), 3.81 (s, 3H), 3.33-3.20(m, 2H). | [M + H]$^+$ 564.9 |
| c-67 | $^1$H NMR (600 MHz, CDCl$_3$) δ 8.16 (d, J = 1.8 Hz, 1H), 7.57 (d, J = 1.2 Hz, 1H), 6.84 (s, 1H). | [M + H]$^+$ 497.9 |
| c-72 | $^1$H NMR (600 MHz, CDCl$_3$) δ 8.06 (d, J = 2.0 Hz, 1H), 7.67 (d, J = 1.2 Hz, 1H), 7.54 (s, 1H), 6.84 (s, 1H), 2.94 (s, 3H), 2.46 (s, 3H). | [M + H]$^+$ 512.9 |
| c-73 | $^1$H NMR (600 MHz, CDCl$_3$) δ 8.06 (d, J = 2.0 Hz, 1H), 7.67 (d, J = 1.2 Hz, 1H), 7.54 (s, 1H), 6.84 (s, 1H), 3.74 (s, 3H), 2.86 (s, 3H). | [M + H]$^+$ 530.0 |
| c-77 | $^1$H NMR (600 MHz, CDCl$_3$) δ 8.06 (d, J = 2.0 Hz, 1H), 7.67 (d, J = 1.2 Hz, 1H), 7.54 (s, 1H), 6.84 (s, 1H), 2.86 (s, 3H). | [M + H]$^+$ 550.0 |
| c-80 | $^1$H NMR (600 MHz, CDCl$_3$) δ 8.07 (d, J = 2.0 Hz, 1H), 7.68 (d, J = 1.2 Hz, 1H), 7.54 (s, 1H), 6.84 (s, 1H), 2.87 (s, 3H). | [M + H]$^+$ 496.9 |
| c-84 | $^1$H NMR (600 MHz, CDCl$_3$) δ 8.06 (d, J = 2.0 Hz, 1H), 7.68 (d, J = 1.2 Hz, 1H), 7.54 (s, 1H), 6.84 (s, 1H), 3.13-3.08(m, 2H), 2.87 (s, 3H). | [M + H]$^+$ 581.9 |
| c-86 | $^1$H NMR (600 MHz, CDCl$_3$) δ 8.07 (d, J = 2.0 Hz, 1H), 7.68 (d, J = 1.2 Hz, 1H), 6.84 (s, 1H). | [M + H]$^+$ 451.0 |
| c-91 | $^1$H NMR (600 MHz, CDCl$_3$) δ 8.06 (d, J = 2.0 Hz, 1H), 7.68 (d, J = 1.2 Hz, 1H), 6.88 (s, 1H), 3.10-3.05(m, 2H). | [M + H]$^+$ 487.9 |
| c-93 | $^1$H NMR (600 MHz, CDCl$_3$) δ 8.06 (d, J = 2.0 Hz, 1H), 7.68 (d, J = 1.2 Hz, 1H), 6.88 (s, 1H), 2.50-2.35(m, 2H). | [M + H]$^+$ 530.9 |
| c-97 | $^1$H NMR (600 MHz, CDCl$_3$) δ 8.09 (d, J = 2.0 Hz, 1H), 7.68 (d, J = 1.2 Hz, 1H), 6.88 (s, 1H). | [M + H]$^+$ 588.8 |
| c-98 | $^1$H NMR (600 MHz, CDCl$_3$) δ 8.19 (d, J = 2.0 Hz, 1H), 7.70 (d, J = 1.2 Hz, 1H), 6.88 (s, 1H), 1.38 (s, 6H). | [M + H]$^+$ 443.1 |
| c-101 | $^1$H NMR (600 MHz, CDCl$_3$) δ 8.06 (d, J = 2.0 Hz, 1H), 7.68 (d, J = 1.2 Hz, 1H), 6.89 (s, 1H), 3.11-3.05(m, 2H). | [M + H]$^+$ 478.8 |
| c-105 | $^1$H NMR (600 MHz, CDCl$_3$) δ 8.06 (d, J = 2.0 Hz, 1H), 7.68 (d, J = 1.2 Hz, 1H), 6.89 (s, 1H), 3.87 (s, 3H), 3.11-3.05(m, 2H). | [M + H]$^+$ 512.1 |
| c-107 | $^1$H NMR (600 MHz, CDCl$_3$) δ 8.11 (d, J = 2.0 Hz, 1H), 7.68 (d, J = 1.2 Hz, 1H), 6.58 (s, 1H). | [M + H]$^+$ 535.9 |
| c-110 | $^1$H NMR (600 MHz, CDCl$_3$) δ 8.07 (d, J = 2.0 Hz, 1H), 7.68 (d, J = 1.2 Hz, 1H), 6.89 (s, 1H), 2.91-2.75(m, 2H). | [M + H]$^+$ 565.1 |
| c-111 | $^1$H NMR (600 MHz, CDCl$_3$) δ 8.08 (d, J = 2.0 Hz, 1H), 7.68 (d, J = 1.2 Hz, 1H), 6.95 (s, 1H), 3.11-2.95(m, 2H). | [M + H]$^+$ 520.9 |
| c-114 | $^1$H NMR (600 MHz, CDCl$_3$) δ 8.10 (d, J = 2.0 Hz, 1H), 7.68 (d, J = 1.2 Hz, 1H), 6.95 (s, 1H), 2.45(s, 3H). | [M + H]$^+$ 524.9 |
| c-117 | $^1$H NMR (600 MHz, CDCl$_3$) δ 8.15 (s, 1H), 7.59(s, 1H), 6.88 (s, 0H), 4.24-4.19 (m, 2H), 4.08-3.93 (m, 2H), 3.57-3.45 (m, 1H), 3.48-3.32 (m, 1H), 1.62-1.53 (m, 2H), 1.50 (dddd, J = 13.7, | [M + H]$^+$ 629.0 |

TABLE 14-continued

Hydrogen Spectrum and Mass Spectrum Data of Nuclear Magnetic Resonance of Some Compounds Shown in General Formula (c)

| Compound | ¹H-NMR(600 MHz) | MS (ESI) |
|---|---|---|
| | 6.9, 3.5, 2.3 Hz, 2H), 1.31-1.19 (m, 4H), 1.01-0.81 (m, 6H). | |
| c-118 | ¹H NMR (600 MHz, CDCl₃) δ 8.18 (s, 1H), 7.57 (s, 1H), 7.45 (s, 1H), 3.80 (d, J = 16.4 Hz, 3H), 3.61 (d, J = 31.8 Hz, 3H), 3.51-3.40 (m, 1H), 3.46-3.29 (m, 1H), 3.20-2.98 (m, 2H), 1.38-1.29 (m, 3H). | [M + H]⁺ 505.0 |
| c-123 | ¹H NMR (600 MHz, CDCl₃) δ 8.10 (d, J = 2.0 Hz, 1H), 7.68 (d, J = 1.2 Hz, 1H), 6.95 (s, 1H), 4.89 (s, 1H), 4.45(dd, J = 4.8, 1.7 Hz, 2H). | [M + H]⁺ 540.9 |
| c-126 | ¹H NMR (600 MHz, CDCl₃) δ 8.11 (d, J = 2.0 Hz, 1H), 7.69 (d, J = 1.2 Hz, 1H), 6.95 (s, 1H), 4.89 (s, 1H). | [M + H]⁺ 510.9 |
| c-128 | ¹H NMR (600 MHz, CDCl₃) δ 8.15 (s, 1H), 7.69 (s, 1H), 6.95 (brs, 1H), 3.74 (d, J = 6.9 Hz, 1H), 2.33-2.25(m, 2H). | [M + H]⁺ 453.9 |
| c-135 | ¹H NMR (600 MHz, CDCl₃) δ 8.15 (s, 1H), 7.61 (s, 1H), 6.39 (brs, 1H), 4.71 (s, 1H). | [M + H]⁺ 448.9 |
| c-139 | ¹H NMR (600 MHz, CDCl₃) δ 8.16(s, 1H), 7.61 (s, 1H), 6.79 (brs, 1H), 6.59 (dd, J = 12.8, 8.9 Hz, 1H), 6.09 (d, J = 8.9 Hz, 1H), 4.71 (d, J = 6.9 Hz, 1H). | [M + H]⁺ 474.9 |
| c-149 | ¹H NMR (600 MHz, CDCl₃) δ 8.15 (d, J = 2.0 Hz, 1H), 7.69 (d, J = 1.2 Hz, 1H), 6.95 (s, 1H), 4.90 (s, 1H). | [M + H]⁺ 553.9 |
| c-150 | ¹H NMR (600 MHz, CDCl₃) δ 8.20 (d, J = 2.0 Hz, 1H), 7.69 (d, J = 1.2 Hz, 1H), 6.35 (s, 1H), 4.91 (s, 1H). | [M + H]⁺ 483.0 |
| c-152 | ¹H NMR (600 MHz, CDCl₃) δ 8.10 (d, J = 2.0 Hz, 1H), 7.65 (d, J = 1.2 Hz, 1H), 6.25 (s, 1H), 4.71 (s, 1H). | [M + H]⁺ 525.9 |
| c-154 | ¹H NMR (600 MHz, CDCl₃) δ 8.10 (d, J = 2.0 Hz, 1H), 7.65 (d, J = 1.2 Hz, 1H), 6.75 (brs, 1H), 6.25 (brs, 1H), 4.70 (s, 1H), 2.93 (s, 3H). | [M + H]⁺ 514.9 |
| c-166 | ¹H NMR (600 MHz, CDCl₃) δ 8.16 (d, J = 2.0 Hz, 1H), 7.68 (d, J = 1.4 Hz, 1H), 6.89 (s, 1H), 3.87 (s, 3H), 3.11-3.05(m, 2H). | [M + H]⁺ 455.0 |
| c-169 | ¹H NMR (600 MHz, CDCl₃) δ 8.06 (d, J = 2.0 Hz, 1H), 7.68 (d, J = 1.4 Hz, 1H), 6.89 (s, 1H), 4.87 (d, J = 12.0 Hz, 1H), 4.67-4.60 (m, 2H), 3.11-3.05(m, 2H). | [M + H]⁺ 523.0 |
| c-173 | ¹H NMR (600 MHz, CDCl₃) δ 8.05 (d, J = 2.0 Hz, 1H), 7.69 (d, J = 1.2 Hz, 1H), 6.95 (s, 1H), 4.91 (s, 1H). | [M + H]⁺ 408.0 |
| c-180 | ¹H NMR (600 MHz, CDCl₃) δ 8.09 (d, J = 2.0 Hz, 1H), 7.68 (d, J = 1.4 Hz, 1H), 6.89 (s, 1H), 4.87 (d, J = 12.0 Hz, 1H), 3.11-3.05(m, 2H), 2.05(s, 2H). | [M + H]⁺ 439.0 |
| c-188 | ¹H NMR (600 MHz, CDCl₃) δ 8.03 (s, 1H), 7.88 (s, 1H), 7.28 (s, 1H), 3.82 (s, 3H), 3.66 (s, 3H), 3.55-3.23 (m, 2H). | [M + H]⁺ 589.0 |
| c-196 | ¹H NMR (600 MHz, CDCl₃) δ 8.08-8.13 (m, 1H), 7.86-7.84 (m, 1H), 6.87 (s, 1H), 4.48-4.31 (m, 2H), 3.83 (d, J = 6.7 Hz, 3H), 3.70-3.48 (m, 2H). | [M + H]⁺ 647.0 |
| c-203 | ¹H NMR (600 MHz, CDCl₃) δ 8.04 (s, 1H), 7.89 (s, 1H), 5.87 (tdt, J = 54.7, 23.8, 3.9 Hz, 1H), 4.33-4.14 (m, 2H), 3.85 (d, J = 7.3 Hz, 3H), 3.60-3.37 (m, 2H). | [M + H]⁺ 575.0 |
| c-210 | ¹H NMR (600 MHz, CDCl₃) δ 8.03 (dd, J = 4.9, 1.8 Hz, 1H), 7.87 (d, J = 1.8 Hz, 1H), 6.86 (s, 1H), 4.40-4.20 (m, 2H), 3.63 (d, J = 23.3 Hz, 3H), 3.53-3.31 (m, 2H), 1.25 (td, J = 7.1, 3.0 Hz, 3H). | [M + H]⁺ 550.0 |
| c-217 | ¹H NMR (600 MHz, CDCl₃) δ 8.05 (m, 1H), 7.87 (s, 1H), 7.27 (s, 1H), 4.38- | [M + H]⁺ 597.0 |
| | 4.21 (m, 2H), 4.15-4.00 (m, 2H), 3.69-3.30 (m, 2H), 1.25 (td, J = 7.1, 1.4 Hz, 3H), 1.17 (dt, J = 16.7, 7.1 Hz, 3H). | |
| c-221 | ¹H NMR (600 MHz, CDCl₃) δ 8.04 (dd, J = 4.8, 1.7 Hz, 1H), 7.59 (d, J = 0.3 Hz, 1H), 5.87 (tdt, J = 54.7, 23.8, 3.9 Hz, 1H), 4.33-4.14 (m, 2H), 3.83 (d, J = 7.3 Hz, 3H), 3.60-3.37 (m, 2H). | [M + H]⁺ 606.0 |
| c-224 | ¹H NMR (600 MHz, CDCl₃) δ 7.33 (s, 1H), 6.86 (s, 1H), 5.28 (s, 1H), 3.82 (s, 3H), 3.66 (s, 3H), 3.55-3.23 (m, 2H). | [M + H]⁺ 560.9 |
| c-231 | ¹H NMR (600 MHz, CDCl₃) δ 7.43 (d, J = 1.3 Hz, 1H), 6.92 (d, J = 1.2 Hz, 1H), 6.84 (s, 1H), 4.11-3.99 (m, 2H), 3.81 (s, 3H), 3.48 (d, J = 2.2 Hz, 2H), 1.16 (t, J = 7.1 Hz, 3H). | [M + H]⁺ 618.9 |
| c-238 | ¹H NMR (600 MHz, CDCl₃) δ 6.88 (m, 1H), 6.76 (m, 1H), 6.57 (s, 1H), 4.48-4.31 (m, 2H), 3.83 (d, J = 6.7 Hz, 3H), 3.70-3.48 (m, 2H). | [M + H]⁺ 609.0 |
| c-245 | ¹H NMR (600 MHz, CDCl₃) δ 7.75 (dd, J = 4.8, 1.7 Hz, 1H), 7.28 (d, J = 0.3 Hz, 1H), 5.87 (tdt, J = 54.7, 23.8, 3.9 Hz, 1H), 4.33-4.14 (m, 2H), 3.83 (d, J = 7.3 Hz, 3H), 3.60-3.37 (m, 2H). | [M + H]⁺ 602.0 |
| c-253 | ¹H NMR (600 MHz, CDCl₃) δ 6.88 (m, 1H), 6.74 (m, 1H), 5.27 (s, 1H), 4.38-4.21 (m, 2H), 4.15-4.00 (m, 2H), 3.69-3.30 (m, 2H), 1.25 (td, J = 7.1, 1.4 Hz, 3H), 1.17 (dt, J = 16.7, 7.1 Hz, 3H). | [M + H]⁺ 569.0 |
| c-258 | ¹H NMR (600 MHz, CDCl₃) δ 7.53 (s, 1H), 7.37 (s, 1H), 6.86 (s, 1H), 4.40-4.20 (m, 2H), 4.34 (dd, J = 23.3,7.8 Hz, 2H), 3.63 (s, 3H), 3.55 (s, 3H), 3.53-3.31 (m, 2H), 1.25 (td, J = 7.1, 3.0 Hz, 3H). | [M + H]⁺ 599.0 |
| c-262 | ¹H NMR (600 MHz, CDCl₃) δ 7.77 (m, 1H), 7.36 (m, 1H), 6.87 (s, 1H), 4.48-4.31 (m, 2H), 3.83 (d, J = 6.7 Hz, 3H), 3.70-3.48 (m, 2H). | [M + H]⁺ 640.0 |
| c-266 | ¹H NMR (600 MHz, CDCl₃) δ 8.23 (s, 1H), 7.88 (s, 1H), 7.58 (s, 1H), 3.82 (s, 3H), 3.66 (s, 3H), 3.55-3.23 (m, 2H). | [M + H]⁺ 522.0 |
| c-273 | ¹H NMR (600 MHz, CDCl₃) δ 8.43 (s, 1H), 7.87 (s, 1H), 7.54 (s, 1H), 4.11-3.99 (m, 2H), 3.81 (s, 3H), 3.48 (d, J = 2.2 Hz, 2H), 1.16 (t, J = 7.1 Hz, 3H). | [M + H]⁺ 579.9 |
| c-286 | ¹H NMR (600 MHz, CDCl₃) δ 8.55 (m, 1H), 8.26 (m, 1H), 6.87 (s, 1H), 4.48-4.31 (m, 2H), 3.83 (d, J = 6.7 Hz, 3H), 3.70-3.48 (m, 2H). | [M + H]⁺ 581.0 |
| c-306 | ¹H NMR (600 MHz, CDCl₃) δ 8.49 (s, 1H), 8.27 (s, 1H), 6.86 (s, 1H), 4.40-4.20 (m, 2H), 3.63 (d, J = 23.3 Hz, 3H), 3.53-3.31 (m, 2H), 1.25 (td, J = 7.1, 3.0 Hz, 3H). | [M + H]⁺ 549.0 |
| c-317 | ¹H NMR (600 MHz, CDCl₃) δ 7.59-7.46 (m, 2H), 5.87 (tdt, J = 54.7, 23.8, 3.9 Hz, 1H), 4.33-4.14 (m, 2H), 3.83 (d, J = 7.3 Hz, 3H), 3.60-3.37 (m, 2H). | [M + H]⁺ 604.9 |
| c-327 | ¹H NMR (600 MHz, CDCl₃) δ 8.16 (d, J = 1.3 Hz, 1H), 7.50 (d, J = 1.2 Hz, 1H), 6.84 (s, 1H), 4.11-3.99 (m, 2H), 3.81 (s, 3H), 3.48 (d, J = 2.2 Hz, 2H), 1.16 (t, J = 7.1 Hz, 3H). | [M + H]⁺ 516.0 |
| c-346 | ¹H NMR (600 MHz, CDCl₃) δ 8.58-8.43 (m, 2H), 6.87 (s, 1H), 4.48-4.31 (m, 2H), 3.83 (d, J = 6.7 Hz, 3H), 3.70-3.48 (m, 2H). | [M + H]⁺ 589.9 |

Hydrogen spectrum and mass spectrum data of nuclear magnetic resonance of some compounds shown in the general formula (d) of Table 10 were shown in Table 15.

TABLE 15

Hydrogen Spectrum and Mass Spectrum Data of Nuclear Magnetic Resonance of Some Compounds Shown in General Formula (d)

| Compound | $^1$H-NMR(600 MHz) | MS (ESI) |
|---|---|---|
| d-3 | $^1$H NMR (600 MHz, CDCl$_3$) δ 8.12 (s, 1H), 7.69 (s, 1H), 7.57 (brs, 1H), 3.75 (s, 3H), 3.67(s, 3H), 3.36-3.29(m, 2H). | [M + H]$^+$ 513.1 |
| d-7 | $^1$H NMR (600 MHz, CDCl$_3$) δ 8.01 (s, 1H), 7.75 (s, 1H), 7.58 (brs, 1H), 3.71 (s, 3H), 3.70(s, 3H), 3.35-3.29(m, 2H). | [M + H]$^+$ 497.1 |
| d-8 | $^1$H NMR (600 MHz, CDCl$_3$) δ 7.91 (s, 1H), 7.65 (s, 1H), 7.58 (brs, 1H), 3.74 (s, 3H), 3.60(s, 3H), 3.24-3.06(m, 2H), 2.11(s, 3H). | [M + H]$^+$ 562.0 |
| d-9 | $^1$H NMR (600 MHz, CDCl$_3$) δ 8.61 (brs, 2H), 7.61 (s, 1H), 7.55 (s, 1H), 7.54 (brs, 1H), 4.34 (s, 2H), 3.73 (s, 3H), 3.61(s, 3H), 3.25-3.06 (m, 2H). | [M + H]$^+$ 548.9 |
| d-12 | $^1$H NMR (600 MHz, CDCl$_3$) δ 8.13 (s, 1H), 7.57-7.49 (m, 1H), 7.35 (t, J = 2.2 Hz, 1H), 3.80 (d, J = 18.3 Hz, 3H), 3.61 (d, J = 35.5 Hz, 3H), 3.56-3.37 (m, 2H), 2.92 (II, J = 11.8, 3.4 Hz, 1H), 2.07-1.98 (m, 2H), 1.97-1.86 (m, 2H), 1.77-1.69 (m, 1H), 1.52-1.43 (m, 2H), 1.44-1.34 (m, 3H). | [M + H]$^+$ 559.1 |
| d-13 | $^1$H NMR (600 MHz, CDCl$_3$) δ 8.12 (s, 1H), 7.55 (s, 1H), 7.24 (d, J = 153.3 Hz, 1H), 3.82 (d, J = 16.2 Hz, 3H), 3.62 (d, J = 15.5 Hz, 3H), 3.48-3.36 (m, 1H), 3.45-3.29 (m, 1H), 2.99 (d, J = 13.9 Hz, 3H). | [M + H]$^+$ 491.1 |
| d-14 | $^1$H NMR (600 MHz, CDCl$_3$) δ 8.14 (s, 1H), 7.57 (s, 1H), 7.40 (s, 1H), 3.80 (d, J = 16.4 Hz, 3H), 3.61 (d, J = 31.8 Hz, 3H), 3.51-3.40 (m, 1H), 3.46-3.29 (m, 1H), 3.20-2.98 (m, 2H), 1.38-1.29 (m, 3H). | [M + H]$^+$ 505.0 |
| d-15 | $^1$H NMR (600 MHz, CDCl$_3$) δ 8.71-8.63 (m, 1H), 8.11 (s, 1H), 8.01 (dd, J = 18.1, 7.8 Hz, 1H), 7.95 (qd, J = 7.5, 1.7 Hz, 1H), 7.60 (m, 1H), 7.52-7.48 (m, 1H), 7.43 (dddd, J = 20.7, 7.5, 4.7, 1.1 Hz, 1H), 4.26-4.07 (m, 2H), 4.07-4.01 (m, 1H), 3.69 (t, J = 6.8 Hz, 1H), 3.56-3.29 (m, 2H), 1.59 (dq, J = 14.0, 7.2 Hz, 1H), 1.54-1.44 (m, 2H), 1.31-1.21 (m, 1H), 1.14 (ddd, J = 25.1, 15.4, 8.0 Hz, 2H), 0.93-0.79 (m, 6H). | [M + H]$^+$ 638.0 |
| d-17 | $^1$H NMR (600 MHz, CDCl$_3$) δ 8.07 (s, 1H), 7.78 (s, 2H), 7.52 (dt, J = 6.6, 2.3 Hz, 3H), 6.99 (s, 1H), 4.14 (ddt, J = 45.1, 10.8, 6.8 Hz, 2H), 3.85 (t, J = 6.8 Hz, 2H), 3.36 (s, 2H), 1.60-1.51 (m, 2H), 1.45-1.37 (m, 2H), 1.25-1.18 (m, 4H), 0.86 (td, J = 7.4, 1.9 Hz, 6H). | [M + H]$^+$ 671.0 |
| d-18 | $^1$H NMR (600 MHz, CDCl$_3$) δ 8.07 (s, 1H), 7.66 (s, 2H), 7.55-7.48 (m, 1H), 7.38-7.30 (m, 3H), 4.22-4.10 (m, 2H), 4.09-3.99 (m, 1H), 3.84 (td, J = 6.8, 2.7 Hz, 1H), 3.44 (d, J = 17.2 Hz, 1H), 3.32 (dd, J = 17.3, 8.4 Hz, 1H), 2.41 (d, J = 7.6 Hz, 3H), 1.62-1.49 (m, 3H), 1.41-1.34 (m, 1H), 1.24-1.15 (m, 4H), 0.87-0.82 (m, 6H). | [M + H]$^+$ 651.2 |
| d-20 | $^1$H NMR (600 MHz, CDCl$_3$) δ 8.15 (s, 1H), 7.46 (s, 1H), 7.45 (brs, 1H), 5.45 (brs, 2H), 3.62 (s, 3H), 3.13-3.05(m, 2H). | [M + H]$^+$ 529.9 |
| d-24 | $^1$H NMR (600 MHz, CDCl$_3$) δ 8.15 (s, 1H), 7.47 (s, 1H), 7.45 (brs, 1H), 3.64 (s, 3H), 3.62 (s, 3H), 3.395 (dd, J = 3.4, 1.8 Hz, 1H), 1.12 (d, J = 2.8 Hz, 3H). | [M + H]$^+$ 559.0 |
| d-27 | $^1$H NMR (600 MHz, CDCl$_3$) δ 8.16 (s, 1H), 7.42 (s, 1H), 7.54 (t, J = 2.3 Hz, 1H), 4.78-4.63 (m, 2H), 4.49-4.29 (m, 2H), 3.82 (d, J = 4.8 Hz, 3H), 3.71-3.46 (m, 2H). | [M + H]$^+$ 612.9 |
| d-33 | $^1$H NMR (600 MHz, CDCl$_3$) δ 8.15 (s, 1H), 7.46 (s, 1H), 7.45 (brs, 1H), 3.74 (s, 3H), 3.33-3.25(m, 2H), 2.10 (s, 3H). | [M + H]$^+$ 529.0 |
| d-34 | $^1$H NMR (600 MHz, CDCl$_3$) δ 8.16 (s, 1H), 7.44 (s, 1H), 7.46 (brs, 1H), 3.72 (s, 3H), 3.13-3.05(m, 2H). | [M + H]$^+$ 564.9 |
| d-35 | H NMR (600 MHz, CDCl$_3$) δ 8.18 (s, 1H), 7.43 (s, 1H), 7.45 (brs, 1H), 3.68 (s, 3H), 3.03-2.95(m, 2H). | [M + H]$^+$ 554.9 |
| d-38 | $^1$H NMR (600 MHz, DMSO) δ 9.57 (d, J = 57.9 Hz, 1H), 8.18 (m, 2H), 4.29-4.16 (m, 2H), 3.55-3.46 (m, 2H), 1.15 (dt, J = 15.9, 7.1 Hz, 3H). | [M + H]$^+$ 545.0 |
| d-42 | $^1$H NMR (600 MHz, CDCl$_3$) δ 8.16 (s, 1H), 7.41 (s, 1H), 6.95 (brs, 1H), 5.69-5.59 (m, 1H), 3.85 (d, J = 21.5 Hz, 3H), 3.81-3.62 (m, 2H). | [M + H]$^+$ 694.9 |
| d-46 | $^1$H NMR (600 MHz, CDCl$_3$) δ 8.10 (s, 1H), 7.44 (s, 1H), 7.46 (brs, 1H), 3.13-3.06(m, 2H), 2.43 (s, 3H), 2.10 (s, 3H).. | [M + H]$^+$ 513.0 |
| d-48 | $^1$H NMR (600 MHz, CDCl$_3$) δ 8.09 (s, 1H), 7.43 (s, 1H), 7.40 (brs, 1H), 3.13-3.05(m, 2H), 2.40 (s, 3H). | [M + H]$^+$ 538.9 |
| d-49 | $^1$H NMR (600 MHz, CDCl$_3$) δ 8.07 (s, 1H), 7.46 (s, 1H), 7.39 (brs, 1H), 3.11-3.06(m, 2H), 2.39 (s, 3H). | [M + H]$^+$ 566.9 |
| d-50 | $^1$H NMR (600 MHz, CDCl$_3$) δ 8.05 (s, 1H), 7.46 (s, 1H), 7.45 (brs, 1H), 3.13-3.05(m, 2H). | [M + H]$^+$ 620.9 |
| d-52 | $^1$H NMR (600 MHz, CDCl$_3$) δ 8.05 (s, 1H), 7.51 (s, 1H), 7.44 (brs, 1H), 7.23-7.19(m, 5H), 3.33-3.25(m, 2H). | [M + H]$^+$ 601.8 |
| d-54 | $^1$H NMR (600 MHz, CDCl$_3$) δ 8.08 (s, 1H), 7.50 (s, 1H), 7.45 (brs, 1H), 3.74 (s, 3H), 3.33-3.25(m, 2H). | [M + H]$^+$ 582.8 |
| d-60 | $^1$H NMR (600 MHz, CDCl$_3$) δ 8.05 (s, 1H), 7.55 (s, 1H), 7.41 (brs, 1H), 3.11-3.02(m, 2H). | [M + H]$^+$ 487.9 |
| d-63 | $^1$H NMR (600 MHz, CDCl$_3$) δ 8.07 (s, 1H), 7.56 (s, 1H), 7.42 (brs, 1H), 3.31-3.22(m, 2H). | [M + H]$^+$ 602.8 |
| d-64 | $^1$H NMR (600 MHz, CDCl$_3$) δ 8.06 (s, 1H), 7.58 (s, 1H), 7.43 (brs, 1H), 3.15-3.07(m, 2H). | [M + H]$^+$ 549.9 |
| d-65 | $^1$H NMR (600 MHz, CDCl$_3$) δ 8.03 (s, 1H), 7.50 (s, 1H), 7.41 (brs, 1H), 3.12-3.07(m, 2H). | [M + H]$^+$ 521.9 |
| d-67 | $^1$H NMR (600 MHz, CDCl$_3$) δ 8.05 (s, 1H), 7.56 (s, 1H), 7.44 (brs, 1H), 3.61 (s, 3H), 3.33-3.25(m, 2H). | [M + H]$^+$ 511.9 |
| d-69 | $^1$H NMR (600 MHz, CDCl$_3$) δ 8.03 (s, 1H), 7.47 (s, 1H), 7.20 (brs, 1H), 3.00-2.92(m, 2H). | [M + H]$^+$ 565.1 |
| d-70 | $^1$H NMR (600 MHz, CDCl$_3$) δ 8.07 (s, 1H), 7.47 (s, 1H), 7.21 (brs, 1H), 3.01-2.93(m, 2H). | [M + H]$^+$ 521.9 |
| d-72 | $^1$H NMR (600 MHz, CDCl$_3$) δ 8.13 (s, 1H), 7.57 (s, 1H), 6.88 (s, 0H), 4.24-4.19 (m, 2H), 4.08-3.93 (m, 2H), 3.57-3.45 (m, 1H), 3.48-3.32 (m, 1H), 1.62-1.53 (m, 2H), 1.50 (dddd, J = 13.7, 6.9, 3.5, 2.3 Hz, 2H), 1.31-1.19 (m, 4H), 1.01-0.81 (m, 6H). | [M + H]$^+$ 629.0 |
| d-73 | $^1$H NMR (600 MHz, CDCl$_3$) δ 8.12 (s, 1H), 7.57 (s, 1H), 6.85 (s, 1H), 5.11 (tt, J = 12.5, 6.2 Hz, 1H), 4.93 (dp, J = 30.3, 6.3 Hz, 1H), 3.53-3.37 (m, | [M + H]$^+$ 601.0 |

TABLE 15-continued

Hydrogen Spectrum and Mass Spectrum Data of Nuclear Magnetic Resonance of Some Compounds Shown in General Formula (d)

| Compound | ¹H-NMR(600 MHz) | MS (ESI) |
|---|---|---|
|  | 1H), 3.45-3.22 (m, 1H), 1.27-1.20 (m, 6H), 1.18-1.07 (m, 6H). |  |
| d-74 | ¹H NMR (600 MHz, CDCl₃) δ 8.15 (s, 1H), 7.56 (s, 1H), 7.45 (brs, 1H), 4.75 (s, 1H), 3.65(s, 3H). | [M + H]⁺ 486.9 |
| d-81 | ¹H NMR (600 MHz, CDCl₃) δ 8.15 (s, 1H), 7.58 (s, 1H), 7.47 (brs, 1H), 4.75 (s, 1H). | [M + H]⁺ 510.9 |
| d-82 | ¹H NMR (600 MHz, CDCl₃) δ 8.16 (s, 1H), 7.50 (s, 1H), 7.49 (brs, 1H), 4.76 (s, 1H). | [M + H]⁺ 439.9 |
| d-85 | ¹H NMR (600 MHz, CDCl₃) δ 8.15 (s, 1H), 7.66 (s, 1H), 7.45 (brs, 1H), 3.74 (d, J = 6.9 Hz, 1H), 2.33-2.25(m, 2H). | [M + H]⁺ 497.1 |
| d-90 | ¹H NMR (600 MHz, CDCl₃) δ 8.18 (s, 1H), 7.61 (s, 1H), 7.39 (brs, 1H), 4.71 (s, 1H). | [M + H]⁺ 448.9 |
| d-98 | ¹H NMR (600 MHz, CDCl₃) δ 8.15 (s, 1H), 7.56 (s, 1H), 7.35 (brs, 1H), 4.74 (s, 1H), 3.65(s, 3H), 3.31-3.25(m, 2H). | [M + H]⁺ 530.1 |
| d-103 | ¹H NMR (600 MHz, CDCl₃) δ 8.18 (s, 1H), 7.56 (s, 1H), 7.35 (brs, 1H), 4.74 (s, 1H), 3.33-3.25(m, 2H). | [M + H]⁺ 567.9 |
| d-107 | ¹H NMR (600 MHz, CDCl₃) δ 8.20 (s, 1H), 7.50 (s, 1H), 7.41 (brs, 1H), 4.65 (s, 1H). | [M + H]⁺ 525.9 |
| d-109 | ¹H NMR (600 MHz, CDCl₃) δ 8.17 (s, 1H), 7.56 (s, 1H), 7.45 (brs, 1H), 7.35 (brs, 1H), 4.74 (s, 1H), 2.75(s, 3H). | [M + H]⁺ 514.9 |
| d-112 | ¹H NMR (600 MHz, CDCl₃) δ 8.17 (s, 1H), 7.56 (s, 1H), 7.35 (brs, 1H), 4.74 (s, 1H), 2.45(s, 3H). | [M + H]⁺ 499.9 |
| d-114 | ¹H NMR (600 MHz, CDCl₃) δ 8.20 (s, 1H), 7.56 (s, 1H), 7.35 (brs, 1H), 4.14 (s, 1H). | [M + H]⁺ 535.8 |
| d-119 | ¹H NMR (600 MHz, CDCl₃) δ 8.19 (s, 1H), 7.58 (s, 1H), 7.44 (brs, 1H), 6.23(d, J = 8.3 Hz, 1H), 6.02(dd, J = 1.3, 8.4 Hz, 1H), 4.81 (s, 1H), 1.63(d, J = 9.2 Hz, 3H). | [M + H]⁺ 497.8 |
| d-122 | ¹H NMR (600 MHz, CDCl₃) δ 8.23 (s, 1H), 7.67 (s, 1H), 7.44 (brs, 1H), 4.81 (dd, J = 1.3, 8.4 Hz, 1H), 3.81 (s, 3H), 2.82 (m, 1H), 1.13(d, J = 10.2 Hz, 3H). | [M + H]⁺ 468.9 |
| d-127 | ¹H NMR (600 MHz, CDCl₃) δ 8.15 (s, 1H), 7.54 (s, 1H), 7.43 (brs, 1H), 4.74 (s, 1H). | [M + H]⁺ 478.9 |
| d-129 | ¹H NMR (600 MHz, CDCl₃) δ 8.16 (s, 1H), 7.49 (s, 1H), 7.43 (brs, 1H), 3.74 (s, 1H), 3.13-3.05(m, 2H). | [M + H]⁺ 421.9 |
| d-133 | ¹H NMR (600 MHz, CDCl₃) δ 8.16 (s, 1H), 7.53 (brs, 1H), 7.49 (s, 1H), 7.43 (brs, 1H), 4.14 (s, 1H), 3.34 (s, 3H), 3.13-3.05(m, 2H). | [M + H]⁺ 453.9 |
| d-141 | ¹H NMR (600 MHz, CDCl₃) δ 8.15 (s, 1H), 7.43 (s, 1H), 7.43 (brs, 1H), 3.74 (d, J = 8.4 Hz, 1H), 2.04-1.96 (m, 1H), 0.98 (d, J = 12.9 Hz, 6H). | [M + H]⁺ 424.9 |

Hydrogen spectrum and mass spectrum data of nuclear magnetic resonance of some compounds shown in the general formula (e) of Table 11 were shown in Table 16.

TABLE 16

Hydrogen Spectrum and Mass Spectrum Data of Nuclear Magnetic Resonance of Some Compounds Shown in General Formula (e)

| Compound | ¹H-NMR(600 MHz) | MS (ESI) |
|---|---|---|
| e-1 | ¹H NMR (600 MHz, CDCl₃) δ 8.15 (dd, J = 5.3, 1.8 Hz, 1H), 7.58 (d, J = 1.7 Hz, 1H), 7.15 (brs, 1H), 3.82 (s, 3H), 3.64 (s, 3H), 3.57-3.25 (m, 2H). | [M + H]⁺ 545.1 |
| e-2 | ¹H NMR (600 MHz, CDCl₃) δ 8.13 (d, J = 1.3 Hz, 1H), 7.57 (d, J = 1.2 Hz, 1H), 6.84 (brs, 1H), 4.11-3.99 (m, 2H), 3.81 (s, 3H), 3.48 (d, J = 2.2 Hz, 2H), 1.16 (t, J = 7.1 Hz, 3H). | [M + H]⁺ 559.0 |
| e-3 | ¹H NMR (600 MHz, CDCl₃) δ 8.36 (s, 1H), 7.62 (s, 1H), 7.54 (t, J = 2.3 Hz, 1H), 4.78-4.63 (m, 2H), 4.49-4.29 (m, 2H), 3.82 (d, J = 4.8 Hz, 3H), 3.71-3.46 (m, 2H). | [M + H]⁺ 612.9 |
| e-4 | ¹H NMR (600 MHz, CDCl₃) δ 8.34 (s, 1H), 7.64 (s, 1H), 6.92 (brs, 1H), 5.87 (tdt, J = 54.7, 24.2, 3.9 Hz, 1H), 4.35-4.12 (m, 2H), 3.83 (s, 3H), 3.63-3.35 (m, 2H). | [M + H]⁺ 594.9 |
| e-5 | ¹H NMR (600 MHz, CDCl₃) δ 8.25 (m, 1H), 7.67 (s, 1H), 7.27 (brs, 1H), 4.38-4.21 (m, 2H), 4.15-4.00 (m, 2H), 3.69-3.30 (m, 2H), 1.25 (td, J = 7.1, 1.4 Hz, 3H), 1.17 (dt, J = 16.7, 7.1 Hz, 3H). | [M + H]⁺ 573.2 |
| e-6 | ¹H NMR (600 MHz, CDCl₃) δ 8.23 (dd, J = 4.9, 1.8 Hz, 1H), 7.67 (d, J = 1.8 Hz, 1H), 6.86 (brs, 1H), 4.40-4.20 (m, 2H), 3.63 (s, 3H), 3.53-3.31 (m, 2H), 1.25 (td, J = 7.1, 3.0 Hz, 3H). | [M + H]⁺ 559.0 |
| e-7 | ¹H NMR (600 MHz, CDCl₃) δ 8.17 (dd, J = 5.3, 1.8 Hz, 1H), 7.59 (d, J = 1.7 Hz, 1H), 7.16 (brs, 1H), 3.83 (s, 3H), 3.65 (s, 3H), 3.57-3.25 (m, 2H). | [M + H]⁺ 545.1 |
| e-8 | ¹H NMR (600 MHz, CDCl₃) δ 8.13 (d, J = 1.3 Hz, 1H), 7.55 (d, J = 1.2 Hz, 1H), 6.82 (brs, 1H), 4.11-3.97 (m, 2H), 3.81 (s, 3H), 3.49 (d, J = 2.2 Hz, 2H), 1.16 (t, J = 7.2 Hz, 3H). | [M + H]⁺ 559.0 |
| e-9 | ¹H NMR (600 MHz, CDCl₃) δ 8.35 (s, 1H), 7.63 (s, 1H), 7.44 (t, J = 2.3 Hz, 1H), 4.78-4.62 (m, 2H), 4.50-4.29 (m, 2H), 3.82 (d, J = 4.8 Hz, 3H), 3.71-3.46 (m, 2H). | [M + H]⁺ 612.9 |
| e-10 | ¹H NMR (600 MHz, CDCl₃) δ 8.34 (s, 1H), 7.64 (s, 1H), 6.96 (brs, 1H), 5.87 (tdt, J = 54.7, 24.2, 3.9 Hz, 1H), 4.35-4.12 (m, 2H), 3.93 (s, 3H), 3.64-3.35 (m, 2H). | [M + H]⁺ 594.9 |
| e-11 | ¹H NMR (600 MHz, CDCl₃) δ 8.25 (m, 1H), 7.67 (s, 1H), 7.27 (brs, 1H), 4.39-4.21 (m, 2H), 4.15-4.01 (m, 2H), 3.68-3.30 (m, 2H), 1.25 (td, J = 7.1, 1.5 Hz, 3H), 1.17 (dt, J = 16.7, 7.2 Hz, 3H). | [M + H]⁺ 573.2 |
| e-12 | ¹H NMR (600 MHz, CDCl₃) δ 8.22 (dd, J = 4.9, 1.8 Hz, 1H), 7.68 (d, J = 1.8 Hz, 1H), 6.96 (brs, 1H), 4.40-4.20 (m, 2H), 3.63 (s, 3H), 3.53-3.31 (m, 2H), 1.25 (td, J = 7.1, 3.1 Hz, 3H). | [M + H]⁺ 559.0 |
| e-13 | ¹H NMR (600 MHz, CDCl₃) δ 8.16 (dd, J = 5.3, 1.9 Hz, 1H), 7.58 (d, J = 1.8 Hz, 1H), 7.13 (brs, 1H), 3.82 (s, 3H), 3.64 (s, 3H), 3.59-3.25 (m, 2H). | [M + H]⁺ 545.1 |
| e-14 | ¹H NMR (600 MHz, CDCl₃) δ 8.11 (d, J = 1.4 Hz, 1H), 7.47 (d, J = 1.2 Hz, 1H), 6.84 (brs, 1H), 4.11-3.99 (m, 2H), 3.83 (s, 3H), 3.48 (d, J = 2.2 Hz, 2H), 1.16 (t, J = 7.5 Hz, 3H). | [M + H]⁺ 559.0 |
| e-15 | ¹H NMR (600 MHz, CDCl₃) δ 8.32 (s, 1H), 7.62 (s, 1H), 7.54 (t, J = 2.4 Hz, 1H), 4.78-4.63 (m, 2H), 4.49-4.29 (m, 2H), 3.81 (d, J = 4.8 Hz, 3H), 3.71-3.46 (m, 2H). | [M + H]⁺ 612.9 |

TABLE 16-continued

Hydrogen Spectrum and Mass Spectrum Data of Nuclear Magnetic Resonance of Some Compounds Shown in General Formula (e)

| Compound | $^1$H-NMR(600 MHz) | MS (ESI) |
|---|---|---|
| e-16 | $^1$H NMR (600 MHz, CDCl$_3$) δ 8.33 (s, 1H), 7.64 (s, 1H), 6.92 (brs, 1H), 5.87 (tdt, J = 54.7, 24.2, 3.9 Hz, 1H), 4.34-4.12 (m, 2H), 3.83 (s, 3H), 3.64-3.35 (m, 2H). | [M + H]$^+$ 594.9 |
| e-17 | $^1$H NMR (600 MHz, CDCl$_3$) δ 8.26 (m, 1H), 7.67 (s, 1H), 7.27 (brs, 1H), 4.40-4.21 (m, 2H), 4.15-4.01 (m, 2H), 3.69-3.30 (m, 2H), 1.25 (td, J = 7.3, 1.2Hz, 3H), 1.17 (dt, J = 16.7, 7.3 Hz, 3H). | [M + H]$^+$ 573.2 |
| e-18 | $^1$H NMR (600 MHz, CDCl$_3$) δ 8.33 (dd, J = 4.9, 1.9 Hz, 1H), 7.68 (d, J = 1.6 Hz, 1H), 6.86 (brs, 1H), 4.41-4.21 (m, 2H), 3.62 (s, 3H), 3.52-3.30 (m, 2H), 1.24 (td, J = 7.0, 3.0 Hz, 3H). | [M + H]$^+$ 559.0 |
| e-19 | $^1$H NMR (600 MHz, CDCl$_3$) δ 8.20 (s, 1H), 7.77 (s, 1H), 7.05 (brs, 1H), 3.82 (s, 3H), 3.64 (s, 3H), 3.57-3.25 (m, 2H). | [M + H]$^+$ 545.1 |
| e-20 | $^1$H NMR (600 MHz, CDCl$_3$) δ 8.23 (s, 1H), 7.77 (s, 1H), 6.84 (brs, 1H), 4.11-3.99 (m, 2H), 3.81 (s, 3H), 3.48 (d, J = 2.2 Hz, 2H), 1.16 (t, J = 7.1 Hz, 3H). | [M + H]$^+$ 545.1 |
| e-21 | $^1$H NMR (600 MHz, CDCl$_3$) δ 8.26 (s, 1H), 7.87 (s, 1H), 7.54 (t, J = 2.3 Hz, 1H), 4.78-4.63 (m, 2H), 4.49-4.29 (m, 2H), 3.82 (s, 3H), 3.71-3.46 (m, 2H). | [M + H]$^+$ 559.0 |
| e-22 | $^1$H NMR (600 MHz, CDCl$_3$) δ 8.34 (s, 1H), 7.69 (s, 1H), 6.92 (brs, 1H), 5.87 (tdt, J = 54.7, 24.2, 3.9 Hz, 1H), 4.35-4.12 (m, 2H), 3.83 (s, 3H), 3.63-3.35 (m, 2H). | [M + H]$^+$ 612.9 |
| e-23 | $^1$H NMR (600 MHz, CDCl$_3$) δ 8.25 (s, 1H), 7.57 (s, 1H), 7.27 (brs, 1H), 4.38-4.21 (m, 2H), 4.15-4.00 (m, 2H), 3.69-3.30 (m, 2H), 1.25 (td, J = 7.1, 1.4 Hz, 3H), 1.17 (dt, J = 16.7, 7.1 Hz, 3H). | [M + H]$^+$ 594.9 |
| e-24 | $^1$H NMR (600 MHz, CDCl$_3$) δ 8.23 (s, 1H), 7.88 (s, 1H), 6.86 (s, 1H), 4.40-4.20 (m, 2H), 3.63 (s, 3H), 3.53-3.31 (m, 2H), 1.25 (td, J = 7.1, 3.0 Hz, 3H). | [M + H]$^+$ 573.2 |

Embodiment 9: Insecticidal Activity Embodiment (1) Insecticidal Activity on $2^{nd}$-Instar Larvae of *Plutella xylostella*.

*Plutella xylostella* (L.) is a lepidoptera pest with a chewing mouthpart and is a common vegetable pest. The $2^{nd}$-instar larvae of *Plutella xylostella* were used as test objects and tested by using a leaf immersion feeding method.

Operation process: Samples were weighed accurately, and respectively added with 200 μL of dimethyl sulfoxide to prepare 10 g/L mother liquor which was diluted into a concentration of 500 ppm with an aqueous solution containing 0.05% of Tween-80 during the test. A hole puncher with a diameter of 1.0 cm was used to make cleaned cabbage leaves into leaf discs. The leaf discs were immersed in a liquid medicine, taken out after 5 seconds, air-dried naturally, and transferred into a clean vessel. About 35 $2^{nd}$-instar larvae of *Plutella xylostella* were put into the vessel and fed at a constant temperature of 28° C. Each concentration was repeated 3 times, and an aqueous solution containing 0.05% of Tween-80 was used as a control group. After being treated for 24 hours, a number of dead *Plutella xylostella* was counted, and a mortality (%) was calculated according to a formula that mortality (%)=(number of live larvae in the control group−number of treated live larvae)/number of live larvae in the control group*100%. The results were shown in Table 17 to Table 24.

(2) Insecticidal Activity on $2^{nd}$-Instar Larvae of *Spodoptera exigua*.

*Spodoptera exigua* is a lepidoptera pest with a chewing mouthpart and is a common vegetable pest. The $2^{nd}$-instar larvae of *Spodoptera exigua* were used as test objects and tested by using a leaf immersion feeding method.

Operation process: Samples were weighed accurately, and respectively added with 200 μL, of dimethyl sulfoxide to prepare 10 g/L mother liquor which was diluted into a concentration of 500 ppm with an aqueous solution containing 0.05% of Tween-80 during the test. A hole puncher with a diameter of 1.0 cm was used to make cleaned cabbage leaves into leaf discs. The leaf discs were immersed in a liquid medicine, taken out after 5 seconds, air-dried naturally, and transferred into a clean vessel. About 35 $2^{nd}$-instar larvae of *Spodoptera exigua* were put into the vessel and fed at a constant temperature of 28° C. Each concentration was repeated 3 times, and an aqueous solution containing 0.05% of Tween-80 was used as a control group. After being treated for 24 hours, a number of dead *Spodoptera exigua* was counted, and a mortality (%) was calculated according to a formula that mortality (%)=(number of live larvae in the control group −number of treated live larvae)/number of live larvae in the control group * 100%. The results were shown in Table 17 to Table 24.

(3) Insecticidal Activity on Aphid Adults.

Aphid is a homoptera pest with a piercing-sucking mouthpart and is a common vegetable pest. *Aphis craccivora* were taken as test objects and tested by using an impregnation method.

Operation process: Samples were weighed accurately, and respectively added with 200 μL of dimethyl sulfoxide to prepare 10 g/L mother liquor which was diluted into a concentration of 500 ppm with an aqueous solution containing 0.05% of Tween-80 during the test. After the wingless *Aphis craccivora* adults stably sucked on bean sprouts, the wingless *Aphis craccivora* adults together with the bean sprouts were immersed into a liquid medicine with a concentration of 500 ppm, taken out after 5 seconds, air-dried naturally, transferred into a clean vessel, and fed at a constant temperature of 23° C. Each concentration was repeated 3 times, and an aqueous solution containing 0.05% of Tween-80 was used as a control group. After being treated for 24 hours, a number of dead *Aphis craccivora* was counted, and a mortality (%) was calculated according to a formula that mortality (%)=(number of live *Aphis craccivora* in the control group−number of treated live *Aphis craccivora*)/number of live *Aphis craccivora* in the control group*100%. The results were shown in Table 17 to Table 24.

(4) Insecticidal Activity on *Solenopsis invicta*.

As a hymenoptera pests and a social insect, *Solenopsis invicta* is one of the most destructive invasive organisms. *Solenopsis invicta* were used as test objects and tested by using a water test tube poison-feeding method.

Operation process: Samples were weighed accurately, and respectively added with 200 μL of dimethyl sulfoxide to prepare 10 g/L mother liquor which was diluted into a concentration of 100 ppm with a mixed aqueous solution containing 0.05% of Tween-80 and 5% of honey during the test. *Solenopsis invicta* were placed in a raising test tube, and a liquid medicine was injected into a silica gel plug of the raising test tube by a syringe as long as the liquid medicine did not seep out. The raising test tube was placed in a raising box horizontally, and a small amount of ham sausages were added to the raising test tube as food to raise the *Solenopsis invicta* at a constant temperature of 25° C. After being treated for 24 hours and 72 hours, a number of live *Solenopsis invicta* and a number of dead *Solenopsis invicta* were counted, and a mortality (%) was calculated according to a formula that mortality (%)=(number of live *Solenopsis invicta* in the control group−number of treated live *Solenopsis invicta*)/number of live *Solenopsis invicta* in the control group*100%. The results were shown in Table 17 to Table 24.

TABLE 17

Insecticidal Activity of Compounds of Formula (I) on Test Pests

| Compound No. | *Plutella xylostella* Mortality (%) 500 ppm | *Spodoptera exigua* Mortality (%) 500 ppm | *Aphis craccivora* Mortality (%) 500 ppm | *Solenopsis invicta* Mortality (%) 100 ppm | |
|---|---|---|---|---|---|
| | | | | 24 h | 72 h |
| A1 | 95 | 90 | 100 | 20 | 87 |
| A2 | 97 | 100 | 100 | 19 | 93 |
| A3 | 90 | 100 | 100 | 25 | 100 |
| A4 | 86 | 100 | 100 | 20 | 87 |
| A5 | 100 | 100 | 100 | 34 | 100 |
| A6 | 100 | 100 | 100 | 44 | 100 |
| A7 | 100 | 100 | 100 | 20 | 100 |
| A8 | 100 | 90 | 100 | 26 | 93 |
| A9 | 100 | 100 | 100 | 24 | 100 |
| A10 | 86 | 100 | 100 | 20 | 87 |
| A11 | 100 | 100 | 100 | 34 | 100 |
| A12 | 100 | 100 | 100 | 44 | 100 |
| A13 | 100 | 100 | 100 | 20 | 100 |
| A14 | 100 | 90 | 100 | 26 | 93 |
| A15 | 100 | 100 | 100 | 24 | 100 |
| A16 | 86 | 100 | 100 | 20 | 87 |
| A17 | 100 | 100 | 100 | 34 | 100 |
| A18 | 100 | 100 | 100 | 44 | 100 |
| A19 | 100 | 100 | 100 | 20 | 100 |
| A20 | 100 | 90 | 100 | 26 | 93 |
| A21 | 100 | 100 | 100 | 24 | 100 |
| A22 | 96 | 100 | 100 | 30 | 97 |
| A23 | 100 | 100 | 100 | 34 | 100 |
| A24 | 100 | 100 | 100 | 44 | 100 |
| A25 | 100 | 100 | 100 | 38 | 100 |
| A26 | 100 | 100 | 100 | 45 | 100 |
| A27 | 100 | 100 | 100 | 30 | 100 |
| A28 | 100 | 90 | 100 | 29 | 97 |
| A29 | 100 | 100 | 100 | 26 | 95 |
| A30 | 100 | 100 | 100 | 40 | 100 |
| A31 | 100 | 100 | 100 | 20 | 100 |
| A32 | 100 | 90 | 100 | 26 | 93 |
| A33 | 100 | 100 | 100 | 24 | 100 |
| A34 | 96 | 100 | 100 | 28 | 97 |
| A35 | 100 | 100 | 100 | 31 | 99 |
| A36 | 100 | 100 | 100 | 44 | 100 |
| A37 | 100 | 100 | 100 | 20 | 100 |
| A38 | 100 | 90 | 100 | 26 | 93 |
| A39 | 100 | 100 | 100 | 24 | 100 |
| A40 | 96 | 100 | 100 | 20 | 97 |
| A41 | 100 | 100 | 100 | 24 | 100 |
| A42 | 100 | 100 | 100 | 44 | 100 |
| A43 | 100 | 100 | 100 | 20 | 100 |
| A44 | 100 | 90 | 100 | 26 | 93 |
| A45 | 100 | 100 | 100 | 24 | 100 |
| A46 | 86 | 100 | 100 | 20 | 87 |
| A47 | 100 | 100 | 100 | 34 | 100 |

TABLE 18

Insecticidal Activity of Some Compounds of Formula (I) on Test Pests

| Compound No. | *Plutella xylostella* Mortality (%) 500 ppm | *Spodoptera exigua* Mortality (%) 500 ppm | *Aphis craccivora* Mortality (%) 500 ppm | *Solenopsis invicta* Mortality (%) 100 ppm | |
|---|---|---|---|---|---|
| | | | | 24 h | 72 h |
| B1 | 100 | 100 | 100 | 20 | 100 |
| B2 | 100 | 90 | 93 | 26 | 93 |
| B3 | 100 | 100 | 100 | 24 | 100 |
| B4 | 86 | 100 | 100 | 20 | 88 |
| B5 | 100 | 100 | 100 | 34 | 100 |
| B6 | 90 | 100 | 100 | 44 | 100 |
| B7 | 100 | 100 | 100 | 38 | 100 |
| B8 | 100 | 100 | 100 | 45 | 100 |
| B9 | 100 | 100 | 100 | 38 | 100 |
| B10 | 100 | 95 | 100 | 30 | 90 |
| B11 | 100 | 100 | 100 | 33 | 95 |
| B12 | 100 | 100 | 100 | 40 | 100 |

TABLE 19

Insecticidal Activity of Compounds of Formula (I) in Table 3 on Test Pests

| Compound No. | *Plutella xylostella* Mortality (%) 500 ppm | *Spodoptera exigua* Mortality (%) 500 ppm | *Aphis craccivora* Mortality (%) 500 ppm | *Solenopsis invicta* Mortality (%) 100 ppm | |
|---|---|---|---|---|---|
| | | | | 24 h | 72 h |
| C1 | 89 | 100 | 100 | 20 | 100 |
| C2 | 100 | 90 | 100 | 26 | 93 |
| C3 | 100 | 100 | 100 | 24 | 100 |
| C4 | 86 | 76 | 100 | 20 | 87 |
| C5 | 100 | 100 | 100 | 34 | 100 |
| C6 | 100 | 100 | 100 | 44 | 100 |
| C7 | 100 | 100 | 100 | 38 | 100 |
| C8 | 91 | 85 | 95 | 36 | 92 |
| C9 | 100 | 100 | 100 | 39 | 100 |
| C10 | 100 | 85 | 100 | 27 | 100 |
| C11 | 100 | 100 | 100 | 46 | 100 |
| C12 | 100 | 91 | 100 | 18 | 95 |
| C13 | 100 | 100 | 100 | 32 | 100 |
| C14 | 100 | 100 | 100 | 30 | 100 |
| C15 | 89 | 100 | 100 | 29 | 90 |
| C16 | 100 | 95 | 99 | 23 | 89 |
| C17 | 88 | 89 | 100 | 15 | 68 |
| C18 | 90 | 86 | 98 | 20 | 70 |
| C19 | 90 | 90 | 100 | 18 | 70 |
| C20 | 100 | 100 | 100 | 28 | 99 |
| C21 | 90 | 95 | 100 | 19 | 99 |
| C22 | 99 | 94 | 89 | 20 | 70 |
| C23 | 86 | 88 | 95 | 18 | 80 |
| C24 | 100 | 100 | 100 | 36 | 100 |
| C25 | 92 | 97 | 86 | 25 | 71 |
| C26 | 89 | 90 | 100 | 20 | 80 |
| C27 | 76 | 86 | 100 | 27 | 86 |
| C28 | 100 | 100 | 100 | 30 | 98 |
| C29 | 100 | 93 | 100 | 30 | 100 |
| C30 | 100 | 90 | 92 | 24 | 100 |
| C31 | 100 | 100 | 100 | 34 | 100 |
| C32 | 100 | 90 | 95 | 25 | 100 |
| C33 | 100 | 100 | 100 | 36 | 100 |
| C34 | 100 | 100 | 100 | 40 | 100 |
| C35 | 100 | 100 | 100 | 38 | 100 |
| C36 | 90 | 90 | 100 | 10 | 90 |
| C37 | 100 | 100 | 100 | 20 | 100 |

TABLE 19-continued

Insecticidal Activity of Compounds of Formula (I) in Table 3 on Test Pests

| Compound No. | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | Solenopsis invicta Mortality (%) 100 ppm 72 h |
|---|---|---|---|---|---|
| C38 | 100 | 90 | 100 | 25 | 90 |
| C39 | 90 | 100 | 98 | 24 | 87 |
| C40 | 100 | 95 | 100 | 28 | 90 |
| C41 | 89 | 94 | 100 | 19 | 90 |
| C42 | 91 | 94 | 100 | 20 | 70 |
| C43 | 86 | 89 | 95 | 18 | 80 |
| C44 | 90 | 100 | 100 | 36 | 90 |
| C45 | 93 | 97 | 86 | 25 | 71 |
| C46 | 89 | 91 | 90 | 21 | 80 |
| C47 | 77 | 86 | 80 | 27 | 87 |
| C48 | 76 | 85 | 79 | 26 | 86 |
| C49 | 87 | 89 | 90 | 20 | 81 |
| C50 | 81 | 86 | 90 | 26 | 86 |
| C51 | 87 | 85 | 79 | 19 | 86 |
| C52 | 90 | 91 | 100 | 22 | 90 |
| C53 | 78 | 89 | 90 | 28 | 97 |
| C54 | 77 | 78 | 87 | 17 | 84 |
| C55 | 88 | 80 | 91 | 19 | 83 |
| C56 | 82 | 87 | 91 | 27 | 80 |
| C57 | 78 | 76 | 80 | 20 | 89 |
| C58 | 100 | 100 | 100 | 29 | 98 |
| C59 | 100 | 90 | 100 | 29 | 100 |
| C60 | 90 | 92 | 100 | 25 | 92 |
| C61 | 88 | 100 | 90 | 28 | 100 |
| C62 | 80 | 85 | 97 | 27 | 100 |
| C63 | 98 | 90 | 96 | 29 | 98 |
| C64 | 92 | 97 | 100 | 17 | 90 |

TABLE 20

Insecticidal Activity of Some Compounds of General Formula (a) on Test Pests

| Compound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | Solenopsis invicta Mortality (%) 100 ppm 72 h |
|---|---|---|---|---|---|
| a-1 | 100 | 100 | 100 | 20 | 100 |
| a-2 | 97 | 97 | 100 | 19 | 98 |
| a-3 | 90 | 90 | 100 | 25 | 100 |
| a-4 | 86 | 95 | 100 | 20 | 97 |
| a-5 | 90 | 89 | 100 | 24 | 96 |
| a-6 | 100 | 100 | 100 | 34 | 100 |
| a-7 | 95 | 91 | 100 | 20 | 90 |
| a-8 | 95 | 90 | 95 | 10 | 90 |
| a-9 | 100 | 100 | 100 | 14 | 100 |
| a-10 | 100 | 100 | 100 | 20 | 97 |
| a-11 | 100 | 100 | 100 | 24 | 100 |
| a-12 | 100 | 100 | 100 | 19 | 100 |
| a-13 | 100 | 100 | 100 | 20 | 100 |
| a-14 | 100 | 100 | 100 | 26 | 100 |
| a-15 | 100 | 100 | 100 | 21 | 100 |
| a-16 | 96 | 86 | 100 | 20 | 87 |
| a-17 | 96 | 89 | 100 | 24 | 90 |
| a-18 | 96 | 86 | 100 | 20 | 87 |
| a-19 | 95 | 91 | 100 | 20 | 90 |
| a-20 | 100 | 90 | 100 | 26 | 93 |
| a-21 | 91 | 79 | 100 | 24 | 90 |
| a-22 | 100 | 100 | 100 | 30 | 100 |
| a-26 | 100 | 100 | 100 | 34 | 100 |
| a-27 | 100 | 100 | 100 | 25 | 100 |
| a-28 | 100 | 95 | 100 | 23 | 99 |
| a-29 | 100 | 91 | 100 | 14 | 96 |
| a-30 | 96 | 90 | 100 | 20 | 97 |
| a-36 | 100 | 96 | 100 | 14 | 91 |
| a-37 | 100 | 96 | 100 | 15 | 99 |
| a-38 | 90 | 90 | 100 | 26 | 100 |
| a-39 | 90 | 89 | 100 | 25 | 93 |
| a-40 | 90 | 89 | 100 | 19 | 90 |
| a-41 | 86 | 81 | 99 | 20 | 94 |
| a-42 | 96 | 96 | 100 | 21 | 96 |
| a-43 | 86 | 81 | 99 | 20 | 94 |
| a-44 | 100 | 95 | 100 | 15 | 95 |
| a-45 | 100 | 91 | 100 | 20 | 90 |
| a-47 | 100 | 90 | 100 | 19 | 97 |
| a-51 | 91 | 89 | 100 | 16 | 95 |
| a-52 | 100 | 89 | 91 | 20 | 89 |
| a-53 | 100 | 96 | 100 | 20 | 100 |
| a-56 | 100 | 90 | 100 | 16 | 93 |
| a-57 | 100 | 100 | 100 | 24 | 100 |
| a-59 | 96 | 91 | 100 | 28 | 97 |
| a-62 | 100 | 100 | 100 | 21 | 99 |
| a-63 | 100 | 100 | 100 | 24 | 100 |
| a-64 | 100 | 99 | 100 | 20 | 99 |
| a-65 | 100 | 100 | 100 | 26 | 100 |
| a-71 | 100 | 99 | 100 | 24 | 100 |
| a-72 | 96 | 89 | 100 | 20 | 91 |
| a-76 | 95 | 85 | 91 | 24 | 80 |
| a-77 | 90 | 86 | 96 | 44 | 90 |
| a-80 | 91 | 85 | 100 | 10 | 100 |
| a-83 | 100 | 90 | 100 | 26 | 93 |
| a-86 | 100 | 89 | 100 | 24 | 89 |
| a-87 | 96 | 100 | 100 | 20 | 97 |
| a-88 | 100 | 100 | 100 | 34 | 100 |
| a-95 | 96 | 89 | 100 | 21 | 92 |
| a-100 | 91 | 90 | 100 | 20 | 90 |
| a-109 | 95 | 89 | 100 | 20 | 90 |
| a-111 | 100 | 100 | 100 | 19 | 97 |
| a-112 | 100 | 96 | 100 | 16 | 99 |
| a-118 | 96 | 95 | 100 | 25 | 100 |
| a-122 | 91 | 89 | 100 | 20 | 90 |
| a-132 | 90 | 90 | 100 | 26 | 94 |
| a-133 | 100 | 100 | 100 | 24 | 100 |
| a-134 | 100 | 100 | 100 | 27 | 100 |
| a-136 | 100 | 100 | 100 | 11 | 100 |

TABLE 21

Insecticidal Activity of Some Compounds of General Formula (b) on Test Pests

| Compound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | Solenopsis invicta Mortality (%) 100 ppm 72 h |
|---|---|---|---|---|---|
| b-1 | 100 | 100 | 100 | 20 | 97 |
| b-2 | 100 | 95 | 100 | 19 | 93 |
| b-3 | 90 | 90 | 95 | 25 | 90 |
| b-4 | 90 | 89 | 96 | 20 | 90 |
| b-5 | 89 | 80 | 100 | 14 | 100 |
| b-6 | 100 | 100 | 100 | 20 | 100 |
| b-7 | 100 | 90 | 100 | 17 | 97 |
| b-8 | 100 | 96 | 100 | 26 | 92 |
| b-9 | 100 | 100 | 100 | 19 | 100 |
| b-10 | 100 | 100 | 100 | 20 | 100 |
| b-11 | 100 | 100 | 100 | 34 | 100 |
| b-12 | 100 | 100 | 100 | 14 | 100 |
| b-13 | 100 | 100 | 100 | 20 | 100 |
| b-14 | 100 | 100 | 100 | 26 | 100 |
| b-15 | 100 | 100 | 100 | 24 | 100 |
| b-16 | 96 | 90 | 100 | 20 | 97 |
| b-17 | 100 | 92 | 100 | 14 | 100 |
| b-18 | 99 | 89 | 98 | 14 | 100 |
| b-19 | 100 | 95 | 100 | 20 | 100 |
| b-20 | 100 | 90 | 100 | 21 | 93 |
| b-21 | 90 | 81 | 90 | 24 | 86 |
| b-23 | 96 | 95 | 100 | 10 | 97 |
| b-25 | 100 | 100 | 100 | 26 | 100 |
| b-27 | 91 | 89 | 100 | 19 | 100 |
| b-28 | 100 | 99 | 100 | 16 | 100 |
| b-30 | 90 | 85 | 100 | 25 | 94 |
| b-34 | 90 | 87 | 100 | 10 | 100 |
| b-37 | 86 | 90 | 99 | 20 | 94 |
| b-38 | 90 | 85 | 99 | 32 | 90 |
| b-39 | 96 | 85 | 97 | 24 | 90 |
| b-43 | 89 | 80 | 89 | 19 | 90 |
| b-47 | 95 | 85 | 100 | 18 | 90 |
| b-48 | 100 | 89 | 100 | 15 | 90 |
| b-50 | 99 | 90 | 100 | 10 | 100 |
| b-54 | 100 | 90 | 100 | 25 | 97 |
| b-56 | 100 | 100 | 100 | 26 | 100 |
| b-57 | 100 | 100 | 100 | 30 | 100 |
| b-59 | 100 | 100 | 100 | 20 | 100 |
| b-62 | 100 | 96 | 100 | 26 | 93 |
| b-63 | 100 | 100 | 100 | 24 | 100 |
| b-66 | 96 | 91 | 100 | 28 | 97 |
| b-68 | 99 | 100 | 100 | 21 | 99 |
| b-70 | 100 | 95 | 100 | 44 | 100 |
| b-73 | 89 | 85 | 100 | 20 | 90 |
| b-76 | 95 | 90 | 100 | 26 | 93 |
| b-80 | 95 | 90 | 100 | 14 | 90 |
| b-86 | 96 | 89 | 100 | 20 | 97 |
| b-87 | 95 | 95 | 100 | 14 | 100 |
| b-88 | 100 | 100 | 100 | 25 | 100 |
| b-94 | 100 | 90 | 100 | 20 | 100 |
| b-96 | 100 | 93 | 100 | 26 | 98 |
| b-99 | 91 | 85 | 100 | 24 | 90 |
| b-104 | 96 | 96 | 100 | 20 | 96 |
| b-111 | 100 | 100 | 100 | 24 | 100 |
| b-116 | 100 | 98 | 100 | 20 | 100 |
| b-118 | 99 | 91 | 100 | 14 | 99 |
| b-123 | 99 | 95 | 100 | 24 | 100 |
| b-131 | 95 | 95 | 100 | 11 | 100 |
| b-134 | 100 | 100 | 100 | 26 | 100 |
| b-135 | 100 | 100 | 100 | 23 | 100 |
| b-136 | 100 | 100 | 100 | 20 | 97 |
| b-138 | 100 | 100 | 100 | 14 | 100 |

TABLE 22

Insecticidal Activity of Some Compounds of General Formula (c) on Test Pests

| Compound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | Solenopsis invicta Mortality (%) 100 ppm 72 h |
|---|---|---|---|---|---|
| c-2 | 95 | 90 | 100 | 20 | 97 |
| c-4 | 97 | 100 | 100 | 29 | 93 |
| c-7 | 100 | 100 | 100 | 20 | 100 |
| c-8 | 100 | 100 | 100 | 20 | 100 |
| c-9 | 99 | 100 | 100 | 14 | 100 |
| c-10 | 99 | 95 | 100 | 24 | 100 |
| c-13 | 100 | 95 | 100 | 21 | 100 |
| c-14 | 100 | 96 | 100 | 26 | 100 |
| c-15 | 95 | 90 | 100 | 24 | 100 |
| c-19 | 100 | 100 | 100 | 20 | 100 |
| c-20 | 100 | 100 | 100 | 14 | 100 |
| c-34 | 100 | 100 | 100 | 34 | 100 |
| c-36 | 92 | 90 | 95 | 21 | 100 |
| c-37 | 96 | 90 | 100 | 21 | 93 |
| c-39 | 95 | 89 | 100 | 24 | 90 |
| c-42 | 86 | 80 | 100 | 20 | 97 |
| c-47 | 90 | 89 | 100 | 35 | 99 |
| c-49 | 100 | 95 | 100 | 44 | 100 |
| c-53 | 100 | 96 | 100 | 20 | 100 |
| c-54 | 100 | 90 | 100 | 26 | 96 |
| c-57 | 95 | 89 | 100 | 24 | 95 |
| c-61 | 96 | 100 | 100 | 26 | 97 |
| c-64 | 96 | 90 | 100 | 14 | 100 |
| c-67 | 100 | 100 | 100 | 25 | 100 |
| c-72 | 100 | 90 | 100 | 23 | 99 |
| c-73 | 100 | 100 | 100 | 14 | 90 |
| c-77 | 96 | 90 | 100 | 20 | 97 |
| c-80 | 100 | 100 | 100 | 13 | 90 |
| c-84 | 99 | 96 | 100 | 25 | 95 |
| c-86 | 100 | 99 | 100 | 16 | 100 |
| c-91 | 90 | 82 | 100 | 25 | 94 |
| c-93 | 90 | 89 | 100 | 30 | 100 |
| c-96 | 86 | 90 | 99 | 20 | 84 |
| c-97 | 100 | 100 | 100 | 32 | 100 |
| c-98 | 96 | 90 | 100 | 24 | 90 |
| c-101 | 89 | 80 | 100 | 19 | 99 |
| c-105 | 96 | 100 | 100 | 25 | 100 |
| c-106 | 99 | 95 | 100 | 27 | 100 |
| c-107 | 99 | 90 | 100 | 26 | 99 |
| c-110 | 100 | 100 | 100 | 14 | 100 |
| c-111 | 98 | 99 | 100 | 17 | 99 |
| c-113 | 98 | 91 | 99 | 14 | 98 |
| c-114 | 96 | 89 | 100 | 18 | 100 |
| c-117 | 100 | 100 | 100 | 25 | 100 |
| c-118 | 95 | 85 | 100 | 20 | 90 |
| c-121 | 100 | 90 | 100 | 19 | 97 |
| c-123 | 100 | 96 | 100 | 26 | 99 |
| c-126 | 100 | 100 | 100 | 35 | 100 |
| c-128 | 91 | 89 | 100 | 20 | 90 |
| c-131 | 90 | 84 | 92 | 26 | 94 |
| c-135 | 90 | 79 | 96 | 24 | 89 |
| c-139 | 96 | 91 | 100 | 28 | 87 |
| c-145 | 100 | 95 | 100 | 11 | 99 |
| c-149 | 100 | 100 | 100 | 31 | 100 |
| c-150 | 95 | 87 | 91 | 20 | 90 |
| c-152 | 100 | 89 | 100 | 16 | 93 |
| c-154 | 89 | 71 | 91 | 24 | 80 |
| c-159 | 96 | 100 | 100 | 20 | 97 |
| c-164 | 100 | 80 | 100 | 24 | 90 |
| c-166 | 100 | 100 | 100 | 25 | 100 |
| c-169 | 100 | 100 | 100 | 20 | 99 |
| c-173 | 95 | 90 | 100 | 25 | 93 |
| c-180 | 95 | 82 | 100 | 21 | 91 |
| c-186 | 89 | 81 | 99 | 20 | 87 |
| c-188 | 100 | 100 | 100 | 14 | 100 |
| c-196 | 100 | 90 | 100 | 20 | 97 |
| c-203 | 97 | 100 | 100 | 29 | 100 |

TABLE 22-continued

Insecticidal Activity of Some Compounds of General Formula (c) on Test Pests

| Com-pound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | 72 h |
|---|---|---|---|---|---|
| c-210 | 100 | 100 | 100 | 20 | 100 |
| c-217 | 100 | 100 | 100 | 20 | 100 |
| c-221 | 99 | 100 | 100 | 14 | 100 |
| c-224 | 99 | 95 | 100 | 25 | 100 |
| c-231 | 100 | 100 | 100 | 21 | 100 |
| c-238 | 100 | 96 | 100 | 26 | 100 |
| c-245 | 95 | 94 | 100 | 14 | 100 |
| c-253 | 96 | 100 | 100 | 20 | 97 |
| c-258 | 100 | 100 | 100 | 14 | 100 |
| c-262 | 100 | 100 | 100 | 34 | 100 |
| c-266 | 92 | 90 | 95 | 21 | 100 |
| c-273 | 96 | 90 | 100 | 21 | 93 |
| c-286 | 95 | 89 | 100 | 24 | 90 |
| c-306 | 96 | 80 | 100 | 20 | 97 |
| c-317 | 90 | 89 | 100 | 20 | 100 |
| c-327 | 100 | 95 | 100 | 34 | 100 |
| c-346 | 100 | 96 | 100 | 20 | 100 |

TABLE 23

Insecticidal Activity of Some Compounds of General Formula (d) on Test Pests

| Com-pound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | 72 h |
|---|---|---|---|---|---|
| d-3 | 100 | 98 | 100 | 21 | 87 |
| d-7 | 100 | 100 | 100 | 20 | 99 |
| d-8 | 85 | 82 | 90 | 15 | 65 |
| d-9 | 82 | 79 | 96 | 21 | 77 |
| d-10 | 55 | 50 | 90 | 34 | 80 |
| d-11 | 76 | 70 | 99 | 14 | 76 |
| d-12 | 86 | 96 | 100 | 20 | 100 |
| d-13 | 82 | 81 | 99 | 26 | 89 |
| d-14 | 90 | 89 | 100 | 24 | 100 |
| d-15 | 96 | 100 | 100 | 19 | 97 |
| d-16 | 85 | 93 | 96 | 34 | 100 |
| d-17 | 99 | 95 | 100 | 42 | 100 |
| d-18 | 81 | 80 | 100 | 15 | 85 |
| d-19 | 100 | 90 | 100 | 23 | 99 |
| d-20 | 100 | 100 | 100 | 14 | 100 |
| d-26 | 100 | 100 | 100 | 20 | 100 |
| d-27 | 100 | 100 | 100 | 14 | 100 |
| d-28 | 100 | 96 | 100 | 25 | 100 |
| d-33 | 100 | 99 | 100 | 26 | 100 |
| d-34 | 90 | 95 | 100 | 25 | 93 |
| d-35 | 90 | 89 | 100 | 30 | 100 |
| d-38 | 86 | 9 | 99 | 30 | 84 |
| d-42 | 100 | 100 | 100 | 31 | 100 |
| d-46 | 95 | 90 | 100 | 14 | 90 |
| d-47 | 100 | 100 | 100 | 29 | 99 |
| d-48 | 96 | 90 | 100 | 26 | 100 |
| d-49 | 100 | 100 | 100 | 29 | 100 |
| d-50 | 100 | 90 | 100 | 26 | 93 |
| d-52 | 100 | 100 | 100 | 24 | 100 |
| d-54 | 100 | 99 | 100 | 21 | 99 |
| d-56 | 90 | 89 | 99 | 14 | 80 |

TABLE 23-continued

Insecticidal Activity of Some Compounds of General Formula (d) on Test Pests

| Com-pound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | 72 h |
|---|---|---|---|---|---|
| d-57 | 89 | 80 | 90 | 20 | 70 |
| d-58 | 76 | 70 | 96 | 21 | 99 |
| d-60 | 96 | 90 | 90 | 24 | 90 |
| d-63 | 100 | 95 | 100 | 20 | 90 |
| d-64 | 100 | 90 | 100 | 26 | 93 |
| d-65 | 100 | 100 | 100 | 24 | 90 |
| d-67 | 100 | 90 | 100 | 41 | 99 |
| d-69 | 90 | 86 | 100 | 44 | 100 |
| d-70 | 91 | 90 | 99 | 20 | 98 |
| d-72 | 90 | 85 | 99 | 26 | 76 |
| d-73 | 81 | 66 | 96 | 24 | 85 |
| d-74 | 100 | 100 | 100 | 21 | 99 |
| d-77 | 100 | 99 | 100 | 44 | 100 |
| d-81 | 99 | 90 | 100 | 35 | 100 |
| d-82 | 95 | 89 | 100 | 25 | 90 |
| d-85 | 100 | 100 | 100 | 30 | 100 |
| d-86 | 100 | 90 | 100 | 29 | 97 |
| d-90 | 82 | 80 | 90 | 16 | 85 |
| d-94 | 89 | 90 | 99 | 20 | 90 |
| d-98 | 100 | 100 | 100 | 20 | 99 |
| d-103 | 100 | 98 | 100 | 26 | 93 |
| d-107 | 100 | 100 | 100 | 24 | 100 |
| d-109 | 96 | 85 | 99 | 28 | 85 |
| d-112 | 96 | 80 | 100 | 36 | 99 |
| d-114 | 100 | 87 | 100 | 24 | 90 |
| d-115 | 99 | 90 | 100 | 20 | 100 |
| d-119 | 89 | 90 | 92 | 26 | 83 |
| d-122 | 91 | 84 | 90 | 24 | 95 |
| d-127 | 96 | 100 | 100 | 20 | 97 |
| d-129 | 95 | 100 | 100 | 24 | 100 |
| d-133 | 70 | 86 | 100 | 21 | 95 |
| d-141 | 90 | 95 | 100 | 11 | 91 |

TABLE 24

Insecticidal Activity of Some Compounds of General Formula (e) on Test Pests

| Com-pound | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm 24 h | 72 h |
|---|---|---|---|---|---|
| e-1 | 100 | 100 | 100 | 33 | 100 |
| e-2 | 100 | 100 | 100 | 25 | 100 |
| e-3 | 100 | 95 | 100 | 20 | 98 |
| e-4 | 100 | 100 | 100 | 32 | 100 |
| e-5 | 100 | 100 | 100 | 34 | 100 |
| e-6 | 100 | 100 | 100 | 34 | 100 |
| e-7 | 100 | 100 | 100 | 29 | 99 |
| e-8 | 100 | 100 | 100 | 35 | 100 |
| e-9 | 96 | 90 | 100 | 40 | 96 |
| e-10 | 100 | 100 | 100 | 37 | 100 |
| e-11 | 100 | 100 | 100 | 33 | 100 |
| e-12 | 100 | 100 | 100 | 34 | 100 |
| e-13 | 100 | 100 | 100 | 20 | 100 |
| e-14 | 100 | 100 | 100 | 34 | 100 |
| e-15 | 90 | 89 | 100 | 32 | 100 |
| e-16 | 100 | 100 | 100 | 32 | 99 |

TABLE 24-continued

Insecticidal Activity of Some Compounds
of General Formula (e) on Test Pests

| Com-pound | Insecticidal activity | | | | |
|---|---|---|---|---|---|
| | Plutella xylostella Mortality (%) 500 ppm | Spodoptera exigua Mortality (%) 500 ppm | Aphis craccivora Mortality (%) 500 ppm | Solenopsis invicta Mortality (%) 100 ppm | |
| | | | | 24 h | 72 h |
| e-17 | 100 | 100 | 100 | 30 | 100 |
| e-18 | 100 | 100 | 100 | 29 | 100 |
| e-19 | 100 | 100 | 100 | 31 | 90 |
| e-20 | 100 | 100 | 100 | 31 | 100 |
| e-21 | 100 | 100 | 100 | 30 | 100 |
| e-22 | 100 | 100 | 100 | 35 | 100 |
| e-23 | 100 | 100 | 100 | 34 | 93 |
| e-24 | 100 | 100 | 100 | 34 | 100 |

It can be seen from the tables that the compounds illustrated in the present invention have a high killing activity on agroforestry pests, animal parasitic pests, sanitary insect pest and the like, have an good activity on lepidoptera, homoptera, hymenoptera pests and the like, have a delayed working effect on *Solenopsis invicta*, and have a better killing effect on a whole *Solenopsis invicta* nest and a queen *Solenopsis invicta*.

Embodiment 10: Environmental Safety Embodiment

Results of toxicity tests of some compounds of the present invention on environmental non-target organisms were shown in the table below:

(1) Toxicity Test on $2^{nd}$-Instar Larvae of *Bombyx mori* L.

*Bombyx mori* L. is an important economic insect sensitive to pesticides in an agricultural ecosystem, and is also one of the non-target organisms of environmental ecology listed in pesticide registration of China. The $2^{nd}$-instar larvae of *Bombyx mori* L. were used as test objects and tested by using a leaf immersion feeding method.

Operation process: Samples were weighed accurately, and respectively added with 200 μL of dimethyl sulfoxide to prepare 10 g/L mother liquor which was diluted into a concentration of 1000 ppm with an aqueous solution containing 0.05% of Tween-80 during the test. Young cotyledons of mulberries were collected, washed and air-dried, immersed in a liquid medicine, taken out after 5 seconds, naturally air-dryed, and then transferred into a clean vessel. About 35 $2^{nd}$-instar larvae of *Bombyx mori* L. were put into the vessel and fed at a constant temperature of 25° C. Each concentration was repeated 3 times, and an aqueous solution containing 0.05% of Tween-80 was used as a control group. After being treated for 24 hours, a number of dead *Bombyx mori* L. was counted, and a mortality (%) was calculated according to a formula that mortality (%)=(number of live larvae in the control group −number of treated live larvae)/ number of live larvae in the control group * 100%. The results were shown in Table 10.

(2) Toxicity Test on Adult Worker Bees of *Apis cernan*.

Adult worker bees of *Apis cernan* having the same size were selected for test. The worker bees were collected from beekeeping boxes in the daystart of the test day and tested by using a small beaker method.

Operation process: A small amount of absorbent cotton was put into a 5 mL small beaker, 5 mL of a test liquid medicine (a concentration of 500 ppm) was dropped into the absorbent cotton, and stirred gently to make the absorbent cotton completely wet but not leached obviously, then the small beaker was put into a 500 mL large beaker, then 15 worker bees were put into the large beaker, and finally the large beaker was sealed with gauze. After treatment, the large beaker was placed in a dark room of an artificial climate box. After taking the medicine for 48 hours, a number of live and dead worker bees were investigated. The results were shown in Table 25.

TABLE 25

Toxicity of Some Compounds of Formula (I) Shown in Table 1 to Table 3 on Environmental Non-target Organisms

| Compound No. | Toxicity Bombyx mori L. Mortality (%) 1000 ppm | determination Apis cernan Mortality (%) 500 ppm | Compound No. | Toxicity Bombyx mori L. Mortality (%) 1000 ppm | determination Apis cernan Mortality (%) 500 ppm |
|---|---|---|---|---|---|
| A1 | 9 | 12 | A22 | 0 | 3 |
| A4 | 10 | 8 | A23 | 0 | 5 |
| A5 | 2 | 9 | A26 | 7 | 10 |
| A7 | 6 | 6 | A27 | 10 | 15 |
| A8 | 12 | 10 | A30 | 8 | 8 |
| A10 | 15 | 12 | A32 | 10 | 4 |
| A12 | 13 | 12 | A36 | 3 | 0 |
| A13 | 17 | 17 | A43 | 3 | 8 |
| A15 | 8 | 5 | A44 | 8 | 8 |
| A19 | 7 | 5 | A45 | 10 | 11 |
| A21 | 0 | 6 | A46 | 7 | 2 |
| B1 | 0 | 0 | B7 | 6 | 6 |
| B2 | 3 | 4 | B8 | 5 | 4 |
| B3 | 0 | 3 | B9 | 0 | 5 |
| B4 | 0 | 0 | B10 | 3 | 3 |
| B5 | 6 | 4 | B11 | 7 | 3 |
| B6 | 4 | 5 | B12 | 5 | 6 |
| C1 | 7 | 7 | C32 | 6 | 9 |
| C2 | 5 | 10 | C35 | 4 | 4 |
| C3 | 12 | 10 | C36 | 2 | 3 |
| C4 | 3 | 0 | C37 | 6 | 8 |
| C9 | 8 | 9 | C38 | 4 | 0 |

TABLE 25-continued

Toxicity of Some Compounds of Formula (I) Shown in Table 1 to Table 3 on Environmental Non-target Organisms

| Compound No. | Toxicity Bombyx mori L. Mortality (%) 1000 ppm | determination Apis cernan Mortality (%) 500 ppm | Compound No. | Toxicity Bombyx mori L. Mortality (%) 1000 ppm | determination Apis cernan Mortality (%) 500 ppm |
|---|---|---|---|---|---|
| C10 | 10 | 9 | C40 | 4 | 4 |
| C13 | 12 | 10 | C43 | 0 | 4 |
| C14 | 10 | 10 | C45 | 6 | 3 |
| C15 | 8 | 7 | C46 | 5 | 3 |
| C18 | 6 | 5 | C50 | 5 | 2 |
| C20 | 8 | 10 | C51 | 9 | 5 |
| C24 | 11 | 10 | C52 | 10 | 7 |
| C25 | 3 | 0 | C56 | 6 | 8 |
| C26 | 4 | 4 | C58 | 4 | 4 |
| C29 | 0 | 4 | C61 | 9 | 10 |
| C30 | 0 | 0 | C62 | 10 | 11 |
| C31 | 3 | 8 | C64 | 7 | 9 |

Embodiment 11: Preparation of Insecticide Composition Containing the Compound of the Present Invention (1) Oily Suspension.

The following components were prepared in proportion: 25% (weight percentage, same below) of any one of the above compounds; 5% of polyoxyethylene sorbitan hexaoleate; and 70% of higher aliphatic hydrocarbon oil. The components were ground together in a sand mill until sizes of solid particles were 5 μm or less. The viscous suspension obtained could either be used directly, or used after being emulsified in water.

(2) Aqueous Suspension.

The following components were prepared in proportion: 25% of any one of the above compounds; 3% of hydrated attapulgite; 10% of calcium lignosulfonate; 0.5% of sodium dihydrogenphosphate; and 61.5% of water. The components were ground together in a ball mill until sizes of solid particles were approximately 10 μm or less. The aqueous suspension could be used directly.

(3) Bait.

The following components were prepared in proportion: 0.1 to 10% of any one of the above compounds; 80% of wheat flour; and 19.9 to 10% of molasses. These components were completely mixed to form a bait shape as required. The edible baits could be dispersed to places infested by sanitary insect pests, for example, furniture or industrial places, such as kitchens, hospitals or shops or outdoor areas, so as to control the pests by oral ingestion.

Finally, it should be noted that the above embodiments are only used to illustrate the technical solutions of the present invention, but are not intended to limit the scope of protection of the present invention. Those of ordinary skill in the art can make other different forms of transformations or changes based on the above description and ideas. All the embodiments need not and cannot be exhaustive here. Any modifications, equivalent substitutions, and improvements made within the spirit and principle of the present invention shall all fall within the scope of protection of the claims of the present invention.

What is claimed is:

1. A fused heterocyclic compound, and an optical isomer, cis and trans isomers or an agromedically acceptable salt thereof, the fused heterocyclic compound has a structure shown in formula (I):

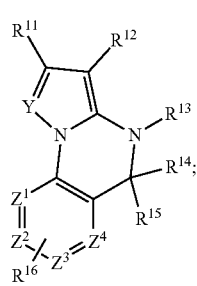

formula (I)

wherein $R^{11}$ and $R^{12}$ are each independently hydrogen, halogen, $-NO_2$, $-CN$, $-COR^{17}$, $-CO_2R^{17}$, $-CONR^{17}R^{18}$, $-S(O)\ R^{17}$, $-S(O)_2\ R^{17}$, $-N\ R^{17}\ R^{18}$, $-N\ R^{17}CO\ R^{18}$, $-N\ R^{17}CON\ R^{18}R^{19}$, $-N\ R^{17}CO_2\ R^{18}$, $-N\ R^{17}S(O)_2\ R^{18}$, alkyl, heteroalkyl, alkenyl, cycloalkyl, cycloalkenyl, aryl, heterocyclyl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$;

$R^{13}$ is hydrogen, $-COR^{17}$, $-CO_2\ R^{17}$, $-S(O)_2\ R^{17}$, $-CONR^{17}R^{18}$, alkyl, heteroalkyl, alkenyl, cycloalkyl, cycloalkenyl and aryl; wherein the alkyl, the alkenyl, the cycloalkyl, the cycloalkenyl and the aryl are unsubstituted or substituted with one or more substituents $R^{10}$;

$R^{14}$ and $R^{15}$ are each independently hydrogen, halogen, $-CN$, $-OH$, $-N\ R^{17}\ R^{18}$, $-O\ R^{17}$, $-CO\ R^{17}$, $-CO_2\ R^{17}$, $-CONR^{17}R^{18}$, $-N\ R^{17}CON\ R^{18}$, $-NR^{17}CON\ R^{18}R^{19}$, $-NR^{17}CO_2R^{18}$, $-NR^{17}S(O)_2R^{18}$, $-S(O)R^{17}$, $-S(O)_2R^{17}$, alkyl, heteroalkyl, alkenyl, cycloalkyl, cycloalkenyl, aryl, heterocyclyl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$, and $R^{14}$ and $R^{15}$ are not hydrogen at the same time;

Y is N or CH;

$Z^1$, $Z^2$, $Z^3$ and $Z^4$ are each independently C or N, under conditions that at most two of $Z^1$ to $Z^4$ are N, and a ring containing $Z^1$ to $Z^4$ is aromatic;

$R^{16}$ represents a substituent on the ring containing $Z^1$ to $Z^4$, one or more $R^{16}$ are provided, and each $R^{16}$ is independently hydrogen, halogen, —CN, alkyl, heteroalkyl, —CO $R^{17}$, —$CO_2$ $R^{17}$, —N $R^{17}R^{18}$, —$CONR^{17}R^{18}$, —N $R^{17}CO$ $R^{18}$, —$NR^{17}CON$ $R^{18}R^{19}$, —$NR^{17}CO_2R^{18}$ or —$NR^{17}S(O)_2R^{18}$;

$R^{17}$, $R^{18}$ and $R^{19}$ are each independently hydrogen, alkyl, heteroalkyl, alkenyl, cycloalkyl, cycloalkenyl, heterocyclyl, aryl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$; and $R^{10}$ is halogen, $C_1$-$C_6$ alkyl, $C_2$-$C_6$ alkenyl, substituted or unsubstituted cycloalkyl, cycloalkenyl, substituted or unsubstituted aryl, substituted or unsubstituted heterocyclyl, —CN, —$NH_2$, —OR''', —NR'''R'''', —COR''', —$CO_2$R''', —CONR'''R'''', —NR'''COR'''', —NR'''CONR'''R'''', —NR'''$CO_2$R'''', —$S(O)_2$R''' or —NR'''S$(O)_2$R'''', wherein R''' and are each independently hydrogen, $C_1$-$C_6$ alkyl, $C_2$-$C_6$ alkenyl, cycloalkyl, cycloalkenyl, aryl, heteroaryl or heterocyclyl.

2. The compound according to claim 1, or the optical isomer, the cis and trans isomers or the agromedically acceptable salt of the compound, wherein;

$R^{11}$ is halogen, —CN, —$COR^{17}$, —$CONR^{17}R^{18}$, —S(O) $R^{17}$, —N $R^{17}$ $R^{18}$,—N $R^{17}CO$ $R^{18}$, aryl, heterocyclyl or heteroaryl; wherein the aryl, the heterocyclyl or the heteroaryl is unsubstituted or substituted with one or more substituents $R^{10}$;

$R^{12}$ is hydrogen, —$COR^{17}$, —$CONR^{17}R^{18}$, —$S(O)R^{17}$, —$S(O)_2R^{17}$, —N $R^{17}$ $R^{18}$, —N $R^{17}CO$ $R^{18}$, —$NR^{17}CONR^{18}R^{19}$, —$NR^{17}CO_2R^{18}$, aryl, heterocyclyl or heteroaryl; wherein the aryl, the heterocyclyl or the heteroaryl is unsubstituted or substituted with one or more substituents $R^{10}$;

$R^{13}$ is hydrogen, —$COR^{17}$, alkyl, heteroalkyl or alkenyl;

$R^{14}$ is halogen, —CN, —N $R^{17}$ $R^{18}$, —O $R^{17}$, —CO $R^{17}$, —$CO_2$ $R^{17}$, —$CONR^{17}R^{18}$, —N $R^{17}CO$ $R^{18}$, —$NR^{17}CO_2R^{18}$, alkyl, heteroalkyl or alkenyl; wherein the alkyl, the heteroalkyl or the alkenyl is unsubstituted or substituted with one or more substituents $R^{10}$; and $R^{15}$ is hydrogen, halogen, —CN, —N $R^{17}$ $R^{18}$,—O $R^{17}$, —CO $R^{17}$, —$CO_2$ $R^{17}$, —$CONR^{17}R^{18}$, —N $R^{17}CO$ $R^{18}$, —$NR^{17}CO_2R^{18}$, alkyl, heteroalkyl or alkenyl; wherein the alkyl, the heteroalkyl or the alkenyl is unsubstituted or substituted with one or more substituents $R^{10}$.

3. The compound according to claim 1, or the optical isomer, the cis and trans isomers or the agromedically acceptable salt of the compound, wherein when $Z^1$, $Z^2$, $Z^3$ and $Z^4$ are all C, one or more $R^{16}$ are provided, and each $R^{16}$ is independently hydrogen, halogen, alkyl, heteroalkyl, alkenyl, —S(O) $R^{17}$, —$S(O)_2$ $R^{17}$, —$COR^{17}$, —N $R^{17}$ $R^{18}$, —$CONR^{17}R^{18}$, —N $R^{17}CO$ $R^{18}$ or —$NR^{17}S(O)_2R^{18}$;

$R^{11}$ is halogen, —CN, —$COR^{17}$, —$CONR^{17}R^{18}$, —S(O) $R^{17}$, —N $R^{17}$ $R^{18}$, —N $R^{17}CO$ $R^{18}$, aryl, heterocyclyl or heteroaryl; wherein the aryl, the heterocyclyl or the heteroaryl is unsubstituted or substituted with one or more substituents $R^{10}$;

$R^{12}$ is —$CONR^{17}R^{18}$, —S(O) $R^{17}$, —$S(O)_2$ $R^{17}$, —N $R^{17}$ $R^{18}$, —N $R^{17}CO$ $R^{18}$, —N $R^{17}CON$ $R^{18}R^{19}$, aryl, heterocyclyl or heteroaryl; wherein the aryl, the heterocyclyl or the heteroaryl is unsubstituted or substituted with one or more substituents $R^{10}$;

$R^{13}$ is hydrogen, —$COR^{17}$, alkyl or alkenyl; and $R^{14}$ and $R^{15}$ are each independently halogen, —CN, —N $R^{17}$ $R^{18}$, —O $R^{17}$, —CO $R^{17}$, —$CO_2$ $R^{17}$, —$CONR^{17}R^{18}$, —N $R^{17}CO$ $R^{18}$, —$NR^{17}CO_2R^{18}$, alkyl, heteroalkyl and alkenyl;

wherein the alkyl, the heteroalkyl and the alkenyl is unsubstituted or substituted with one or more substituents $R^{10}$.

4. The compound according to claim 1, or the optical isomer, the cis and trans isomers or the agromedically acceptable salt of the compound, wherein, $R^{11}$ is halogen, —CN, —$COR^{17}$, —$CONR^{17}R^{18}$, —S(O) $R^{17}$, —N $R^{17}$ $R^{18}$ or —N $R^{17}CO$ $R^{18}$;

$R^{12}$ is —S(O) $R^{17}$, —$S(O)_2$ $R^{17}$, —N $R^{17}$ $R^{18}$, —N $R^{17}CO$ $R^{18}$, aryl or heteroaryl; wherein the aryl or the heteroaryl is unsubstituted or substituted with one or more substituents $R^{10}$;

$R^{13}$ is hydrogen, —$COR^{17}$, alkyl or alkenyl;

$R^{14}$ and $R^{15}$ are each independently halogen, —CN, —N $R^{17}$ $R^{18}$, —O $R^{17}$, —CO $R^{17}$, —$CO_2$ $R^{17}$, —$CONR^{17}R^{18}$, —N $R^{17}CO$ $R^{18}$, —$NR^{17}CO_2R^{18}$, alkyl, heteroalkyl or alkenyl;

wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen, alkyl, heteroalkyl, —S(O) $R^{17}$, —$S(O)_2$ $R^{17}$, —$COR^{17}$, —N $R^{17}$ $R^{18}$, —N $R^{17}CO$ $R^{18}$ or —$NR^{17}S(O)_2R^{18}$.

5. The compound according to claim 4, or the optical isomer, the cis and trans isomers or the agromedically acceptable salt of the compound, wherein, $R^{11}$ is halogen, —CN, —$COR^{17}$ or —$CONR^{17}R^{18}$;

$R^{12}$ is —s(o)$R^{17}$, —$S(O)_2R^{17}$, —$NR^{17}COR^{18}$, aryl or heteroaryl; wherein the aryl or the heteroaryl is unsubstituted or substituted with one or more substituents $R^{10}$;

$R^{13}$ is hydrogen, —$COR^{17}$ or alkyl; and $Z^1$, $Z^2$, and $Z^4$ are all C, one or more $R^{16}$ are provided, and each $R^{16}$ is independently halogen, heteroalkyl, —S(O) $R^{17}$, —$NR^{17}R$ or —$NR^{17}COR^{18}$.

6. The compound according to claim 4, or the optical isomer, the cis and trans isomers or the agromedically acceptable salt of the compound, wherein $R^{11}$ —CN or —$COR^{17}$;

$R^{12}$ is —$S(O)R^{17}$ or aryl; wherein the aryl is substituted with one or more substituents $R^{10}$;

$R^{13}$ is hydrogen, —$COR^{17}$, methyl or ethyl;

$R^{14}$ and $R^{15}$ are each independently halogen, —$OR^{17}$, —$COR^{17}$, —$CO_2R^{17}$, —$CONR^{17}R^{18}$, —$NR^{17}COR^{18}$, —$NR^{17}CO_2R^{18}$, alkyl, heteroalkyl or alkenyl; wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen or heteroalkyl.

7. The compound according to claim 4, or the optical isomer, the cis and trans isomers or the agromedically acceptable salt of the compound, wherein, $R^{11}$ is —CN or —$COR^{17}$, and $R^{17}$ is alkyl or heteroalkyl;

$R^{12}$ is —$S(O)R^{17}$, and $R^{17}$ is alkyl or heteroalkyl;

$R^{13}$ is hydrogen, —$COR^{17}$, methyl or ethyl, and $R^{17}$ is alkyl;

$R^{14}$ and $R^{15}$ are each independently halogen, —$OR^{17}$, —$COR^{17}$, —$CO_2R^{17}$, —$CONR^{17}R^{18}$, —$NR^{17}COR^{18}$, —$NR^{17}CO_2R^{18}$, alkyl, heteroalkyl or alkenyl; wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen or heteroalkyl.

8. A pyrazole-ring-containing fused heterocyclic compound, and an optical isomer, cis and trans isomers or an agromedically acceptable salt thereof, the pyrazole-ring-containing fused heterocyclic compound having a structure shown in formula (II):

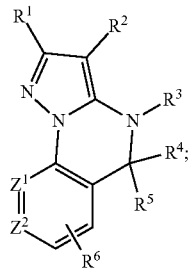

formula (II)

wherein $R^1$ is hydrogen, halogen, —CN, alkyl, heteroalkyl, aryl or heteroaryl;
wherein the alkyl, the aryl or the heteroaryl is unsubstituted or substituted with one or more substituents $R^9$;

$R^2$ is hydrogen, halogen, —CN, —S(O)$R^7$, —S(O)$_2R^7$, alkyl, heteroalkyl, aryl or heteroaryl; wherein the alkyl, the aryl or the heteroaryl is unsubstituted or substituted with one or more substituents $R^9$;

$R^3$ is hydrogen, —COR$^7$, alkyl or heteroalkyl;

$R^4$ and $R^5$ are each independently hydrogen, halogen, —CN, —COR$^7$, —CO$_2R^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted by one or more substituents $R^9$, and $R^4$ and $R^5$ are not hydrogen at the same time;

$Z^1$ and $Z^2$ are each independently C or N, and are not N at the same time, and a ring containing $Z^1$ and $Z^2$ is an aromatic ring;

$R^6$ represents a substituent on the ring containing $Z^1$ and $Z^2$, one or more $R^6$ are provided, and each $R^6$ is independently hydrogen, halogen, —NO$_2$, —CN, alkyl, heteroalkyl, —OR$^7$, —COR$^7$, —CO$_2R^7$ or —NR$^7R^8$;

$R^7$ and $R^8$ are each independently hydrogen, hydroxyl, amino, $C_1$-$C_6$ alkyl, heteroalkyl, aryl or heteroaryl; wherein the alkyl, the aryl or the heteroaryl is unsubstituted or substituted with one or more substituents $R^9$; and $R^9$ is halogen, $C_1$-$C_6$ alkyl, heteroalkyl, —CN, —NH$_2$, —OH, —COR', —CO$_2R'$ or —CONR'R", wherein R' and R" are independently hydrogen, $C_1$-$C_6$ alkyl or heteroalkyl.

9. The compound according to claim 8, or the optical isomer, the cis and trans isomers or the agromedically acceptable salt of the compound, wherein, when $Z^1$ is N and $Z^2$ is C, $R^6$ is a monosubstituent —CF$_3$ at a 5-position of a pyridine ring, and the general formula of the compound is shown in formula (a):

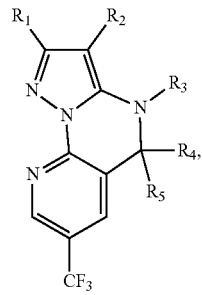

(a)

wherein $R^3$ is hydrogen, methyl or chloromethyl; $R^4$ and $R^5$ are each independently hydrogen, halogen, —CN, —COR$^7$, —CO$_2R^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted by one or more substituents $R^9$;

or, when $Z^2$ is N and $Z^1$ is C, $R^6$ is a monosubstituent chlorine at a 5-position of the pyridine ring, and the general formula of the compound is shown in formula (b):

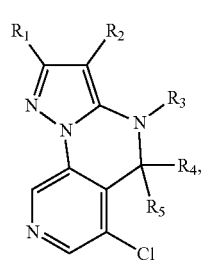

(b)

wherein $R^3$ is hydrogen, methyl or chloromethyl; $R^4$ and $R^5$ are each independently hydrogen, halogen, —CN, —COR$^7$, —CO$_2R^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents $R^9$;

or, when $Z^1$ and $Z^2$ are both C, and $R^6$ is disubstituents at a 3-position and a 5-position of a benzene ring, the general formula of the compound is shown in formula (c):

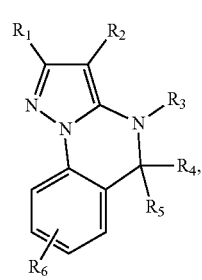

(c)

wherein $R^1$ is —CN or —CF$_3$, and $R^2$ is —CN, —CF$_3$, —OCF$_3$, —SOCF$_3$ or —SOCH$_2$CH$_3$; $R^3$ is hydrogen, —CH$_3$, —Ac or —CH$_2$CH$_2$Cl; a substituent of $R^6$ at the 3-position of the benzene ring is —Cl, —Br, —CF$_3$, —CH$_3$, —CN, —CO$_2$CH$_3$ or —NO$_2$, and a substituent of R$^6$ at the 5-position of the benzene ring is —Cl, —CF$_3$, —OCF$_3$ or —NO$_2$; R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$;

or, when Z$^1$ and Z$^2$ are both C, R$^6$ is disubstituents at a 4-position and a 6-position of the benzene ring, and R$^3$ is hydrogen, the general formula of the compound is shown in formula (d):

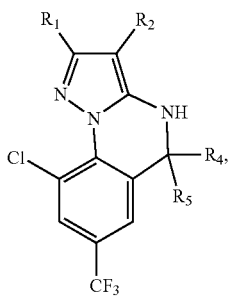

(d)

wherein R$^1$ is —CN, —CF$_3$, —COCH$_3$ or —CH$_2$NH$_2$, and R$^2$ is —OCF$_3$, —CF$_3$, —CN, —SOCF$_3$, —SOCH$_3$, —SOCH$_2$CH$_3$, —SOPh, —SOCH$_2$Ph, —SOC$_6$H$_{13}$,

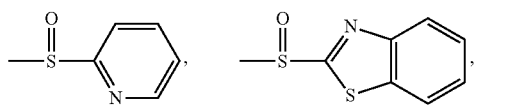

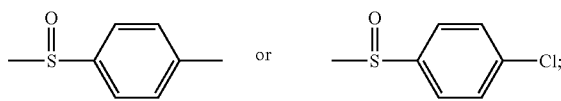

R$^6$ is —Cl or —CF$_3$;

R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$;

Or, when Z$^1$ and Z$^2$ are both C, R$^6$ is disubstituents at the 3-position and the 6-position, or at the 3-position and the 4-position, or at the 4-position and the 5-position, or at the 5-position and the 6-position of the benzene ring, and R$^3$ is hydrogen, the general formula of the compound is shown in formula (e):

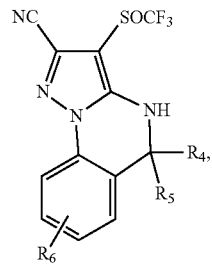

(e)

wherein R$^1$ is —CN, and R$^2$ is —SOCF$_3$; R$^6$ is —Cl or —CF$_3$; R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$;

and R$^4$ and R$^5$ are not hydrogen at the same time.

10. The compound according to claim 9, or the optical isomer, the cis and trans isomers or the agromedically acceptable salt of the compound, wherein R$^4$ and R$^5$ are each independently hydrogen, halogen, —CN, —COR$^7$, —CO$_2$R$^7$, —CH$_2$COR$^7$, —CH$_2$COOR$^7$, amino, alkyl or heteroalkyl; wherein R$^7$ is hydrogen, hydroxyl, C$_{1-4}$ alkyl, C$_{1-4}$ haloalkyl, or amino.

11. The compound according to claim 9, or the optical isomer, the cis and trans isomers or the agromedically acceptable salt of the compound, wherein when the compound is shown in the formula (a) or the formula (b), and any one of R$^4$ and R$^5$ is hydrogen, R$^1$ is —CN, and R$^2$ is —SOCF$_3$ or —OCF$_3$; or R$^1$ is —CF$_3$, and R$^2$ is —SOCF$_3$; or, when neither R$^4$ nor R$^5$ is hydrogen, R$^1$ is —CN or —CF$_3$; and R$^2$ is —SOCF$_3$, —SOCH$_2$CH$_3$, —OCF$_3$, —CF$_3$, —CN or halogen.

12. The compound according to claim 9, or the optical isomer, the cis and trans isomers or the agromedically acceptable salt of the compound, wherein when the compound is shown in the formula (c), R$^3$ is —CH$_3$, —Ac or —CH$_2$CH$_2$Cl, R$^2$ is —SOCF$_3$, R$^1$ is —CN, and both R$^4$ and R$^5$ are —CO$_2$Me;

or, when R$^3$ is hydrogen, and R$^2$ is —CN, —CF$_3$ or —SOCH$_2$CH$_3$, R$^1$ is —CN or —CF$_3$, and R$^4$ and R$^5$ are each independently —CO$_2$Me or —CH$_2$CO$_2$Me;

or, when R$^3$ is hydrogen, and R$^2$ is —OCF$_3$ or —SOCF$_3$, R$^1$ is —CN or —CF$_3$, R$^4$ and R$^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$.

13. The compound according to claim 9, or the optical isomer, the cis and trans isomers or the agromedically acceptable salt of the compound, wherein when the compound is shown in the formula (d), R$^3$ is hydrogen, and R$^2$ is —CN, —CF$_3$, —SOPh, —SOCH$_2$Ph, —SOC$_6$H$_{13}$, or

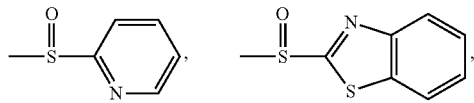

-continued

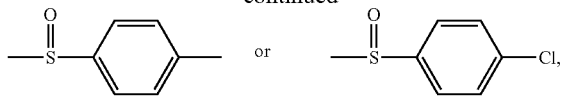

$R^1$ is —CN, and $R^4$ and $R^5$ are each independently —CO$_2$Me or —CO$_2$CH$_2$Me;

or, when $R^3$ is hydrogen, $R^2$ is —SOCF$_3$, and $R^1$ is —COCH$_3$ or —CH$_2$NH$_2$, $R^4$ and $R^5$ are each independently —CO$_2$Me or —CO$_2$CH$_2$Me;

or, when $R^3$ is hydrogen, and $R^2$ is —OCF$_3$ or —SOCF$_3$, $R^1$ is —CN or —CF$_3$, $R^4$ and $R^5$ are each independently hydrogen, halogen, —CN, —COR$^7$, —CO$_2$R$^7$, —CH$_2$COR$^7$, —CH$_2$COOR$^7$, amino, alkyl, heteroalkyl, aryl or heteroaryl; wherein the amino, the alkyl, the aryl or the heteroaryl is unsubstituted or substituted with one or more substituents R$^9$.

14. The compound according to claim 9, or the optical isomer, the cis and trans isomers or the agromedically acceptable salt of the compound, wherein when the compound is shown in the formula (e), $R^6$ is 3-Cl and 6-CF$_3$, 3-Cl and 4-CF$_3$, 4-Cl and 5-CF$_3$, or 5-Cl and 6-CF$_3$ on the benzene ring; and $R^4$ and $R^5$ are each independently —CO$_2$Me, —CH$_2$CO$_2$Me, —CO$_2$Et, —CH$_2$CO$_2$Et, —CH$_2$CO$_2$CH$_2$CF$_3$ or —CH$_2$CO$_2$CH$_2$CHF$_2$.

15. An agricultural composition, comprising:
    (a) 0.001 to 99.99% by weight of the compound according to claim 1, or the optical isomer, the cis and trans isomers or the agromedically acceptable salt thereof, or a combination thereof; and
    (b) an agromedically acceptable carrier and/or excipient.

16. A method of killing or preventing agroforestry pests, sanitary insect pests and pests harmful to animal health comprising directly applying the agricultural composition according to claim 15 to the pests or places contacted by the pests.

17. An agricultural composition, comprising:
    (a) 0.001 to 99.99% by weight of the compound according to claim 8, or the optical isomer, the cis and trans isomers or the agromedically acceptable salt thereof, or a combination thereof; and
    (b) an agromedically acceptable carrier and/or excipient.

18. A method of killing or preventing agroforestry pests, sanitary insect pests and pests harmful to animal health comprising directly applying the agricultural composition according to claim 17 to the pests or places contacted by the pests.

* * * * *

UNITED STATES PATENT AND TRADEMARK OFFICE
CERTIFICATE OF CORRECTION

PATENT NO. : 11,401,271 B2
APPLICATION NO. : 16/758053
DATED : August 2, 2022
INVENTOR(S) : Xu et al.

Page 1 of 2

It is certified that error appears in the above-identified patent and that said Letters Patent is hereby corrected as shown below:

In the Claims

At Columns 137-139, Claim 1 should read as follows:
1. A fused heterocyclic compound, and an optical isomer, cis and trans isomers or an agromedically acceptable salt thereof, the fused heterocyclic compound has a structure shown in formula (I):

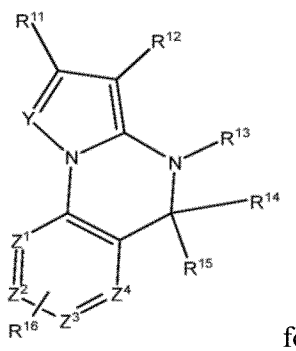

formula (I)

wherein $R^{11}$ and $R^{12}$ are each independently hydrogen, halogen, —$NO_2$, —CN, —$COR^{17}$, —$CO_2R^{17}$, —$CONR^{17}R^{18}$, —S(O) $R^{17}$, —$S(O)_2$ $R^{17}$, —N $R^{17}$ $R^{18}$, —N $R^{17}$CO $R^{18}$, —N $R^{17}$CON $R^{18}R^{19}$, —N $R^{17}CO_2$ $R^{18}$, —N $R^{17}S(O)_2$ $R^{18}$, alkyl, heteroalkyl, alkenyl, cycloalkyl, cycloalkenyl, aryl, heterocyclyl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$;

$R^{13}$ is hydrogen, —$COR^{17}$, —$CO_2R^{17}$, —$S(O)_2$ $R^{17}$, —$CONR^{17}R^{18}$, alkyl, heteroalkyl, alkenyl, cycloalkyl, cycloalkenyl and aryl; wherein the alkyl, the alkenyl, the cycloalkyl, the cycloalkenyl and the aryl are unsubstituted or substituted with one or more substituents $R^{10}$;

$R^{14}$ and $R^{15}$ are each independently hydrogen, halogen, —CN, —OH, —N $R^{17}$ $R^{18}$, —O $R^{17}$, —CO $R^{17}$, —$CO_2$ $R^{17}$, —$CONR^{17}R^{18}$, —N $R^{17}$CON $R^{18}$, —$NR^{17}$CON $R^{18}R^{19}$, —$NR^{17}CO_2R^{18}$, —$NR^{17}S(O)_2R^{18}$, —$S(O)R^{17}$, —$S(O)_2R^{17}$, alkyl, heteroalkyl, alkenyl, cycloalkyl, cycloalkenyl, aryl, heterocyclyl or heteroaryl; wherein the alkyl, the alkenyl, the cycloalkyl, the cycloalkenyl, the aryl, the Signed and Sealed this
Twenty-seventh Day of December, 2022

*Katherine Kelly Vidal*

Katherine Kelly Vidal
*Director of the United States Patent and Trademark Office* heterocyclyl or the heteroaryl is unsubstituted or substituted with one or more substituents $R^{10}$, and $R^{14}$ and $R^{15}$ are not hydrogen at the same time;

Y is N or CH;

$Z^1$, $Z^2$, $Z^3$ and $Z^4$ are each independently C or N, under conditions that at most two of $Z^1$ to $Z^4$ are N, and a ring containing $Z^1$ to $Z^4$ is aromatic;

$R^{16}$ represents a substituent on the ring containing $Z^1$ to $Z^4$, one or more $R^{16}$ are provided, and each $R^{16}$ is independently hydrogen, halogen, —CN, alkyl, heteroalkyl, —CO $R^{17}$, —CO$_2$ $R^{17}$, —N $R^{17}R^{18}$, —CONR$^{17}$R$^{18}$, —N R$^{17}$CO R$^{18}$, —NR$^{17}$CON R$^{18}$R$^{19}$, —NR$^{17}$CO$_2$R$^{18}$ or —NR$^{17}$S(O)$_2$R$^{18}$;

$R^{17}$, $R^{18}$ and $R^{19}$ are each independently hydrogen, alkyl, heteroalkyl, alkenyl, cycloalkyl, cycloalkenyl, heterocyclyl, aryl or heteroaryl; wherein the alkyl, the alkenyl, the cycloalkyl, the cycloalkenyl, the aryl, the heterocyclyl or the heteroaryl is unsubstituted or substituted with one or more substituents $R^{10}$; and $R^{10}$ is halogen, $C_1$-$C_6$ alkyl, $C_2$-$C_6$ alkenyl, substituted or unsubstituted cycloalkyl, cycloalkenyl, substituted or unsubstituted aryl, substituted or unsubstituted heterocyclyl, —CN, —NH$_2$, —OR''', —NR'''R'''', —COR''', —CO$_2$R''', —CONR''' R'''', —NR'''CO R'''', —NR'''CONR''' R'''', —NR'''CO$_2$ R'''', —S(O)$_2$R''' or —NR'''S(O)$_2$ R'''', wherein R''' and R'''' are each independently hydrogen, $C_1$-$C_6$ alkyl, $C_2$-$C_6$ alkenyl, cycloalkyl, cycloalkenyl, aryl, heteroaryl or heterocyclyl.

At Column 140, Claim 5 should read as follows:

5. The compound according to claim 4, or the optical isomer, the cis and trans isomers or the agromedically acceptable salt of the compound, wherein, $R^{11}$ is halogen, —CN, —COR$^{17}$ or —CONR$^{17}$R$^{18}$;

$R^{12}$ is —S(O)R$^{17}$, —S(O)$_2$R$^{17}$, —NR$^{17}$COR$^{18}$, aryl or heteroaryl; wherein the aryl or the heteroaryl is unsubstituted or substituted with one or more substituents $R^{10}$;

$R^{13}$ is hydrogen, —COR$^{17}$ or alkyl; and $Z^1$, $Z^2$, $Z^3$ and $Z^4$ are all C, one or more $R^{16}$ are provided, and each $R^{16}$ is independently halogen, heteroalkyl, —S(O)R$^{17}$, —NR$^{17}$R$^{18}$ or —NR$^{17}$COR$^{18}$.

At Column 140, Claim 6 should read as follows:

6. The compound according to claim 4, or the optical isomer, the cis and trans isomers or the agromedically acceptable salt of the compound, wherein $R^{11}$ is —CN or —COR$^{17}$;

$R^{12}$ is —S(O)R$^{17}$ or aryl; wherein the aryl is substituted with one or more substituents $R^{10}$;

$R^{13}$ is hydrogen, —COR$^{17}$, methyl or ethyl;

$R^{14}$ and $R^{15}$ are each independently halogen, —OR$^{17}$, —COR$^{17}$, —CO$_2$R$^{17}$, —CONR$^{17}$R$^{18}$, —NR$^{17}$COR$^{18}$, —NR$^{17}$CO$_2$R$^{18}$, alkyl, heteroalkyl or alkenyl; wherein the alkyl or the alkenyl is unsubstituted or substituted with one or more substituents $R^{10}$; and $Z^1$, $Z^2$, $Z^3$ and $Z^4$ are all C, one or more $R^{16}$ are provided, and each $R^{16}$ is independently halogen or heteroalkyl.